Figure 1:
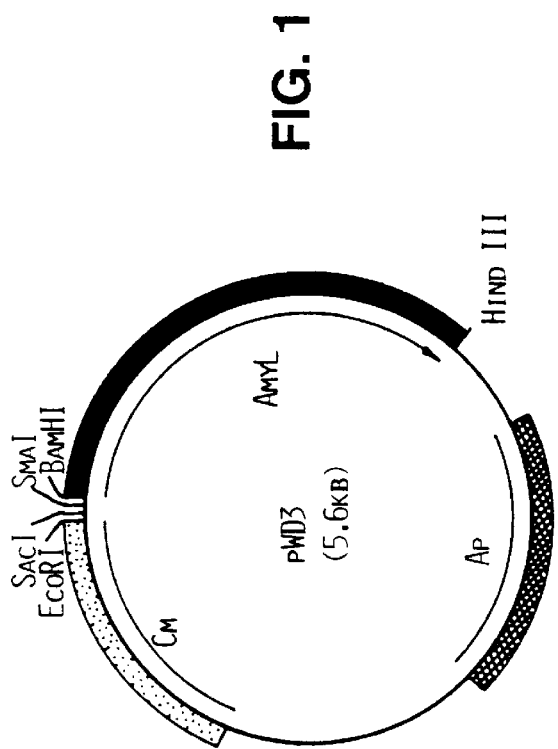

United States Patent [19]
McConnell et al.

[11] Patent Number: 5,843,702
[45] Date of Patent: Dec. 1, 1998

[54] GENE EXPRESSION SYSTEM

[75] Inventors: David John McConnell, Dublin; Kevin Martin Devine, Dublin 8, both of Ireland; Charles O'Kane, Coventry, Great Britain

[73] Assignee: Novo Nordisk A/S, Bagsvaerd, Denmark

[21] Appl. No.: 248,839

[22] Filed: May 25, 1994

Related U.S. Application Data

[63] Continuation of Ser. No. 961,718, filed as PCT/DK91/00074, Mar. 11, 1991, abandoned.

[30]    Foreign Application Priority Data

Mar. 11, 1990 [IE] Ireland .................................... 2893/89

[51] Int. Cl.$^6$ .......................... C12P 21/00; C12N 15/75; C12N 1/21; C07H 21/04
[52] U.S. Cl. ................ 435/69.1; 435/172.3; 435/252.31; 435/320.1; 536/23.7; 536/23.72; 536/24.1
[58] Field of Search ................................ 435/69.1, 91.1, 435/172.3, 252.5, 320.1, 172.1, 252.31; 536/27.1, 23.7, 23.72, 24.1

[56]                References Cited

PUBLICATIONS

Osburne et al. (1985) J. Bacteriol vol. 163(3): 1101–1108.
Mieschendahl et al. (1985) J. Bacteriol. vol. 164(3): 1366–1369.
Rosenthal et al. (1979) Genetics vol. 92(3): 721–740.
O'Kane et al. (1986) J. Bacteriol. vol. 168(2): 973–981.
Buxton (1976) J. Virol. vol. 20(1): 22–28.
Yudkin et al. (1989) J. Gen. Microbio. vol. 135: 767–775.
Moran et al. (1982) Mol. Gen. Genet. vol. 186: 339–346.
Heather Wood et al., Gene, vol. 96, pp. 83–88 (1990).
Wood et al., J. Bacteriology, vol. 172, No. 5, pp. 2667–2674 (1990).
Anderson et al., J. Virology, vol. 54, No. 3, pp. 773–780 (1985).
Piggot et al., J. Gen. Microbiology, vol. 128, pp. 663–669 (1982).
Ward et al., J. gen. Microbiology, vol. 128, p. 1171–1178 (1982).
Anderson et al., J. Bacteriology, vol. 150, No. 3, pp. 1280–1286 (1982).
R. S. Buxton, J. Gen. Virol., vol. 46, pp. 427–437 (1980).

*Primary Examiner*—David Guzo
*Attorney, Agent, or Firm*—Steve T. Zelson, Esq.; Valeta A. Gregg, Esq.

[57]                ABSTRACT

The present invention relates to an expression system which comprises a phage-like bacteriocin("phibacin") or a mutant thereof, or a gene or mutant of a phibacin having a function in gene expression, such as a repressor gene, which is used to transform bacterial host for the producion of proteins, in particular in gram positive bacteria.

32 Claims, 23 Drawing Sheets

FIG. 8a

```
ctgttctctaaaacatataaaaagtagaccgatataaagaaaaaagtgtttatttttaaagaaaaggga
aagatttctacactaccttccagtcctatacggctttctttctgctaaaaacagaacaaacgttcga
aagggagtattcaattgggcgattacttatcacatctggaggaatacgttaaaaattatacggccggct
gggcatcacatcccctcatcacattgacatgctgaaatcgcaaaggatctgatatcgtatattgggtgcattttt
gaggatatggggagcatgatggtgaaatacgacggcatgtacagtatcgtattgaaccaaaaaaagtcac
gggaagagcaatgggaggattttggccatgagctgtgccacgtgttaaagcatgcaggcaatcattttca
gatgaacaagctcttcagagagcttcaggaattc
```

*FIG. 8b*

```
                                                      M
                                                      atgtgatatcactctcctgatctgTTTTGATACTTTTCGTA    258
                                                                              t              a
                                                                                              t TCaactgttaccaagtataaacgatacaaactgtatcatcaagttatTTTTGATACTTTTTATCataa              328
gga                                            tt ctttaTTTGATACAGATTGTATCtataatcattagtaacttaggagtttaaaaagagaggtcatagt              398
                        tt                  a        g atgataggcagcagattgaagagtctcagagggaaaaggacacaggaagagaaatcgtatctcatatcggtg          468
 M  I  G  S  R  L  K  S  L  R  G  K  R  T  Q  E  E  I  V  S  H  I  G  V
       G                                                 c  a  c
                                                            A tgtcgcgggcacgatattcccactatgaaaacgggcgaagcgaacctgattacgacacactccaaaagct           538
 S  R  A  R  Y  S  H  Y  E  N  G  R  S  E  P  D  Y  D  T  L  Q  K  L
    a                                             c ggctgattacttcaagtaacgactgattacttattaacaggaaagacaaaaatccgatgacgatatg              608
 A  D  Y  F  Q  V  T  D  Y  L  L  T  G  K  D  K  K  S  D  D  D  M
       g                       g tttcagatccgacttgcaggtagcataccgtgatatgcaggattttcccagaaagcaaacagcagg               678
 F  S  D  P  D  L  Q  V  A  Y  R  D  M  Q  D  F  S  P  E  S  K  Q  Q  A
             c  c  t
                   L
```

FIG. 9a

```
ccattgaatttatcaactatttaaaagaaaaagagaaaaaccgaaaccgaaaaataaataatatttct  748
         c                                   c                  cg
     I   E   F   I   N   Y   L   K   E   K   N   R   K   P   K   N   K     orfi(ts)

ctgtctctaaaacatatgaaaatagaccgatataagaaaaagtgttatttttaagaaaaggga  818
                            a  g                          a aagatttcaacacacttccagtcctattaggctttctttctcgctaaaaacagaacacacgttcgaa  888
                    t  v  c          ac                              a
                    t agggagtattcaattgggcgattacttatcacatctggaggaatacgtaaaaattatacagccggctg  958
                                                    t                g ggcatcacctcccccatcacacattgacatgctgaaaatcgcaaaggatctggatatttgggttcatttttg  1028
              a  t                                                    g aggatatggggagcatgatggttaaatacgatggcatgtacagtatcgtattgaatcaaagaaaatcacg  1098
                                       c                          a  g agaagagcaatgggaggatttttggccatgaactgtgccacgtgttaaagcacgcaggcaatcattttcaa  1168
                          g                                  t           g atgaacaagctcttcagggaactgcag  1195
         a  g           t
```

*FIG. 9b*

FIG. 14a

```
                                                                              t
cgatatgcaggatttttccccagaaagcaaacagcaggccatcgaatttatcaactatttaaaagaaaaagagaaaaacc  718
 D  M  Q  D  F  S  P  E  S  K  Q  Q  A  I  E  F  I  N  Y  L  K  E  K  N  R
              at                  g       a
gcaaaccgaaaataaataaatcgttctctgttctctaaaacatataaaaagtagaccgatataaagaaaaaagtgttta  798
 K  P  K  N  K  v
      t                            a  -  t                                   c
tttttttaaagaaaagggaaagatttctacactacctccagtcctatacggcttttcttttctcgctaaaaacagaacaa  878
                                                         a
acgttcgaaagggagtattcaattgggcgattacttatcacatctggaggaatacgttaaaaatttatacggccggctgg  958
                                             t    g  a  a
gcatcacatcccctcatcacattgacatgctgaaaatcgcaaaggatctggatatattgggtgcatttgaggatatgggg 1038
                                                                     g  a  g
agcatgatgtgaaatacgacggcatgtacagtatcgtattgaaccaaaaaaagtcacgggaagagcaatgggaggattt 1118
   c              a                 c                a
tggccatgagctgtgccacgtgttaaagcatgcaggcaatcatttcagatgaacaagctcttcagagagcttcaggaattc 1200
```

FIG. 14b

```
    K L C Q T K K V I V E H T G I G V V F H
      S F V K Q R K S L W N I P V L E L F F I
        A L S N K E S H C G T Y R Y W S C F S S
    AAGCTTTGTCAAACAAAGAAAGTCATTGTGGAACATACCGGTATTGGAGTTGTTTTTCAT
            10        20        30        40        50        60
    TTCGAAACAGTTTGTTTCTTTCAGTAACACCTTGTATGGCCATAACCTCAACAAAAAGTA
    L K T L C L F D N H F M G T N S N N K M
      A K D F L S L * Q P V Y R Y Q L Q K E D
        S Q * V F F T M T S C V P I P T T K * G

P C P N C R S A T D L T P V I Q K L E Q
      H V R T A G P R L T * R L S F K S W S K
        M S E L P V R D * L N A C H S K A G A N
    CCATGTCCGAACTGCCGGTCCGCGACTGACTTAACGCCTGTCATTCAAAAGCTGGAGCAA
            70        80        90        100       110       120
    GGTACAGGCTTGACGGCCAGGCGCTGACTGAATTGCGGACAGTAAGTTTTCGACCTCGTT
    W T R V A P G R S V * R R D N L L Q L L
      M D S S G T R S Q S L A Q * E F A P A F
        H G F Q R D A V S K V G T M * F S S C I

M L T A G K A R L N I Y D * T A D C S N
      C * Q R E K R G * I S M I K Q L T A L I
        A D S G K S E A E Y L * L N S * L L * S
    ATGCTGACAGCGGGAAAAGCGAGGCTGAATATCTATGATTAAACAGCTGACTGCTCTAAT
            130       140       150       160       170       180
    TACGACTGTCGCCCTTTTCGCTCCGACTTATAGATACTAATTTGTCGACTGACGAGATTA
    H Q C R S F R P Q I D I I L C S V A R I
      A S L P F L S A S Y R H N F L Q S S * D
        S V A P F A L S F I * S * V A S Q E L R

R F A V S G K A N R K K H * T M V * G R
      A L L F R A K R T E K N I E Q W Y K D D
        L C C F G Q S E Q K K T L N N G I R T T
    CGCTTTGCTGTTTCGGGCAAAGCGAACAGAAAAAAACATTGAACAATGGTATAAGGACGA
            190       200       210       220       230       240
    GCGAAACGACAAAGCCCGTTTCGCTTGTCTTTTTTTGTAACTTGTTACCATATTCCTGCT
    A K S N R A F R V S F F M S C H Y L S S
      S Q Q K P C L S C F F V N F L P I L V V
        K A T E P L A F L F F C Q V I T Y P R R

R E V K V L A K T K Q A E K S P A P W R
      G K * K C W Q R Q N R Q R K A L R R G V
        G S E S V G K D K T G R E K P C A V A C
    CGGGAAGTGAAAGTGTTGGCAAAGACAAAACAGGCAGAGAAAAGCCCTGCGCCGTGGCGT
            250       260       270       280       290       300
    GCCCTTCACTTTCACAACCGTTTCTGTTTTGTCCGTCTCTTTTCGGGACGCGGCACCGCA
    P F H F H Q C L C F L C L F A R R R P T
      P L S L T P L S L V P L S F G Q A T A H
        S T F T N A F V F C A S F L G A G H R A

A V P C G D T K P I Y I Y S A Y S E E E
      L S R A G I R N R S I F I Q L T V K K K
        C P V R G Y E T D L Y L F S L Q * R R K
    GCTGTCCCGTGCGGGGATACGAAACCGATCTATATTTATTCAGCTTACAGTGAAGAAGAA
            310       320       330       340       350       360
    CGACAGGGCACGCCCCTATGCTTTGGCTAGATATAAATAAGTCGAATGTCACTTCTTCTT
    S D R A P I R F R D I N I * S V T F F F
      Q G T R P Y S V S R Y K N L K C H L L F
        T G H P S V F G I * I * E A * L S S S F
```

FIG. 15a

```
  K E R F P Y S N G R L I A A V F D L S S
   K K D F R T Q T G G * L Q L Y L T S A L
    R K I S V L K R A A D C S C I * P Q L L
AAAGAAAGATTTCCGTACTCAAACGGGCGGCTGATTGCAGCTGTATTTGACCTCAGCTCT
      370       380       390       400       410       420
TTTCTTTCTAAAGGCATGAGTTTGCCCGCCGACTAACGTCGACATAAACTGGAGTCGAGA
 F F S K R V * V P P Q N C S Y K V E A R
    L F I E T S L R A A S Q L Q I Q G * S K
     S L N G Y E F P R S I A A T N S R L E *

Y S Q K S N A S L M A A A P E L L E A S
    I R K K A M P L * W P L R L N C W K R L
     F A K K Q C L F D G R C A * I A G S V *
TATTCGCAAAAAAGCAATGCCTCTTTGATGGCCGCTGCGCCTGAATTGCTGGAAGCGTCT
      430       440       450       460       470       480
ATAAGCGTTTTTTCGTTACGGAGAAACTACCGGCGACGCGGACTTAACGACCTTCGCAGA
 I R L F A I G R Q H G S R R F Q Q F R R
    N A F F C H R K S P R Q A Q I A P L T *
     E C F L L A E K I A A A G S N S S A D L

K A A V D F L K G N S I H S K E R I I Q
   K Q Q L I F * K G I L F I Q R S V S F S
     S S S * F S E R E F Y S F K G A Y H S A
AAAGCAGCAGTTGATTTTCTGAAAGGGAATTCTATTCATTCAAAGGAGCGTATCATTCAG
      490       500       510       520       530       540
TTTCGTCGTCAACTAAAAGACTTTCCCTTAAGATAAGTAAGTTTCCTCGCATAGTAAGTC
 F C C N I K Q F P I R N M * L L T D N L
    L L L Q N E S L S N * E N L P A Y * E A
     A A T S K R F P F E I * E F S R I M * S

L L E K A E A S A A P K R G G N K T * F
   Y * K K L K Q A L H R K G E E I K H D S
     I R K S * S K R C T E K G R K * N M I H
CTATTAGAAAAAGCTGAAGCAAGCGCTGCACCGAAAAGGGGAGGAAATAAAACATGATTC
      550       560       570       580       590       600
GATAATCTTTTTCGACTTCGTTCGCGACGTGGCTTTTCCCCTCCTTTATTTTGTACTAAG
 * * F F S F C A S C R F P S S I F C S E
    I L F L Q L L R Q V S F P L F Y F M I *
     N S F A S A L A A G F L P P F L V H N M

I R K N C C I S I P S R L R A S W R T G
    S E K T A A Y R F R H A * E P A G G R E
     P K K L L H I D S V T L K S Q L E D G K
ATCCGAAAAAACTGCTGCATATCGATTCCGTCACGCTTAAGAGCCAGCTGGAGGACGGGA
      610       620       630       640       650       660
TAGGCTTTTTTGACGACGTATAGCTAAGGCAGTGCGAATTCTCGGTCGACCTCCTGCCCT
 D S F V A A Y R N R * A * S G A P P R S
    G F F S S C I S E T V S L L W S S S P F
     R F F Q Q M D I G D R K L A L Q L V P F

K S V I I V D G I K Q E A W I T E A P E
    N P S L L W T A S S K K H G S Q K R Q S
     I R H Y C G R H Q A R S M D H R S A R A
AAATCCGTCATTATTGTGGACGGCATCAAGCAAGAAGCATGGATCACAGAAGCGCCAGAG
      670       680       690       700       710       720
TTTAGGCAGTAATAACACCTGCCGTAGTTCGTTCTTCGTACCTAGTGTCTTCGCGGTCTC
 F G D N N H V A D L L F C P D C F R W L
    I R * * Q P R C * A L L M S * L L A L A
     D T M I T S P M L C S A H I V S A G S C
```

FIG. 15b

```
          H G K T L V E T R K G D L A R V E F E I
           M E K R S S K Q E R A I L L V W N L K S
            W K N A R R N K K G R S C S C G I * N R
         CATGGAAAAACGCTCGTCGAAACAAGAAAGGGCGATCTTGCTCGTGTGGAATTTGAAATC
              730       740       750       760       770       780
         GTACCTTTTTGCGAGCAGCTTTGTTCTTTCCCGCTAGAACGAGCACACCTTAAACTTTAG
           M S F R E D F C S L A I K S T H F K F D
            H F F A R R F L F P R D Q E H P I Q F R
             P F V S T S V L F P S R A R T S N S I P

G Y K L N * S E N R I R P R R K A C G H
            A T N * I K A K T E Y V Q D G K P A D T
             L Q I K L K R K Q N T S K T E S L R T L
         GGCTACAAATTAAATTAAAGCGAAAACAGAATACGTCCAAGACGGAAAGCCTGCGGACAC
              790       800       810       820       830       840
         CCGATGTTTAATTTAATTTCGCTTTTGTCTTATGCAGGTTCTGCCTTTCGGACGCCTGTG
           A V F * I L A F V S Y T W S P F G A S V
            S C I L N F R F C F V D L V S L R R V S
             * L N F * L S F L I R G L R F A Q P C Q

* S T A Q H L C V D W C P F F I C Q K *
            D Q L H S I C A L I G V R F L F A K N E
             I N C T A F V R * L V S V F Y L P K M R
         TGATCAACTGCACAGCATTTGTGCGTTGATTGGTGTCCGTTTTTTATTTGCCAAAAATGA
              850       860       870       880       890       900
         ACTAGTTGACGTGTCGTAAACACGCAACTAACCACAGGCAAAAAATAAACGGTTTTTACT
           S * S C L M Q A N I P T R K K N A L F S
            I L Q V A N T R Q N T D T K * K G F I L
             D V A C C K H T S Q H G N K I Q W F H P

G G S * N A R L T I * I * T H A Q T N K
            E D H R M Q D L L F E Y K R T L K Q T R
             R I I E C K T Y Y L N I N A R S N K Q E
         GGAGGATCATAGAATGCAAGACTTACTATTTGAATATAAACGCACGCTCAAACAAACAAG
              910       920       930       940       950       960
         CCTCCTAGTATCTTACGTTCTGAATGATAAACTTATATTTGCGTGCGAGTTTGTTTGTTC
           S S * L I C S K S N S Y L R V S L C V L
            L I M S H L V * * K F I F A R E F L C S
             P D Y F A L S V I Q I Y V C A * V F L F

N T I * T A R * G R * I R A L S * R A E
            I Q Y K P L A E A D E S V L S A E E L K
             Y N I N R S L R Q M N P C S Q L K S * R
         AATACAATATAAACCGCTCGCTGAGGCAGATGAATCCGTGCTCTCAGCTGAAGAGCTGAA
              970       980       990      1000      1010      1020
         TTATGTTATATTTGGCGAGCGACTCCGTCTACTTAGGCACGAGAGTCGACTTCTCGACTT
           I C Y L G S A S A S S D T S E A S S S F
            Y L I F R E S L C I F G H E * S F L Q L
             V I Y V A R Q P L H I R A R L Q L A S P

G * K N H Q K Y D Y * S * I C N R M A *
            D K K I I R N M I T D L E Y V T E W L E
             I K K S S E I * L L I L N M * Q N G L K
         GGATAAAAAAATCATCAGAAATATGATTACTGATCTTGAATATGTAACAGAATGGCTTGA
              1030      1040      1050      1060      1070      1080
         CCTATTTTTTTAGTAGTCTTTATACTAATGACTAGAACTTATACATTGTCTTACCGAACT
           S L F I M L F I I V S R S Y T V S H S S
            I F F D D S I H N S I K F I Y C F P K F
             Y F F * * F Y S * Q D Q I H L L I A Q F
```

*FIG.15c*

```
  K R K A A R H Q T G D * P A * C L P A A
   K G R Q P G I R R A I D R R D V Y Q R L
    K E G S P A S D G R L T G V M F T S G *
AAAAGGAAGGCAGCCCGGCATCAGACGGGCGATTGACCGGCGTGATGTTTACCAGCGGCT
      1090      1100      1110      1120      1130      1140
TTTTCCTTCCGTCGGGCCGTAGTCTGCCCGCTAACTGGCCGCACTACAAATGGTCGCCGA
  F P L C G P M L R A I S R R S T * W R S
   F S P L G A D S P R N V P T I N V L P Q
    L F A A R C * V P S Q G A H H K G A A S

D D Q G P E N H R I I F Q R Y D V * A G
   M I K D P R I I E S F S S A M M F E P D
    * S R T R E S S N H F P A L * C L S R T
GATGATCAAGGACCCGAGAATCATCGAATCATTTTCCAGCGCTATGATGTTTGAGCCGGA
      1150      1160      1170      1180      1190      1200
CTACTAGTTCCTGGGCTCTTAGTAGCTTAGTAAAAGGTCGCGATACTACAAACTCGGCCT
  I I L S G L I M S D N E L A I I N S G S
   H D L V R S D D F * K G A S H H K L R V
    S * P G S F * R I M K W R * S T Q A P R

R T G I R R R Q R * N S R S I S P V N G
   G Q V S E E D R D R I R E A L A L L T D
    D R Y Q K K T E I E F E K H * P C * R T
CGGACAGGTATCAGAAGAAGACAGAGATAGAATTCGAGAAGCATTAGCCCTGTTAACGGA
      1210      1220      1230      1240      1250      1260
GCCTGTCCATAGTCTTCTTCTGTCTCTATCTTAAGCTCTTCGTAATCGGGACAATTGCCT
  P C T D S S S L S L I R S A N A R N V S
   S L Y * F F V S I S N S F C * G Q * R V
    V P I L L L C L Y F E L L M L G T L P C

Q R K G N V F A A * G R M F F L * T D R
   R E K E M F L L H K V E C F S Y E R I A
    E K R K C F C C I R * N V F L M N G S P
CAGAGAAAAGGAAATGTTTTTGCTGCATAAGGTAGAATGTTTTTTCTTATGAACGGATCGC
      1270      1280      1290      1300      1310      1320
GTCTCTTTTCCTTTACAAAAACGACGTATTCCATCTTACAAAAAGAATACTTGCCTAGCG
  L S F S I N K S C L T S H K E * S R I A
   S F L F H K Q Q M L Y F T K R I F P D G
    L F P F T K A A Y P L I N K K H V S R R

R S S R R K K I D S A N D D * T G E F K
   D L L G V K K S T V Q T T I K R A S L K
    I F S A * K N R Q C K R R L N G R V * R
CGATCTTCTCGGCGTAAAAAAATCGACAGTGCAAACGACGATTAAACGGGCGAGTTTAAA
      1330      1340      1350      1360      1370      1380
GCTAGAAGAGCCGCATTTTTTTAGCTGTCACGTTTGCTGCTAATTTGCCCGCTCAAATTT
  S R R P T F F D V T C V V I L R A L K F
   I K E A Y F F R C H L R R N F P R T * L
    D E R R L F I S L A F S S * V P S N L S

D A K T A G R N E S I T C L K A C H T F
   M Q R Q Q E E M N R S L A * K L V I R L
    C K D S R K K * I D H L P E S L S Y V C
GATGCAAAGACAGCAGGAAGAAATGAATCGATCACTTGCCTGAAAGCTTGTCATACGTTT
      1390      1400      1410      1420      1430      1440
CTACGTTTCTGTCGTCCTTCTTTACTTAGCTAGTGAACGGACTTTCGAACAGTATGCAAA
  I C L C C S S I F R D S A Q F S T M R K
   H A L F S V L A L P F L F F H S I D S I * V K Q G R S F L A K Q D * Y V T N Q A
```

FIG.15d

```
      A T Y K * I E H D T K R L A D Q P L L *
       P P I S E * S M T L S G W L I S R F Y E
        H L * V N R A * H * A A G * S A A F M N
      GCCACCTATAAGTGAATAGAGCATGACACTAAGCGGCTGGCTGATCAGCCGCTTTTATGA
           1450      1460      1470      1480      1490      1500
      CGGTGGATATTCACTTATCTCGTACTGTGATTCGCCGACCGACTAGTCGGCGAAAATACT
       G G I L S Y L M V S L P Q S I L R K * S
        W R Y T F L A H C * A A P Q D A A K I F
         V * L H I S C S V L R S A S * G S K H I

I N N H A G G G G D A V A * K H N S A N
       * T T M L E V A V M Q * H E N T T A R T
        K Q P C W R W R * C S S M K T Q Q R E Q
      ATAAACAACCATGCTGGAGGTGGCGGTGATGCAGTAGCATGAAAACACAACAGCGCGAAC
           1510      1520      1530      1540      1550      1560
      TATTTGTTGGTACGACCTCCACCGCCACTACGTCATCGTACTTTTGTGTTGTCGCGCTTG
       Y V V M S S T A T I C Y C S F V V A R V
        L C G H Q L H R H H L L M F V C C R S C
         F L W A P P P P S A T A H F C L L A F L

K H * Q S I N N I K E R S Q I G R L R T
       S I S N L S T T S R K D H K S G D C G H
        A L A I Y Q Q H Q G K I T N R A I A D T
      AAGCATTAGCAATCTATCAACAACATCAAGGAAAGATCACAAATCGGGCGATTGCGGACA
           1570      1580      1590      1600      1610      1620
      TTCGTAATCGTTAGATAGTTGTTGTAGTTCCTTTCTAGTGTTTAGCCCGCTAACGCCTGT
       L M L L R D V V D L F S * L D P S Q P C
        A N A I * * C C * P F I V F R A I A S V
         C * C D I L L M L S L D C I P R N R V C

Q S V F P R K Q S A S G K N K T N G K R
       N R C F R E N N R H L E K T R Q M E R G
        I G V S A K T I G I W K K Q D K W K E A
      CAATCGGTGTTTCCGCGAAAACAATCGGCATCTGGAAAAAACAAGACAAATGGAAAGAGG
           1630      1640      1650      1660      1670      1680
      GTTAGCCACAAAGGCGCTTTTGTTAGCCGTAGACCTTTTTTGTTCTGTTTACCTTTCTCC
       L R H K R S F L R C R S F V L C I S L P
        I P T E A F V I P M Q F F C S L H F S A
         D T N G R F C D A D P F F L V F P F L R

R C F L R P K T N K N S A L * T T M N *
       A V F C V Q K R T K T A P Y K Q R * I K
        L F S A S K N E Q K Q R P I N N D E L N
      CGCTGTTTTCTGCGTCCAAAAACGAACAAAAACAGCGCCCTATAAACAACGATGAATTAA
           1690      1700      1710      1720      1730      1740
      GCGACAAAAGACGCAGGTTTTTGCTTGTTTTTGTCGCGGGATATTTGTTGCTACTTAATT
       A T K Q T W F R V F V A G * L C R H I L
        S N E A D L F S C F C R G I F L S S N F
         Q K R R G F V F L F L A R Y V V I F * I

M N A S G C F A C I T S K A S M P H S Q
       * T P A A V L P V L R Q K L Q C H T V S
        E R Q R L F C L Y Y V K S F N A T Q S A
      ATGAACGCCAGCGGCTGTTTTGCCTGTATTACGTCAAAAGCTTCAATGCCACACAGTCAG
           1750      1760      1770      1780      1790      1800
      TACTTGCGGTCGCCGACAAAACGGACATAATGCAGTTTTCGAAGTTACGGTGTGTCAGTC
       H V G A A T N R * F S * H W V T L
        S R W R S N Q R Y * T L L K L A V C D A
         F A L P Q K A Q I V D F A E I G C L * C
```

FIG. 15e

```
    Q  S  K  R  A  I  L  R  T  A  L  M  *  R  A  A  D  S  *  K
    N  Q  S  G  L  F  S  G  Q  R  S  C  D  G  Q  P  T  L  K  K
       I  K  A  G  Y  S  P  D  S  A  H  V  T  G  S  R  L  L  K  N
CAATCAAAGCGGCTATTCTCCGGACAGCGCTCATGTGACGGGCAGCCGACTCTTAAAAA
      1810      1820      1830      1840      1850      1860
GTTAGTTTCGCCCGATAAGAGGCCTGTCGCGAGTACACTGCCCGTCGGCTGAGAATTTTT
    L  *  L  P  S  N  E  P  C  R  E  H  S  P  C  G  V  R  L  F
       I  L  A  P  *  E  G  S  L  A  *  T  V  P  L  R  S  K  F  F
          D  R  F  A  I  R  R  V  A  S  M  H  R  A  A  S  E  *  F  V

T  K  R  S  L  L  K  L  D  A  L  K  K  K  W  S  M  K  C  L
    R  K  G  R  C  *  N  *  T  H  *  K  R  N  G  Q  *  N  V  Y
       E  K  V  A  A  E  I  R  R  I  K  K  E  M  V  N  E  M  F  I
ACGAAAAGGTCGCTGCTGAAATTAGACGCATTAAAAAAGAAATGGTCAATGAAATGTTTA
      1870      1880      1890      1900      1910      1920
TGCTTTTCCAGCGACGACTTTAATCTGCGTAATTTTTTCTTTACCAGTTACTTTACAAAT
    R  F  P  R  Q  Q  F  *  V  C  *  F  L  F  P  *  H  F  T  *
    S  F  T  A  A  S  I  L  R  M  L  F  S  I  T  L  S  I  N  I
       F  L  D  S  S  F  N  S  A  N  F  F  F  H  D  I  F  H  K  N

L  K  R  W  M  C  C  R  F  I  S  R  S  R  L  R  I  L  R  T
    *  S  D  G  C  A  A  G  L  Y  Q  D  R  V  C  G  Y  Y  G  L
       E  A  M  D  V  L  Q  V  V  Y  I  K  I  A  F  A  D  I  T  D  Y
TTGAAGCGATGGATGTGCTGCAGGTTTATATCAAGATCGCGTTTGCGGATATTACGGACT
      1930      1940      1950      1960      1970      1980
AACTTCGCTACCTACACGACGTCCAAATATAGTTCTAGCGCAAACGCCTATAATGCCTGA
    Q  L  S  P  H  A  A  P  K  Y  *  S  R  T  Q  P  Y  *  P  S
    S  A  I  S  T  S  C  T  *  I  L  I  A  N  A  S  I  V  S  *
       F  R  H  I  H  Q  L  N  I  D  L  D  R  K  R  I  N  R  V  I

M  *  P  L  E  K  K  R  S  R  L  S  G  N  R  V  R  C  L  M
    C  D  L  W  K  K  R  G  P  G  C  R  E  I  G  S  A  V  *  *
       V  T  F  G  K  K  E  V  Q  A  V  G  K  S  G  P  L  F  D  E
ATGTGACCTTTGGAAAAAAGAGGTCCAGGCTGTCGGGAAATCGGGTCCGCTGTTTGATG
      1990      2000      2010      2020      2030      2040
TACACTGGAAACCTTTTTTTCTCCAGGTCCGACAGCCCTTTAGCCCAGGCGACAAACTAC
    H  S  R  Q  F  F  L  P  G  P  Q  R  S  I  P  D  A  T  Q  H
    T  V  K  P  F  F  S  T  W  A  T  P  F  D  P  G  S  N  S  S
       H  G  K  S  F  F  L  D  L  S  D  P  F  R  T  R  Q  K  I  F

K  M  I  I  R  L  *  R  K  S  A  L  S  M  S  K  T  P  G  S
    R  *  *  S  D  Y  E  G  N  Q  L  C  R  C  Q  R  L  R  A  R
       D  D  N  P  I  M  K  E  I  S  F  V  D  V  K  D  S  G  L  V
AAGATGATAATCCGATTATGAAGGAAATCAGCTTTGTCGATGTCAAAGACTCCGGGCTCG
      2050      2060      2070      2080      2090      2100
TTCTACTATTAGGCTAATACTTCCTTTAGTCGAAACAGCTACAGTTTCTGAGGCCCGAGC
    L  H  Y  D  S  *  S  P  F  *  S  Q  R  H  *  L  S  R  A  R
    S  S  L  G  I  I  F  S  I  L  K  T  S  T  L  S  E  P  S  T
       I  I  I  R  N  H  L  F  D  A  K  D  I  D  F  V  G  P  E  N

L  M  A  P  L  *  R  K  Q  S  L  G  K  R  H  C  H  Q  A  C
    *  W  H  H  C  N  G  S  K  A  W  E  R  G  I  A  I  K  L  A
       D  G  T  I  V  T  E  A  K  L  G  K  E  A  L  P  S  S  L  Q
TTGATGGCACCATTGTAACGGAAGCAAAGCTTGGGAAAGAGGCATTGCCATCAAGCTTGC
      2110      2120      2130      2140      2150      2160
AACTACCGTGGTAACATTGCCTTCGTTTCGAACCCTTTCTCCGTAACGGTAGTTCGAACG
    Q  H  C  W  Q  L  P  L  L  A  Q  S  L  P  M  A  M  L  S  A
    S  P  V  M  T  V  S  A  F  S  P  F  S  A  N  G  D  L  K  C
       I  A  G  N  Y  R  F  C  L  K  P  F  L  C  Q  W  *  A  Q  L
```

FIG. 15f

```
  R * N E G A * E A I L I F * F V S R S I
   D K M K A L E K L S L Y F D L F P D Q F
    I K * R R L R S Y P Y I L I C F Q I N L
AGATAAAATGAAGGCGCTTGAGAAGCTATCCTTATATTTTGATTTGTTTCCAGATCAATT
      2170      2180      2190      2200      2210      2220
TCTATTTTACTTCCGCGAACTCTTCGATAGGAATATAAAACTAAACAAAGGTCTAGTTAA
  S L I F A S S F S D K Y K S K N G S * N
   I F H L R K L L * G * I K I Q K W I L K
    Y F S P A Q S A I R I N Q N T E L D I *

* T K N * K * E I E A C Q T K S G E N R
   K Q K I E N E K L K L A K Q K A E K T D
    N K K L K M R N * S L P N K K R R K Q M
TAAACAAAAAATTGAAAATGAGAAATTGAAGCTTGCCAAACAAAAAGCGGAGAAAACAGA
      2230      2240      2250      2260      2270      2280
ATTTGTTTTTTAACTTTTACTCTTTAACTTCGAACGGTTTGTTTTTCGCCTCTTTTGTCT
  L C F I S F S F N F S A L C F A S F V S
   F L F N F I L F Q L K G F L F R L F C I
    V F F Q F H S I S A Q W V F L P S F L H

* Q P G A D * N Y D Q T K R A Q V M I V
   D S Q E P I E I M I K R K E R K S * L *
    T A R S R L K L * S N E K S A S H D C K
TGACAGCCAGGAGCCGATTGAAATTATGATCAAACGAAAAGAGCGCAAGTCATGATTGTA
      2290      2300      2310      2320      2330      2340
ACTGTCGGTCCTCGGCTAACTTTAATACTAGTTTGCTTTTCTCGCGTTCAGTACTAACAT
  S L W S G I S I I I L R F S R L D H N Y
   V A L L R N F N H D F S F L A L * S Q L
    C G P A S Q F * S * V F L A C T M I T F

K E I N P H F E D Y V F N W E Q T Y Q F
   K K S T L I S K I T C S I G S R R T S F
    R N Q P S F R R L R V Q L G A D V P V S
AAAGAAATCAACCCTCATTTCGAAGATTACGTGTTCAATTGGGAGCAGACGTACCAGTTT
      2350      2360      2370      2380      2390      2400
TTTCTTTAGTTGGGAGTAAAGCTTCTAATGCACAAGTTAACCCTCGTCTGCATGGTCAAA
  F F D V R M E F I V H E I P L L R V L K
   L F * G E N R L N R T * N P A S T G T E
    S I L G * K S S * T N L Q S C V Y W N R

L V G G Y G S S K S Y H T A L K I V L K
   L S A A T A H P K A I I P H * K S C * S
    C R R L R L I Q K L S Y R I E N R A K A
CTTGTCGGCGGCTACGGCTCATCCAAAAGCTATCATACCGCATTGAAAATCGTGCTAAAG
      2410      2420      2430      2440      2450      2460
GAACAGCCGCCGATGCCGAGTAGGTTTTCGATAGTATGGCGTAACTTTTAGCACGATTTC
  K D A A V A * G F A I M G C Q F D H * L
   Q R R S R S M W F S D Y R M S F R A L A
    T P P * P E D L L * * V A N F I T S F S

L L K E K R T A L V I R E V F D T H R D
   C * R K N G R P L * S G R C S I P I G I
    A E G K T D G P C D P G G V R Y P S G F
CTGCTGAAGGAAAAACGGACGGCCCTTGTGATCCGGGAGGTGTTCGATACCCATCGGGAT
      2470      2480      2490      2500      2510      2520
GACGACTTCCTTTTTTGCCTGCCGGGAACACTAGGCCCTCCACAAGCTATGGGTAGCCCTA
  Q Q L F F P R G K H D P L H E I G M P I
   A S P F V S P G Q S G P P T R Y G D P N
    S F S F R V A R T I R S T N S V W R S E
```

FIG. 15g

```
        S T F A L F Q E V I E E L
         R P S P C F K R * S K S S
          D L R L V S R G D R R A -
       TCGACCTTCGCCTTGTTTCAAGAGGTGATCGAAGAGCTC
           2530      2540      2550
       AGCTGGAAGCGGAACAAAGTTCTCCACTAGCTTCTCGAG
          R G E G Q K L L H D F L E
         S R R R T E L P S R L A -
        V K A K N * S T I S S S -
```

GENE EXPRESSION SYSTEM

This application is a continuation application of application Ser. No. 07/961,718, filed as PCT/DK91/00074, Mar. 11, 1991, now abandoned.

This invention relates to expression systems which are suitable for use in a Gram positive bacterium, particularly Bacillus species.

The ability of cells to produce non-infectious phage-like particles is a widespread occurrence throughout bacterial species. Many of these particles have been noted for their bacteriocidal properties (6, 14, 25, 47). Included in this category are the related defective phages of *Bacillus subtilis*, PBSW, PBSX, PBSY and PBSZ, which are resident as prophages on the chromosomes of *B. subtilis* var. vulgatus and *B. subtilis* strains 168, S31 and W23 respectively (44, 46), and PBSV found in *B. licheniformis* (23). Morphologically PBSX and related defective phage particles differ in tail length and in the number of cross-striations in the tail (44). The phage particles do not contain a complete phage genome and hence are unable to infect any known host (2, 19, 33, 34, 45). Defective phages of similar morphology and serologically related to PBSX, are also produced by all analysed strains of *B.amyloliquefaciens* and *B.pumulis*. (23, 44). It has been suggested that the phages may have evolved from a common ancestral prophage, lysogenic in a common bacterial ancestor (46).

The widespread occurrence of the PBSX-like defective phages throughout these Bacillus species, and the failure to isolate strains cured of PBSX, suggests that their continued maintenance is advantageous, if not essential for the host strain (5, 16, 46). One possible ecological advantage that these phages confer upon the host cell is the ability to adsorb to and kill cells containing a heterologous, but not the homologous, phage (44, 46). In these respects these phages appear to share characteristics of both temperate bacteriophages and bacteriocins (33, 4).

Of these phages, PBSX has been the most extensively studied. Mutations in both regulatory elements, and in genes involved inparticle morphogenesis map between metA and metC on the *B. subtilis* 168 chromosome (4, 15, 16). Upon induction, replication of the phage genome extends into the host chromosome as seen by the 5–10 fold enrichment of genetic markers in the vicinity of the PBSX prophage (2, 16, 49). The phage particle, which consists of a small head and long contractile tail is composed of at least 26 polypeptides (29). A further 7 PBSX specific proteins have been identified in induced cells, leading to an estimation of the genome size of approximately 54 kb. (29). However, the phage packages DNA fragments of only 13 kb. in length which is derived largely and apparently randomly from the host chromosome (2, 18, 33, 34). Although the phage particle adsorbs to the cell wall of a sensitive cell, this DNA is not injected (33). Thus a combination of factors appears to contribute to the defective nature of this phage.

These phage-like particles have generally been referred to as "defective prophages". However, they have lost the ability to act as phages and in some respects are very similar to bacteriocins. They have, therefore, sometimes been referred to as "particulate bacteriocins". The distinctions between bacteriocins, defective phages and particulate bacteriocins have not been clearly drawn in the literature and for this reason the present inventors have suggested the use of the term "phage-like bacteriocins" or "phibacins" to denote non-infectious, phage-like particles which otherwise have the properties of bacteriocins. The term phibacin is also used to describe the phibacin genome as appropriate in the text.

According to the present invention there is provided an expression system comprising a phibacin or a mutant thereof, or a gene or a mutant gene of a phibacin having a function in gene expression. The phibacin may be a phibacin isolated from Bacillus species, particularly from *Bacillus subtilis*. The phibacin may be selected from the phibacins PBSW, PBSX, PBSY and PBSZ of *Bacillus subtilis*.

In particular the invention relates to an expression system comprising the phibacin deposited with the National Collection of Industrial Bacteria, Torry Research Station, Aberdeen, Scotland, on 6th Sep., 1989 under the accession no. NCIMB 40205, isogenic derivatives thereof, and phibacins which are substantially similar thereto, particularly phibacins having at least 50% homology therewith, the said derivatives and similar phibacins having a function in gene expression.

Particularly preferred are expression systems comprising mutants of the phibacins which do not lyse the host cell on induction. Such mutants may be created by insertional mutagenesis. In particular the phibacin may carry the xhi1479 mutation. The expression system may comprise the mutant phibacin deposited with the National Collection of Industrial Bacteria, Torry Research Station, Aberdeen, Scotland, on 6th Sep., 1989 under the accession no. NCIMB 40206, isogenic derivatives thereof and phibacins which are substantially similar thereto, particularly phibacins having at least 50% homology therewith, the said derivatives and similar phibacins having a function in gene expression and being non-lysogenic on induction.

The invention also provides an expression system comprising a repressor gene, a promotor and at least one operator, isolated from a phibacin. The repressor gene may be the orf1 gene encoded by the phibacin PBSX. The repressor gene may have the DNA sequence shown in FIG. 8, (SEQ ID NO. 1)or a sequence which is substantially similar thereto, particularly a sequence having at least 50% homology therewith, and encoding repressor activity. The promotor may have the DNA sequence shown in FIG. 8, or a DNA sequence substantially similar thereto, particularly a sequence having at least 50% homology therewith, and encoding promotor activity. The operator may have the sequence of any one of the operators 01, 02 and 03 shown in FIG. 8, or a DNA sequence substantially similar thereto, particularly a sequence having at least 50% homology therewith, and encoding operator activity.

The expression system may further comprise a gene encoding a positive control factor isolated from a phibacin. The positive control factor-encoding gene may be the orf2 gene encoded by the phibacin PBSX. The positive control factor-encoding gene may have the sequence shown in FIG. 15, or a sequence which is substantially similar thereto, particularly a sequence having at least 50% homology therewith and encoding positive control factor activity.

Advantageously, the expression system comprises a gene encoding a temperature-sensitive repressor so that product expression is heat-inducible. The gene encoding the temperature-sensitive repressor may be the xhi1479 allele of orf1. The temperature-sensitive repressor may have the DNA sequence shown in FIG. 9, (SEQ ID NOS. 3 and 5) or a sequence which is substantially similar thereto, particularly a sequence having at least 50% homology therewith, and encoding temperature-sensitive repressor activity.

In a further aspect the invention provides a repressor gene isolated from a phibacin, particularly from PBSX, and genes which are substantially similar thereto, particularly genes having at least 50% homology therewith, and encoding repressor activity. The repressor gene may be the orf1 gene of PBSX. In particular the invention provides a repressor gene having the DNA sequence shown in FIG. 8 or a sequence which is substantially similar thereto, particularly a sequence being at least 50% homologous therewith, and the said gene encoding repressor activity. An example of a repressor gene is contained in the phibacin which was deposited with the National Collection of Industrial Bacteria, Torry Research Station, Aberdeen, Scotland on 6th Sep., 1989 under the accession no. NCIMB 40205.

The invention also provides a temperature-sensitive repressor gene isolated from a phibacin, particularly from PBSX, and genes which are substantially similar thereto, particularly genes having at least 50% homology therewith, and encoding temperature-sensitive repressor activity. The temperature-sensitive repressor gene may be the xhi1479 allele of the orf1 gene of PBSX. In particular the temperature-sensitive repressor gene may have the sequence shown in FIG. 9 (SEQ ID NOS. 3 and 5), or a sequence which is substantially similar thereto, particularly a sequence having at least 50% homology therewith, the said sequence encoding temperature-sensitive repressor activity. An example of a temperature-sensitive repressor gene is contained in the mutant phibacin which was deposited with the National Collection of Industrial Bacteria, Torry Research Station, Aberdeen, Scotland on 6th Sep. 1989 under the accession no. NCIMB 40206.

In a still further aspect the invention provides a gene encoding a positive control factor isolated from a phibacin, particularly PBSX, and genes which are substantially similar thereto, particularly genes having at least 50% homology therewith and encoding positive control factor activity. In particular the invention provides a repressor gene having the DNA sequence shown in FIG. 15 (SEQ ID NO 10–17) or a sequence which is substantially similar thereto, particularly a sequence being at least 50% homologous therewith, and the said gene encoding positive control factor activity. An example of a positive control factor gene is contained in the phibacins which were deposited with the National Collection of Industrial Bacteria, Torry Research Station, Aberdeen, Scotland on 6th Sep., 1989 under the accession nos. NCIMB 40205 and NCIMB 40206.

The invention also relates to bacterial hosts containing one or more of the expression systems or genes as defined above. The invention also provides plasmids carrying one or more of the genes defined above.

The invention also provides all of the above materials in biologically pure or isolated form.

The invention therefore provides a method of producing a gene product in which the gene in question is inserted into an expression system as defined above and the expression system is introduced into a bacterial host to express the gene product. This method is suitable for producing proteins in Gram positive bacteria.

Also provided is a method of integrating a gene into a bacterial chromosome in which a segment of phibacin DNA is inserted into a plasmid carrying the desired gene, the plasmid is introduced into a bacterial cell carrying on the chromosome at least a portion of phibacin DNA having the same or a substantially similar DNA sequence as that of the phibacin DNA segment contained on the plasmid, and recombination events between the plasmid and the phibacin DNA in the bacterial chromosome, which integrate the desired gene into the chromosome, are selected for by methods known in the art. Any segment of phibacin DNA would be suitable to drive integration.

The term "expression system" as used herein includes vehicles or vectors for the expression of a gene in a host cell as well as vehicles or vectors which bring about stable integration of a gene into the host chromosome.

The term "substantially similar" as used herein means sequences which have sufficient sequence identity or homology to the deposited phibacins, or genes contained in the deposited phibacin to hybridize therewith and to retain a function in gene expression, or phibicin or gene activity.

The advantage of using an expression system effective in Bacillus strains is that Bacillus is an effective secretor of proteins and using the system it would be possible to substitute Bacillus for *E. coli* or yeasts in processes for the production of genetically-engineered proteins to get an enhanced secretion of the protein in question. Bacillus strains are also "Generally Recognised As Safe" or are "GRAS" micro-organisms. Bacillus has long been used in the food and drink industry and in the production of antibiotics. It has the advantage that it does not contain pyrogenic substances or produce toxins. There is extensive industrial experience of using Bacillus in fermentations such as in the production of detergent proteases and alpha-amylase. It is also more difficult to use proteins made in *E. coli* in the food industry since this organism is not considered to be safe. Further advantages of the expression vehicles disclosed above are that there are strong ribosome binding sites and promoters linked to these phibacins, particularly PBSX, which further enhance protein production. In addition, the phibacins disclosed above have the advantage that they are stably integrated into the bacterial chromosome.

By using an expression system which is heat-inducible it is possible to grow host cells to a high cell density and then to shift the temperature to induce expression of the gene and protein production. The expression of the product can thus be achieved in a short period of time. A further advantage of this system is that simultaneously with heat-induced expression of the product, it is possible to get heat-induced amplification of the expression system thus amplifying the gene(s) encoding the product in question which in turn can substantially increase production of the product.

One embodiment of the present invention ultilizing PBSX will now be described with reference to the accompanying drawings in which:

FIG. 1. Map of the integrating vector, pWD3, constructed as described in Materials and Methods. The $Cm^r$ gene from pBD64 was subcloned into the multiple cloning site of pUC18. This was followed by insertion of the promoterless alpha-amylase gene, isolated from pSL5 (36). The resulting plasmid contains unique restrictions sites for EcoR1, Sac1, Sma1 and BamH1 immediately 5' to the promoterless alpha-amylase gene.

Figure 2:
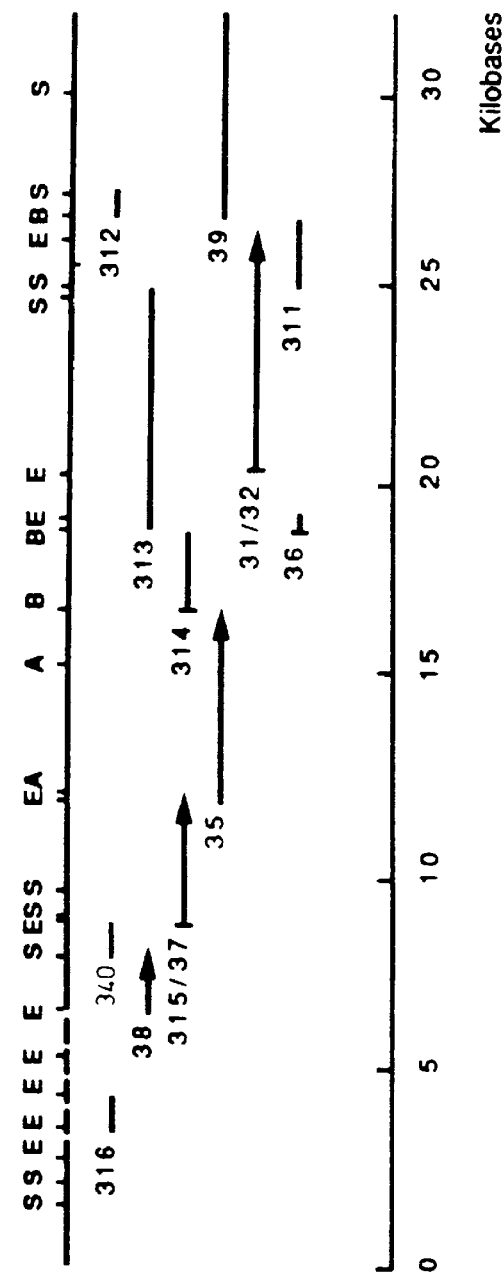
Figure 3A:
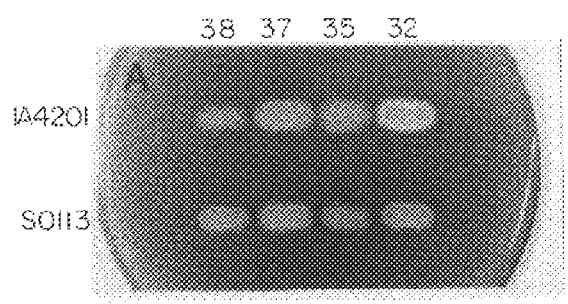
Figure 3B:
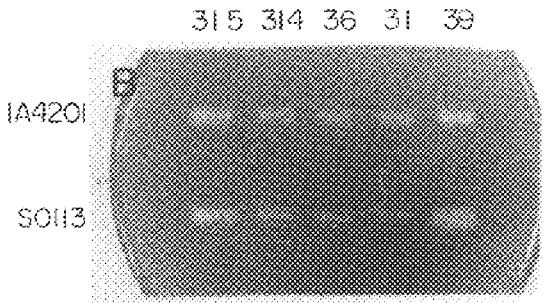
Figure 3C:
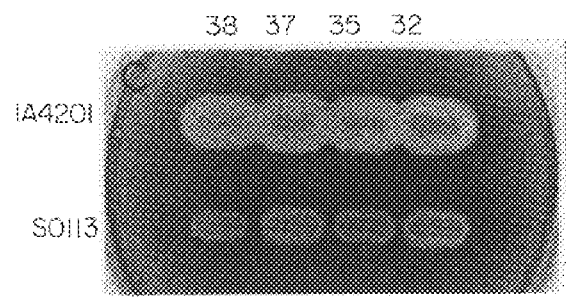
Figure 3D:
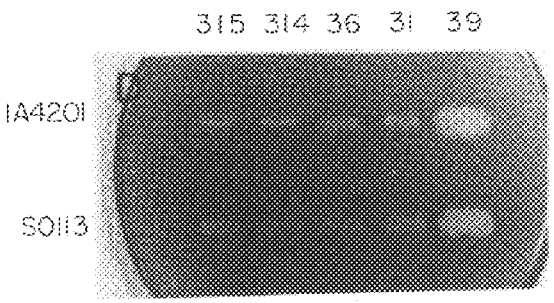

FIG. 2. Restriction map of the 33 kb. cloned region of PBSX. Fragments used to direct integration of pWD3 are indicated below. Where known, the fragment end which is fused to the promoterless alpha-amylase gene is indicated by a symbol: (→), transcription proceeds in direction of arrow; (↦), no transcription in this direction (see FIG. 3). Restriction sites: B, BamH1; E,EcoR1; S, Sac1; A,Sal1.

FIG. 3. Plate tests demonstrating thermoinducible production of alpha-amylase when integrated in one orientation into the chromosome of strain 1A4201 at the PBSX locus. Plates A and C show strains with the alpha-amylase gene integrated in the direction metA–metC. Plates B and D show strains with the alpha-amylase gene integrated in the direction metC–metA (see FIG. 2). Colonies were grown on LB agar containing starch, at 30° C. for 18 hours (plates A and B), or at 30° C. for 12 hours followed by 48° C. for 6 hours (plates C and D). Plates were subsequently stained with iodine.

Figure 4:
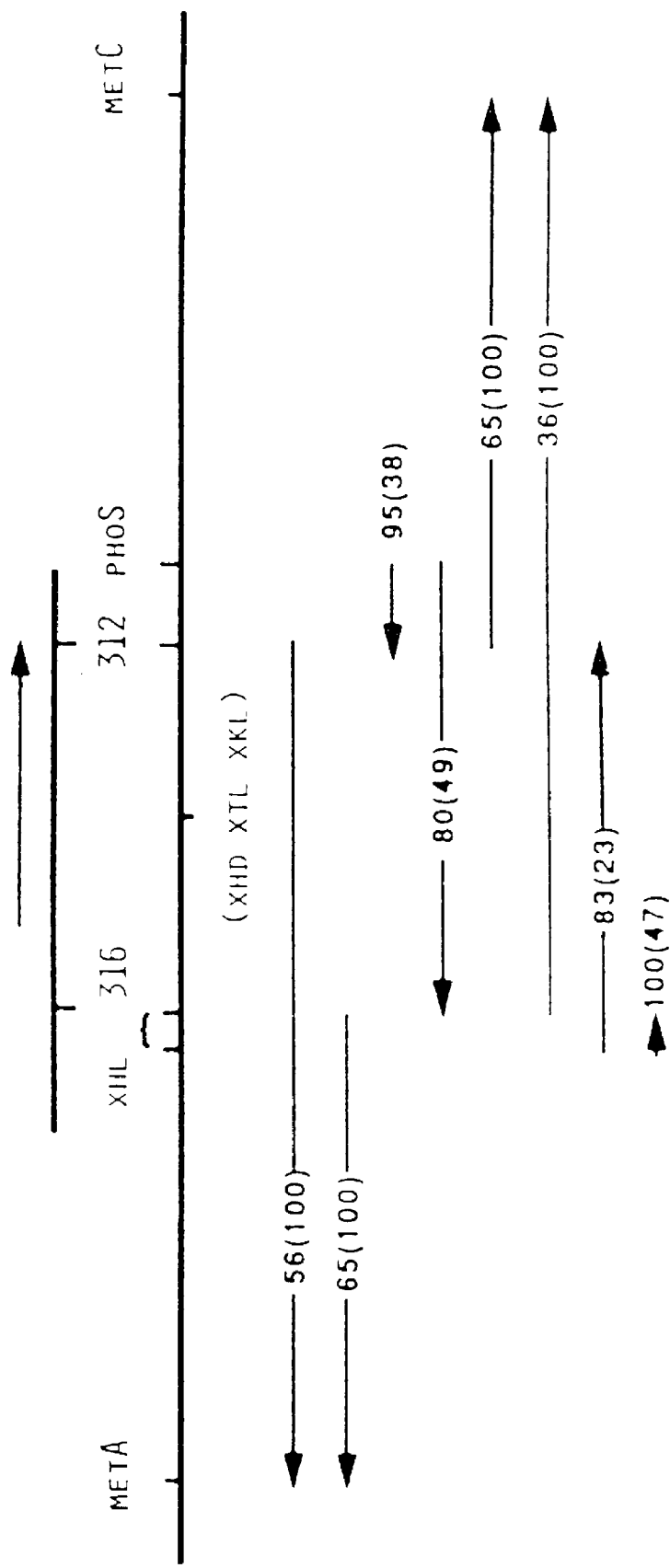

FIG. 4. Linkage of the Cm$^r$ gene to the xhi1479 locus and adjacent chromosomal markers in two integrative strains: lA4201::pWD316 and lA4201::pWD312. Values are presented as percentage co-transduction using PBS-1. Numbers of transductants tested are given in parenthesis. The arrows point towards the selected marker in each case.

Figure 5:
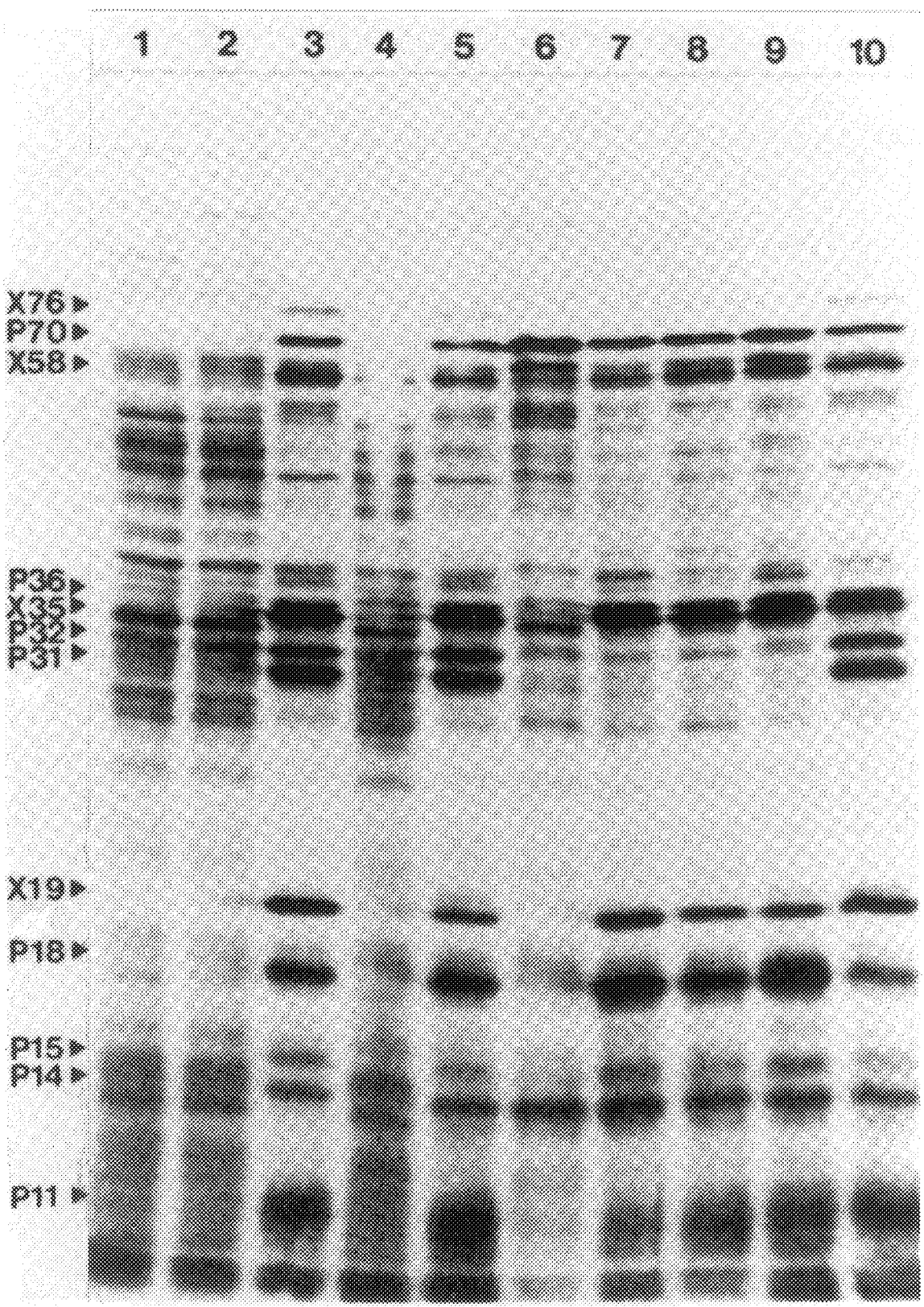

FIG. 5. One dimensional SDS-polyacrylamide gel (12.5%), of [$^{35}$S]-methionine labelled proteins from *B. subtilis* parental (L8508) and integrative strains. PBSX proteins were induced by a shift in growth temperature to 48° C. as described in Materials and Methods. The strains and growth temperature at which the labelling was carried out are as follows: lane 1: L8508 (37° C.). 2: L8508 xhi$^+$ (48° C.). 3: L8508 (48° C.). 4: L8508::pWD316 (48° C.). 5:

L8508::pWD38 (48° C.). 6: L8508::pWD37 (48° C). 7: L8508::pWD35 (48° C.), 8: L8508::pWD32 (48° C.). 9: L8508::pWD312 (48° C.). 10: L8508::pWD39 (48° C.). PBSX proteins are labelled according to the nomenclature of Mauel and Karamata (1984),(29), where X denotes a PBSX structural protein and P denotes a protein found only in cells induced for PBSX.

Figure 6:
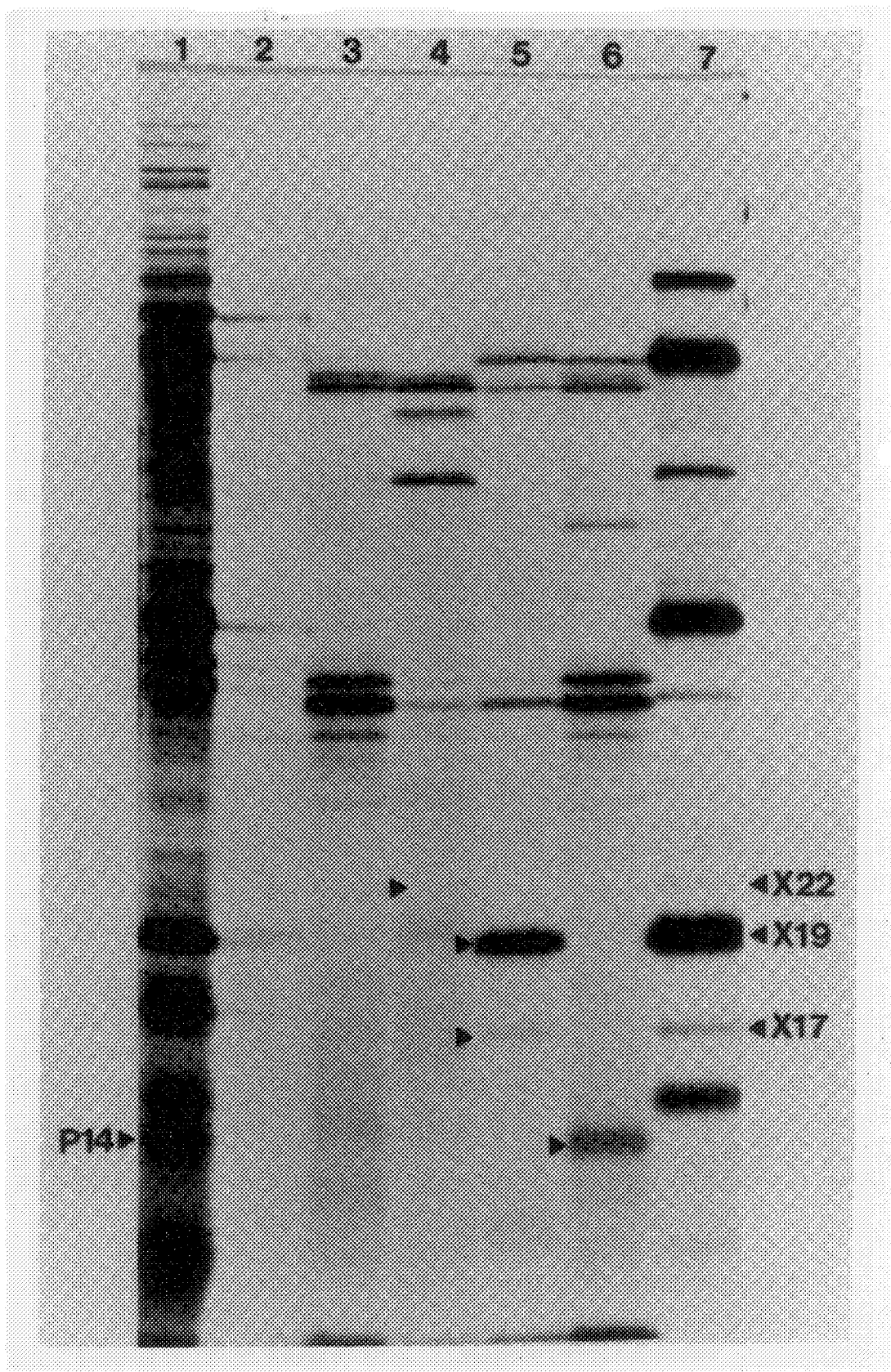

FIG. 6. One dimensional SDS-polyacrylamide gel (12.5%) of [$^{35}$S]-methionine labelled proteins from *E coli* maxicells. Lane 1: *B. subtilis* L8508 (48° C.), 2: *E. coli* CSR603, 3: *E. coli* CSR603/pWD3, 4: CSR603/pWD32 5: CSR603/pWD35, 6: CSR603/pWD37, 7: PBSX phage particle proteins. Proteins corresponding in size to PBSX proteins are indicated with arrows. Nomenclature is as in FIG. 5.

The protein labelled X22 may correspond to protein X22 or X21 described by Mauel and Karamata (29).

Figure 7:
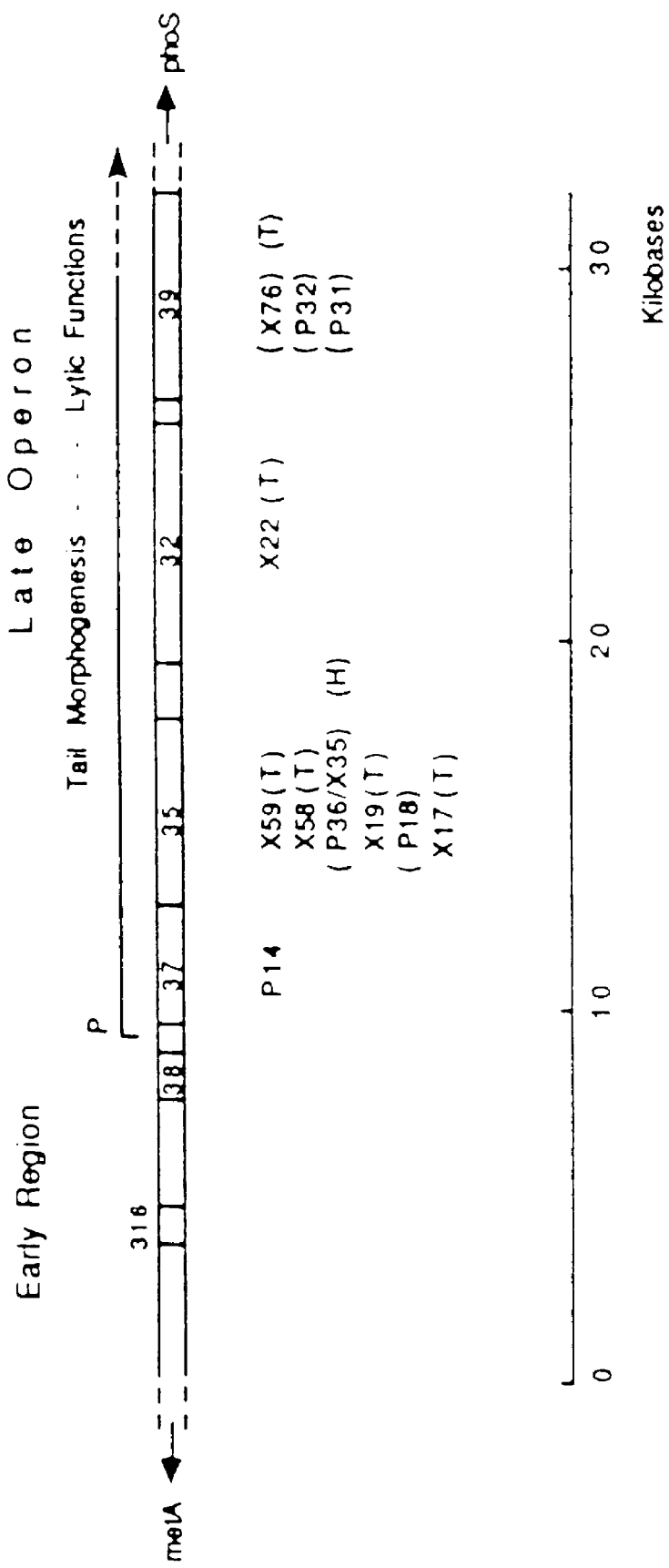

FIG. 7. Diagramatic representation of the functions of the cloned PBSX DNA as determined in this study. The early region is defined by integration of pWD316 which abolishes induction of any detectable PBSX proteins. The late operon is so called by analogy with other bacteriophage genomes; it encodes largely phage structural proteins. The proteins encoded by each region are indicated below. Parentheses indicate that the position of these genes is tentative, based only on the analysis of integrative strains. The allocation of other genes has been confirmed by analysis in *E. coli* maxicells. (H): Phage head protein; (T): Phage tail protein (29).

FIG. 8(SEQ ID NO. 1). Sequence of a segment of PBSX DNA showing the repressor gene orf1 and three putative operators, 01, 02 and 03. The figure also shows putative promoters and ribosome binding site (rbs). The putative operator recognition sequence is also shown.

FIG. 9(SEQ ID NOS. 3 and 5). Sequence including the region of DNA encoding the xhi1479 allele of orf1 isolated from the heat-inducible strain 1A4201. Where this differs from the wild-type sequence, the wild-type nucleotide has been indicated below.

Figure 10:
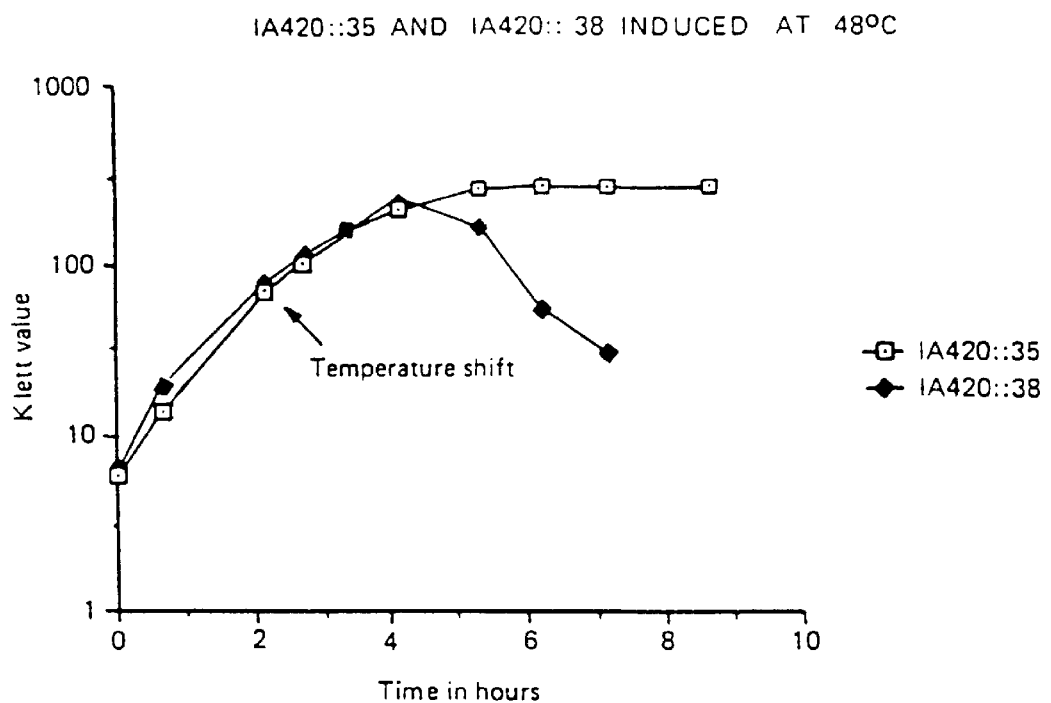

FIG. 10. The lysis negative phenotype observed upon integration of pWD35 compared to wild type lysis proficient phenotype generated upon integration of pWD38. The plasmids carry a promoterless gene for heat stable alpha amylase (HT alpha amylase) from *Bacillus licheniformis* (37,36).

Figure 11:
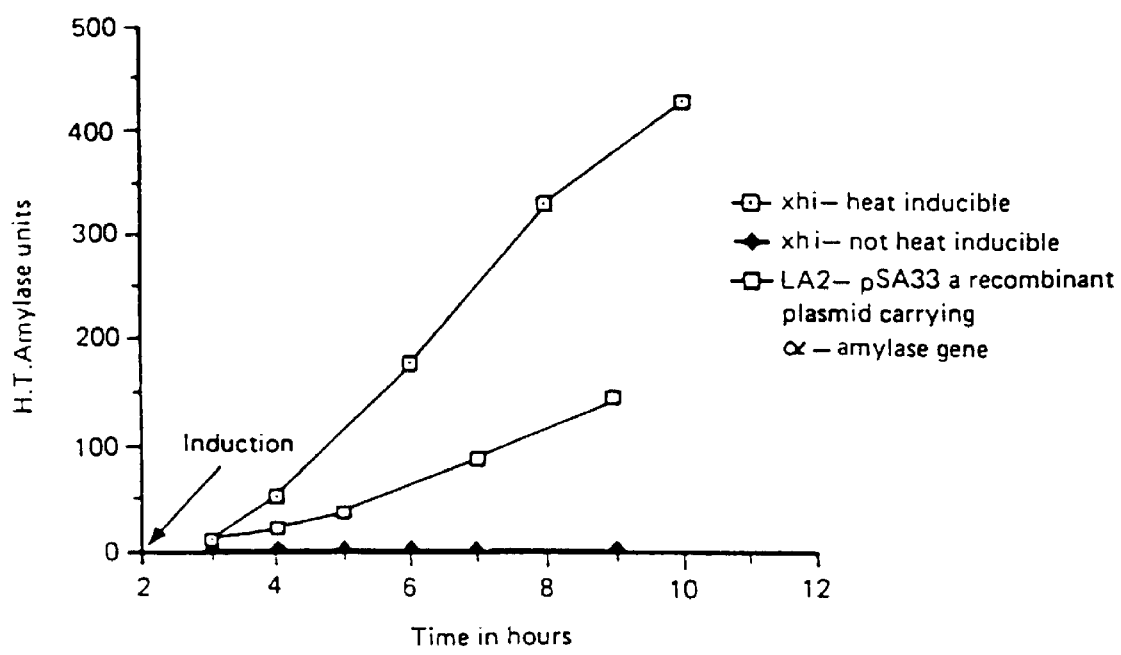

FIG. 11. The heat inducible expression of the gene for heat stable *Bacillus licheniformis* alpha amylase after heat induction of PBSX in 1A420:pWD35 and comparison with a non-inducible strain and a strain harbouring a multicopy recombinant plasmid pSA33 containing the same alpha amylase gene.

Figure 12A:
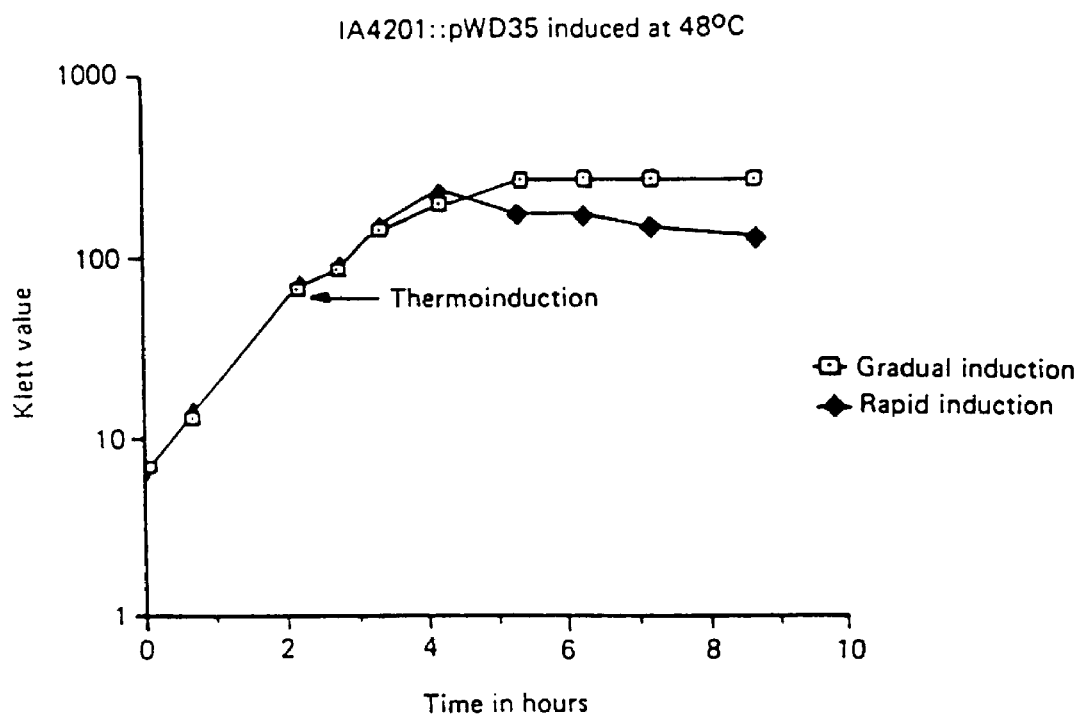

FIG. 12a. Growth curves of IA4201::pWD35 thermoinduced rapidly or gradually.

Figure 12B:
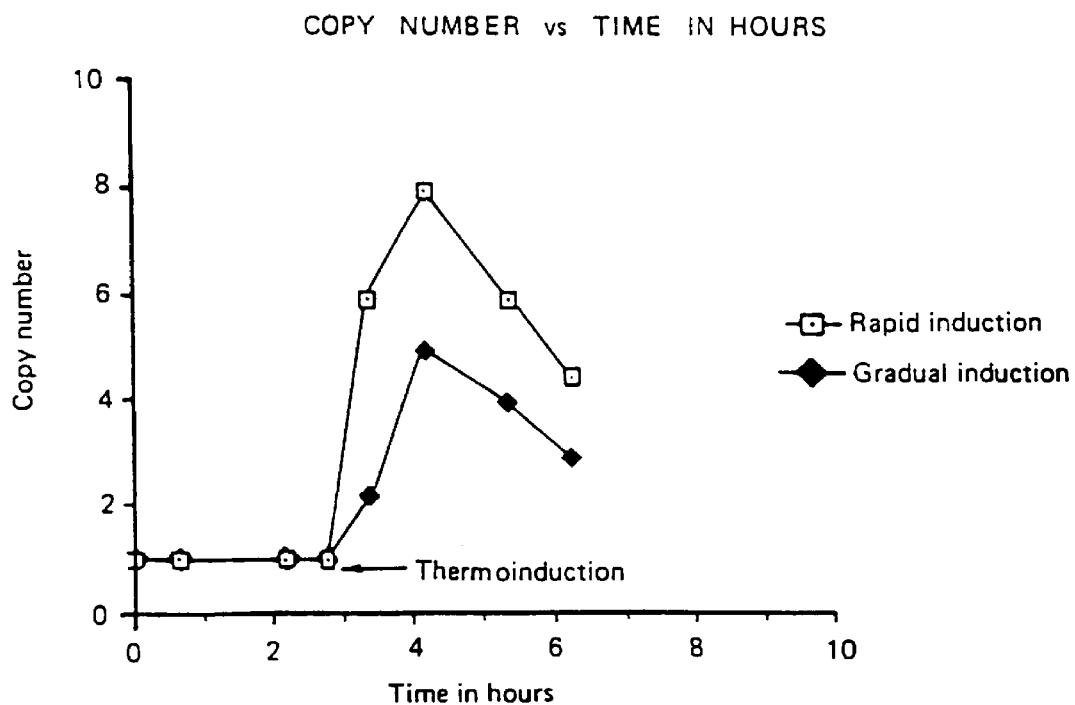

FIG. 12b. Copy number of the CAT gene relative to the β-glucanase gene as a function of time, on both rapid and gradual induction showing that an increase in the copy number of genes integrated in the PBSX genome takes place on heat induction.

Figure 13:
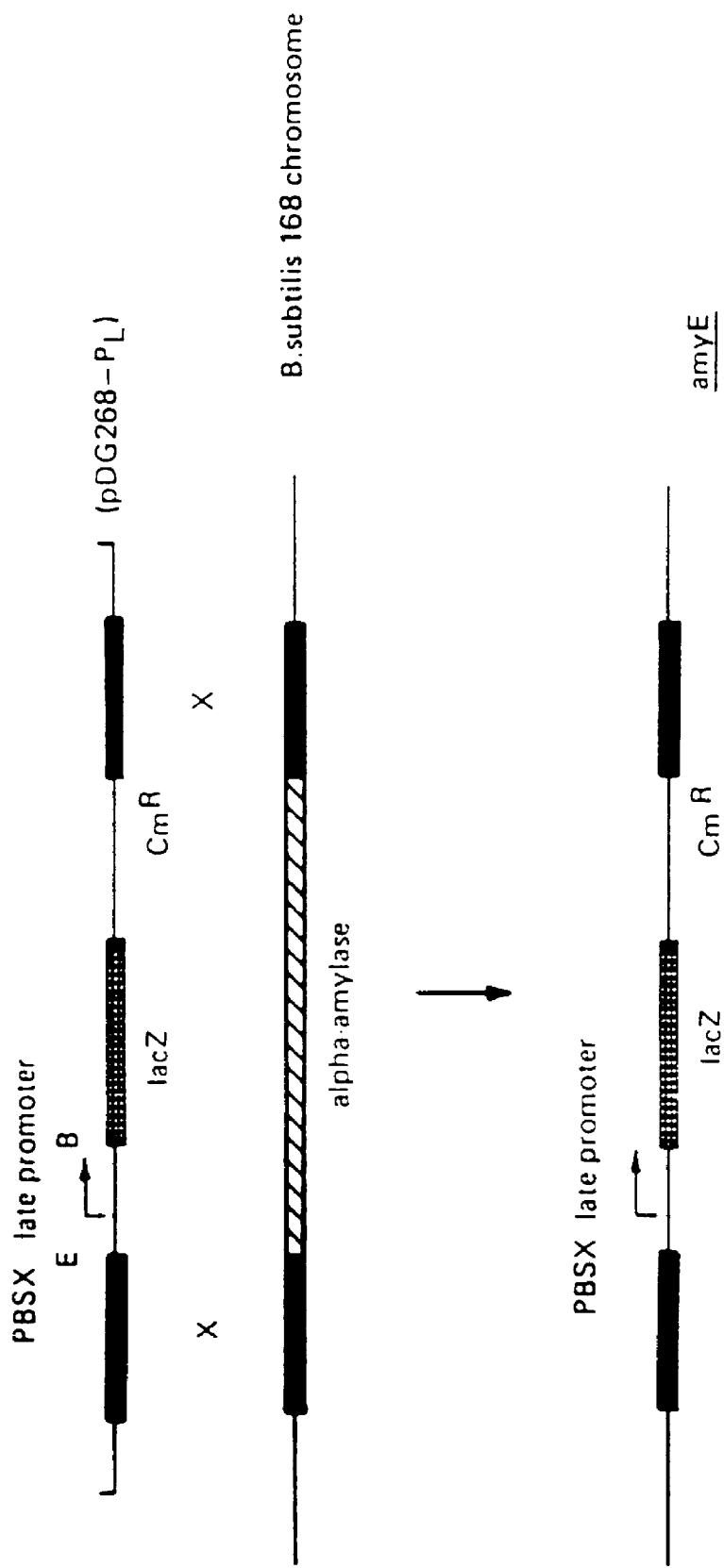

FIG. 13. Construction of the PBSX late promoter-lacZ transcriptional fusion. The 1.3 kb EcoR1–BamH1 fragment which contains the late promoter was ligated to EcoR1–BamH1 cut pDG268. The resulting plasmid was linearised using XbaI before transformation of *B. subtilis*. Alpha-amylase negative transformants were used for subsequent experiments.

Figure 14A:
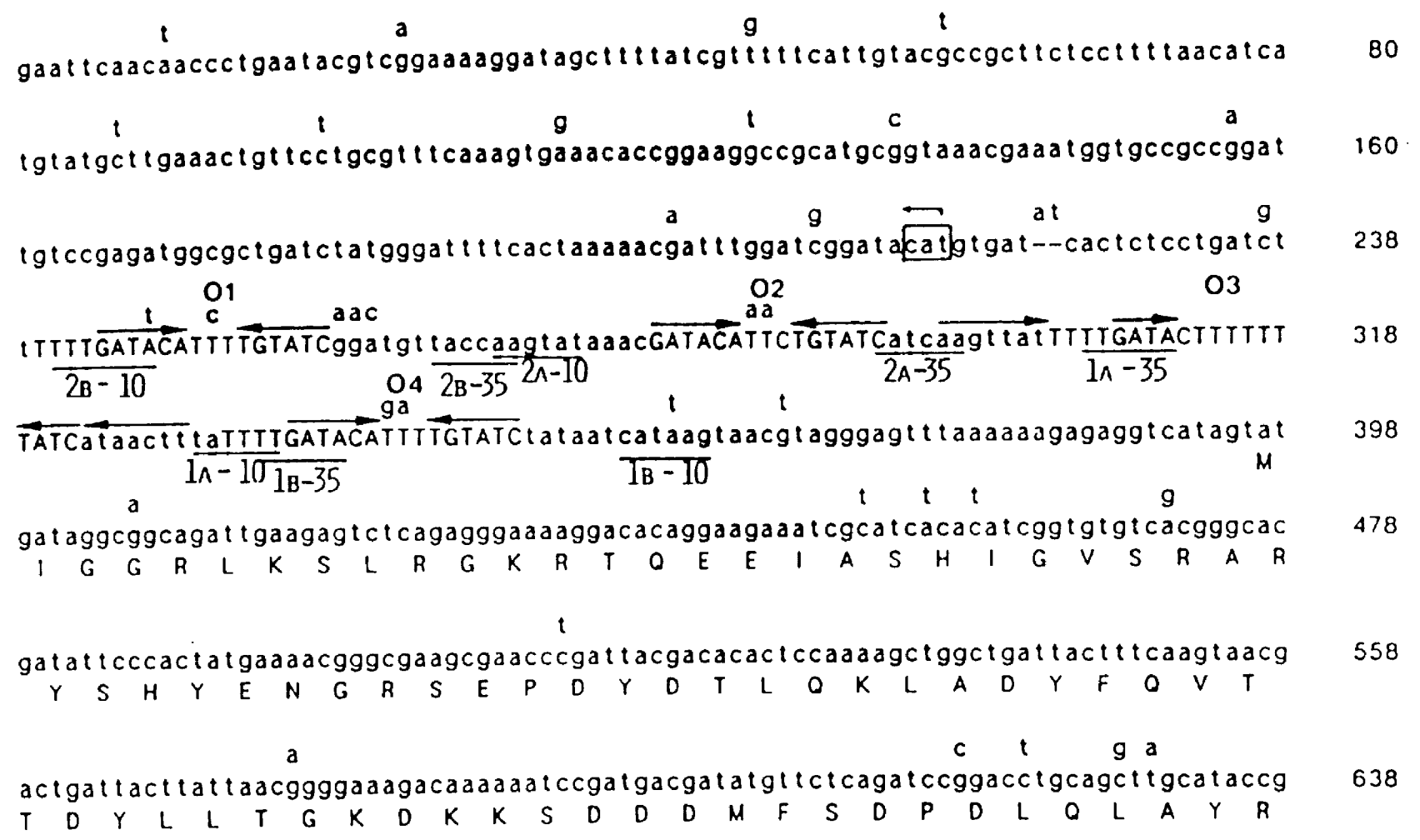

FIG. 14. Restriction digests of recombinant plasmids which encode the factor required for transcription from the late promoter. DNA from the PBSX early region was digested with HindIII and cloned into the HindIII site of pEB112. Plasmids were isolated from four β-galactosidase producing transformants (plasmids 1–4), and transformed into *E. coli*. Plasmid DNA from the *E. coli* transformants was digested with HindIII and restriction fragments separated on an agarose gel. Lanes 1 & 2: plasmid 1; lanes 3 & 4: plasmid 2; lanes 5 & 6: plasmid 3; lane 7: plasmid 4; lane 8: 1 kb size ladder.

FIG. 14(SEQ ID NOS 7–9). Nucleotide sequence of the 1.2-kb fragment which complements the xhi1479 mutation. Differences in the nucleotide sequence which occur in the temperature-inducible strain, IA4201, are indicated above the sequence. The amino-acid sequence of Xre is indicated. Start codons for other potential reading frames are boxed. Direct repeats 01, 02, 03 and 04 are indicated in upper-case letters, while inverted repeats are indicated with facing arrows above the nucleotide sequence. −35 and −10 consensus sequences for possible promoters for transcription of xre (1a and 1b), and diverging transcription (2a and 2b), are underlined. The nucleotide sequence was determined by the method of Sanger et al.(44). These nucleotide sequences have been submitted to Gen Bank with accession Nos. M36478 and M36477.

FIG. 15(SEQ ID NOS; 10–185). Sequence from the left-hand end of the 1.5 kb HindIII fragment to the right hand end of fragment 38. The putative amino-acid sequences in each of the three possible reading frames is also shown in conventional abbrevation.

Figures 15H, 16:
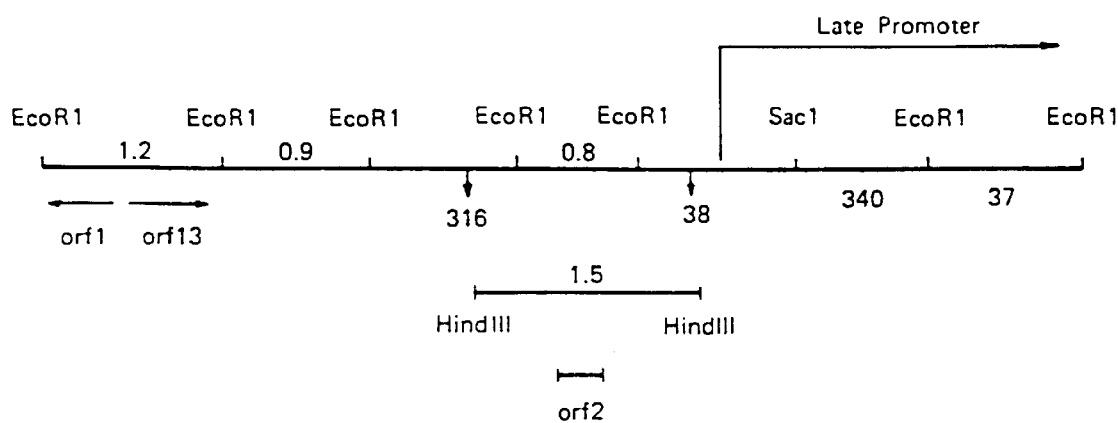

FIG. 16. Diagramatic representation of the early region of PBSX, not drawn to scale.

Table 1: Bacterial strains, plasmids and bacteriophage (BGSC: Bacillus Genetic Stock Center).

Table 2: Mutagenic properties of the indicated plasmids when integrated into *B. subtilis* L8508. Presence or absence of killing of induced cells on a lawn of *B. subtilis* W23. Presence or absence of cell lysis was determined by monitoring optical density.

Table 3: Presence or absence of the major PBSX induced proteins in cells containing the indicated integrated plasmids. Data are accumulated from 10% and 13.5% SDS-polyacrylamide gels.

Table 4: Bacterial strains and plasmids used in assessment of positive control factor.

Table 5: β-galactosidase production in late promoter-lacZ fusion strains in the presence or absence of mitomycin C(MMC).

MATERIALS AND METHODS
Bacterial Strains, Plasmids and Phases

Bacterial strains, plasmids and phages are listed in table 1. *B. subtilis* IA4201 was derived by congression, using DNA from strain S0113 to transform IA420. PurA$^+$colonies were selected and screened for acquisition of the amy-3 mutation. The construction of the integrating vector is shown in FIG. 1. The chloramphenicol acetyl-transferase gene was removed from pBD64 on a 1.1 kb. HpaII fragment. This was treated with Klenow fragment and ligated to EcoRI and Kenlow treated pUC18. The promoterless alpha-amylase gene (36, 37) was removed from pSL5 on a BamHI–HindIII and inserted between the BamHI–HindIII sites. The EcoRI site distal to the alpha-amylase gene in the resulting plasmid was removed by a partial EcoRI digestion, treatment with Klenow fragment, followed by religation. The resulting plasmid pWD3 contains unique restriction sites for EcoRI, SacI, SmaI and BamHI immediately 5' to the promoterless alpha-amylase gene.

Enzymes, Chemicals and Materials

Restriction enzymes, Klenow fragment and T4 DNA ligase were purchased from Boehinger Mannheim Biochemicals (Indianapolis Ind.). Nick translations were performed using an Amersham kit N5500. [$^{32}$P]dCTP and L-[$^{35}$S] methionine were also obtained from Amersham (Amersham Corp. Arlington Heights, Ill.). Acrylamide, ammonium persulphate and N,N,N',N'-tetramethylenediamine were obtained from BDH Chemicals Ltd. (Poole, England). N,N'-methylbisacrylamide was purchased from Sigma Chemical Co. (St. Louis, Mo.). En³Hance autoradiography enhancer was obtained from New England Nuclear Corp. (Boston Mass.). X-ray film (RX) was from Fuji; X-ray developer (LX-24) and fixer (FX-40) from Eastman Kodak Co. (Rochester, N.Y.).

Construction and Screening of a B. subtilis 168 Chromosomal Bank

Chromosomal DNA from B. subtilis S0113 was partially digested with Sau3A and size fractionated on a sucrose gradient. Fragments of 14–22 kb. were pooled and ligated to lambda EMBL3 digested with BamHI in a vector to insert ratio of 3:1. Recombinant plaques were selected on a lawn of E. coli Nm539. Plaques were lifted onto a Pall Biodyne nylon membrane (Pall Corp., Glen Cove, N.Y.), and hybridised according to the manufacturer's instructions.

Media

B. subtilis and E. coli were routinely grown on Luria broth or agar. When appropriate, media contained chloramphenicol (3 µg/ml) for selection in B. subtilis or ampicillin (50 µg/ml) for selection of plasmids in E. coli. Alpha-amylase activity was detected by adding starch (0.2%) to the media and subsequently staining the plates with a solution of 0.5% I$_2$, 1% Kl.

Transformation and Transduction

Transformation of E. coli and B. subtilis was carried out as described (9). PBS-1 transductions were performed as described (35). Transductants were selected either on media containing chloramphenicol, or on agar containing SS+0.4% glucose supplemented 20 with appropriate amino acids (0.005%), and nucleosides (0.01%) and sub-cultured to appropriate media to determine linkage. Alkaline phosphatase was assayed according to the plate test described (39).

Test of PBSX Killing Activity

PBSX killing activity was determined by spotting lysates unto a lawn of the sensitive strain B. subtilis W23 as previously described (4). When cell lysis did not occur after PBSX induction, cells were sonicated before spotting supernatants unto the lawn.

DNA Preparation

Small scale preparations of plasmid were obtained as described previously (3). Large scale plasmid preparations were further 35 purified by CsCl density gradient centrifugation (28).

Large and small scale preparations of lambda DNA were prepared using either liquid culture or plate lysates (28).

Radioactive Labelling of Proteins

PBSX structural proteins were labelled essentially by the method described (29), except that cells of strain L8508 were grown in SS+0.05% glucose at 37° C. Phage were induced at a cell density of 4×10$^7$ by shifting to 48° C. At 30 minutes after the temperature shift L-[$^{35}$S] methionine (15 µCi/ml) was added and lysis allowed to continue for 1.5 hours. Phage particles were purified over a CsCl gradient.

To label proteins in cells induced for PBSX, overnight cultures were diluted to a cell density of 6×10$^6$ in SS+0.05% glucose and grown to a cell density of 3×10$^7$. PBSX was induced by shifting the growth temperature to 48° C. At 30 min and 40 min post-induction 1ml aliquots were withdrawn and incubated with continued shaking in the presence of L-[$^{35}$S] methionine. After 5 min., cold methionine was added (0.33 ml of 50 mg/ml). Cell pellets were stored at −20° C. and processed for electrophoresis as described (31). Labelling of plasmid encoded proteins in E. coli was performed according to the method of Sancar et al. (41).

SDS-PAGE

Labelled proteins (10$^6$ cpm of each sample) were separated on 8%, 10% and 12.5% SDS-PAGs by the method described (26). A $^{14}$C methylated protein mixture (14.3 kD to 200 kD) was co-electrophoresed as molecular weight markers. Gels were treated with En³Hance according to the manufacturer's instructions, dried and autoradiographed for 12–48 hours.

RESULTS

Isolation of PBSX DNA

PBSX does not package its own genome (19, 34). Therefore, in order to isolate DNA coding for phage functions, a B. subtilis 168 chromosomal bank, (constructed in lambda EMBL3), was screened with pOK411C, a plasmid which was known to contain DNA from the PBSX prophage (36). By successive cycles of screening, approximately 33 kb. of DNA from the PBSX region of the chromosome were isolated in four overlapping lambda clones. A restriction map of the cloned region is presented in FIG. 2. Hybridisation of selected fragments to chromosomal DNA digests by Southern blotting (43), indicated that no rearrangements had occurred (data not shown).

Analysis of Transcriptional Activity within the Cloned Region

With a view to analysing the transcriptional activity across this region, the cloned DNA was used to direct integration of a promoterless alpha-amylase gene into the chromosome. A series of fragments were subcloned into the integrating vector pWD3, using unique restriction sites immediately 5' to the promoterless alpha-amylase gene (FIG. 2). Each plasmid was transformed into B. subtilis 1A4201, with selection for the acquisition of chloramphenicol resistance. In each of six cases checked, integration appeared to have occurred by a Campbell type mechanism, resulting in the plasmid sequences being flanked by direct repeats of the chromosomal DNA which directed integration (data not shown) (12, 36). Expression of the alpha-amylase gene in each of the fusion strains now provided a convenient method to assay transcriptional activity across the cloned DNA.

Four independent integrations, covering a distance of approximately 18 kb, showed low levels of alpha-amylase production when cells were grown at 30° C. Expression was increased when the growth temperature was shifted to 48° C., the temperature at which the prophage is induced in the xhi1479 background (4), (FIG. 3). However, when the alpha-amylase gene was integrated in the opposite orientation, little or no expression of the gene was observed at either growth temperature. Thus it appears that transcription of the prophage proceeds predominantly in one direction across at least 18 kb. The proportion of this induction that is attributable to gene amplification or increased transcription has not been estimated.

Position and Orientation of the Cloned DNA on the *B. subtilis* Chromosome

In order to establish the position of the cloned DNA on the chromosome and to determine its orientation, two strains with plasmids integrated at either extremity of the cloned region, 1A4201::pWD312 and 1A4201::pWD316 were used as donors and recipients in PBS-1 transduction. In each case the site of integration of thechloramphenicol resistance marker was mapped with respect to neighbouring chromosomal markers (FIG. 4). The chloramphenicol resistance marker in strain 1A4201::pWD312 was closely linked to phoS, a mutation which results in constitutive alkaline phosphatase expression (39). In strain 1A4201::pWD316 the chloramphenicol resistance gene had integrated close to the xhi1479 allele which confers the heat-inducible phenotype (4). The data suggest the order of markers as shown in FIG. 4. Although mapping studies were not carried out with respect to other PBSX markers, correlation with the known genetic map for this region suggests that the cloned DNA spans the sites of mutations within PBSX genes coding for head (xhd) and tail (xtl, xki) proteins (4, 15, 16).

The Cloned DNA is of PBSX Origin.

Thermo-induction of alpha-amylase expression in the fusion strains carrying the xhi1479 allele, together with the mapping data provided strong evidence that the cloned DNA was derived from the PBSX region of the chromosome, but did not exclude the possibility that much of the DNA could lie outside the PBSX genome itself. Indeed, replication of PBSX DNA is thought to extend into flanking host DNA (2, 16, 49). In order to distinguish between these possibilities the mutagenic properties of integrating plasmids were exploited: If integration is mediated by an internal fragment of an operon, then the integration event will disrupt functions of this operon (32, 40).

Production of PBSX particles can be detected by their bacteriocidal activity on a PBSX sensitive strain *B. subtilis* W23 (33,45,46). The plasmid pOK411C, isolated by O'Kane et al. (36), was shown to contain a fragment of PBSX origin by its ability when integrated to abolish this PBSX killing function. Each fragment as shown in FIG. 2 was used to direct integration of pWD3 into *B. subtilis* L8508, and the resulting strains tested for production of killing activity. Of 11 strains tested, 9 showed a marked reduction in killing activity when compared to that of the parental strain (table 2). (Residual killing activity in these strains may be due to a low level of transcriptional readthrough from the plasmid sequences, or to excision of the plasmid sequences in a sub population of cells).

Furthermore, the same integrant strains which showed reduced killing activity failed to show the characteristic pattern of PBSX induced cell lysis when grown in liquid media (table 2). These strains presumably resulted from integration events which disrupt a PBSX operon thus preventing production of factors required for killing activity and cell lysis.

Production of PBSX Proteins in Strains Containing Integrated Plasmids

At least 12 polypeptides under PBSX control have been identified in induced cells (19). The results presented in table 2 suggested that the full complement of PBSX proteins was not being produced in many of the integrant strains. To examine this in more detail, the proteins produced by a representative sample of integrant strains were radioactively labelled and separated by SDS-PAGE (FIG. 5). The accumulated data from 10% and 13% gels are summarised in table 3.

Fragment 316 is derived from the extreme left hand end of the map (FIG. 2). Strain L8508::pWD316 fails to show induction of any detectable phage proteins. Integration of plasmid pWD37 prevents the synthesis of a number of phage proteins, including a major head protein and its proposed precursor X35 and P36 (29), several tail proteins, X76 and X19, and non-structural proteins P32 and P31. Proteins P36/X35, X19 and P18 are observed in strains L8508::pWD35, L8508::pWD32 and L8508::pWD312, although these strains lack X76, P32 and P31. Strains L8508::pWD38 and pWD39 produce all detectable PBSX proteins, which is consistent with the non-mutagenic nature of integration directed by these two fragments.

Expression of Phage Proteins in *E. coli*

Integration of plasmids pWD37, pWD32, pWD35 and pWD312 prevented production of some, but not all of the phage structural proteins, which suggested that the respective fragments might be derived from a late operon of the prophage. In order to examine if these fragments contained the genes for any known phage proteins, plasmids pWD37, pWD32 and pWD35 were transformed into *E. coli* CSR603. Plasmid encoded proteins produced in maxi-cells were labelled and separated on 8% and 12.5% SDS-PAGs (FIG. 6). In the strain containing pWD35 proteins were observed which corresponded in size to previously identified phage proteins X58, X19 and P17. In addition this fragment encoded a protein which corresponded in size to a newly identified phage protein which we have named X59. It can be seen when phage particle proteins are separated on low percentage gels. Plasmid pWD32 encoded a protein which corresponded in size to a phage tail protein, (X22), while pWD37 gave rise to a protein which corresponded to P14, a protein of unknown function found in induced cells. Proteins X58 and X19 were produced in sufficient amounts to be subjected to limited proteolysis by the method of Cleveland (7). In each case peptides of similar size to those of the phage proteins were produced, thus confirming their identity (data not shown).

Generation of a Functional Map of the PBSX Prophage

The information obtained from the expression of proteins in the *B. subtilis* strains and from the expression of proteins in *E. coli* have been combined to create a functional map of the cloned region (FIG. 7). The early region of the prophage has been so called as the production of any detectable phage proteins is prevented by integration directed by fragment 316. This suggests an integration event into an operon whose expression is required for expression of all late phage genes. Furthermore, this fragment is closely linked to the xhi1479 allele which is presumably within the prophage repressor gene.

The late operon indicated is thought to be at least 18 kb in length. The restriction map suggests that fragments within the region 8 kb to 26 kb direct mutagenic integration, indicating that each is derived from an internal part of an operon. If these fragments are contiguous, as the restriction map suggests, then these fragments must be derived from the one operon. Within this proposed operon, genes have been assigned to regions based on the assumption that in each strain transcription will proceed only to the end of the fragment which directs integration in each case, i.e. the 3' end of the operon, downstream from the integrated plasmid sequences in each case will not be transcribed. Thus, a protein absent in one integrant strain, but present in a strain containing the plasmid integrated further downstream, can be assigned to the intervening region. (e.g. Protein X19 is absent in strain L8508::pWD37, but present in L8508::pWD35 and hence the gene for this protein has been tentatively assigned to fragment 35.)

Cloning of a PBSX Repressor Gene.

The xhi1479 allele renders *Bacillus subtilis* thermoinducible for PBSX. A strain which contains this allele, grows normally at 37° C., but upon shifting the growth temperature to 48° C., PBSX is induced leading to cell lysis. This phenotype is presumed to be coded by a gene which encodes a PBSX repressor protein (4).

Fragments of DNA from the PBSX region of the chromosome were cloned into a replicating plasmid pRP22, and tested for their ability to allow the strain *B. subtilis* lA4201, which is thermoinducible for PBSX, to grow at the nonpermissive temperature. A clone containing a 1.2 kb fragment was isolated which when cloned into pUB110 was capable of complementing the xhi1479 allele. This fragment was therefore expected to encode the wild-type repressor protein.

Determination of the Nucleotide Sequence.

Nucleotide sequences from the 1.2 kb fragment was determined by the dideoxy chain termination method (42). The 1.2 kb EcoRl fragment was cloned in both orientations into the EcoRl site of M13mp18. This allowed the determination of the sequence of both ends of the fragment. Further sequencing was carried out by generating a set of deletions using Bal31 exonuclease. In each case, the nucleotide sequence was determined using an M13 universal primer. Where overlapping sequences were not obtained, oligonucleotides with complementarity to the known sequence were used as primers. The nucleotide sequence was determined for both strands and is shown in FIG. 8, for bases 220–1195.

Sequence Analysis

1. Homology to Known Sequences

As an initial step in the analysis of the sequence, both strands of the 1200 bp sequence were searched for open reading frames of greater than 90 nucleotides in length. In total 13 such open reading frames were found of which orf1 is indicated in FIG. 8.

In order to see if the sequence was homologous to any known DNA sequence, the Genbank database (release no. 58) was searched with both strands of the DNA sequence using the methods of Lipman and Pearson (27). No significant homology was found.

The sequence was then translated into all six reading frames, ignoring stop codons, and each one was used to search the NBRF/PIR protein database. This method was employed for convenience and also has the advantage that frame shift errors in the sequence will not affect significantly the result of the homology search. The translated product of one open reading frame showed weak homology when compared with bacteriophage P22 c2 repressor, the dicA gene product from *E. coli,* phage P1/P2 C repressor, the phi105 cl repressor, and the phi105 orf3 gene product. The region of homology in each case was found to correspond to the open reading frame (orf1) which has the potential to code for a protein of 113 amino acids (nucleotides 397–736).

Each of the proteins with homology to orf1 is either known, or postulated to be a DNA-binding protein with a repressor function. An alignment of these proteins produced by the method of Higgins and Sharp (22) indicates that homology between these proteins is restricted to the N-terminal regions. The homologous region includes the proposed DNA binding domain of each of the previously characterised proteins and strongly suggests that a protein encoded by orf1 is also a DNA-binding protein with and α-helix, turn, α-helix motif. The putative DNA-binding domain of the orf1 protein is shown in FIG. 8.

Using the methods of Dodd and Egan (11), for the detection of 'cro-like' DNA-binding domains, the proposed DNA-binding domain received a score of 1911, whereas the scores of the proteins in the master set ranged from 1684 to 2968. The authors found that in a search of the PIR protein database containing 2560 sequences, no proteins were found with a score of greater than 1700 that were not thought to be DNA-binding proteins. The score obtained suggests that orf1 encodes a 'cro-like' DNA-binding protein.

When the sequence of the fragment from the strain carrying the xhi1479 allele (FIG. 9) is compared with the wild type sequence (FIG. 8) it can be seen that 14 nucleotide substitutions occur within orf1 . Only three of these lead to amino acid changes: glycine to serine at position 4, alanine to valine at position 19, and leucine to valine at position 78. The alanine to valine change lies within the proposed DNA-binding domain. Valine is rarely found at this position in other 'cro-like' DNA-binding domains, and the change reduces the 'Dodd and Egan' score from 1911 to 1597, which is outside the range which these authors observed for the master set of proteins (1684–2968). This observation is consistent with the proposal that orf1 encodes a "cro-like" DNA-binding protein. The evidence suggests that the xhi1479 repressor is temperature sensitive because of one or more of the amino acid substitutions identified from the comparison of the orf1 sequences shown in FIGS. 8 and 9.

2. Transcriptional and Translational Signals

The sequence was searched for translational and transcriptional signals. The region 5' to each of the open reading frames indicated was examined for sequences which resemble ribosome binding sites (rbs) i.e. sequences which show complementarity to the 3' end of the *B. subtilis* 16S rRNA. The rbs 5' to orf1 is underlined in FIG. 8. The free energy of binding of this sequence (delta G) with the 3' end of the 16S rRNA was calculated to be $-18.2$ kcal mol$^{-1}$. Previously reported delta G values for ribosome binding sites of gram positive genes range from −11.8 to −22 kcal mol-1 (20). The sequence upstream from orf1 was examined for potential promoter signals related to the −35, (TTGACA), and −10, (TATAAT), consensus sequence for sigma $^{43}$ recognised promoters, which are usually separated by 17 or 18 base pairs (30). Two possible promoter sequences were found, P1a and P1b, and are indicated in FIG. 8.

The sequence was also examined for potential transcriptional termination sequences, which are often characterised by inverted repeats, thought to be capable of forming particular secondary structure. No typical terminator sequences were found.

3. Potential Repressor Binding Sites.

Many phage and cellular repressors are autoregulatory, and as such are preceded by binding sites for the repressor protein. The region preceding the gene for the repressor was examined for sequences showing characteristics of protein binding sites. Although showing little sequence homology, protein binding sites have some common features; the sequences are usually around 20 bp in size and they often contain internal dyad symmetry. The region immediately 5' to orf1 was found to contain three direct repeats of 19 bp each, which have provisionally been named 01, 02 and 03. 01 and 03 are identical over the 19 bp, and contain an internal palindromic sequence of 6 base pairs. 02 differs from these in 2 of the 19 positions, and is flanked on either side by a further inverted repeat sequence of 7 base pairs in length. The region containing these operator sequences overlaps with the proposed promoter elements for transcription of orf1 suggesting that transcription of this gene may be regulated by the protein or proteins. We predict that the orf1 gene product 15 protein interacts at 01, 02 and 03 and controls the production of itself autogenously.

The DNA sequence shown in FIG. 8 provides good evidence that orf1 encodes a sequence specific DNA binding protein, with a typical helix-turn-helix binding domain. The DNA sequence of FIG. 8 also contains sites likely to be involved in the control of expression of orf1. These sites include putative promoters, ribosome binding sites and operators. It is hypothesised that the operator-like sequences are recognised by the product of orf1. A product of the sequence in FIG. 8, probably orf1, complements the xhi1479 allele.

The homologous 1.2 kb fragment from the heat inducible strain B.subtilis IA4201 was also cloned and sequenced. It shows a total of 67 differences when compared to the equivalent sequence from the wild-type strain B.subtilis S0113. These differences include 65 nucleotide substitutions, an insertion of 2 bp at position 222 of the wild-type sequence, and a deletion of 1 bp at position 830. The sequence corresponding to the sequence of FIG. 8 is shown in FIG. 9.

On the basis of this evidence we claim that we have identified a PBSX repressor gene (orf1) which ultimately controls the expression of the late genes of PBSX, and any genes expressed from late PBSX promoters, and that we have identified operator sequences recognised by this repressor.

Cell Lysis and Induction and Expression of Alpha-Amylase.

Tests for lysis, and for induction and expression of alpha-amylase, in B. subtilis strains, carrying various plasmids integrated in the PBSX genome were performed in the absence of antibiotics. Overnight cultures were inoculated into 200 ml of Luria Broth in a side-arm flask and grown in an orbital incubator (Gallenkamp) at 200 rpm. Optical density, as a measure of cell numbers and therefore of growth and lysis, was measured on a Klett-Summerson photoelectric colorimeter with a green filter number 54. For thermoinduction experiments cultures were split in two and one half shifted to 48° C., the other half maintained at 37° C. The time of induction of each culture is shown in appropriate figures (10–12). In the case of rapid thermoinduction flasks were placed in a shaking waterbath for 8 minutes at 48° C., for gradual induction they were placed directly into an orbital incubator at the same temperature. Aliquots were removed at intervals prior to and post induction and centrifuged at 3,000 g for 15 minutes, the pellets were retained for chromosomal DNA preparation and alpha amylase assays were performed on the supernates.

FIG. 10 shows growth curves for 1A4201::pWD35 and 1A4201::pWD38 and the effect of temperature induction at 2 hours. After heat induction the latter strain lyses, but the former does not. This shows that certain integrants, of which 1A4201::35 is an example, are deficient in lysis after induction of PBSX. This is due to mutagenesis caused by integration of derivatives of the non-replicative plasmid pWD3 carrying segments of the PBSX genome, in this case pWD35. The strain carrying pWD38 is not defective in lysis. This experiment establishes that integration at certain sites in the PBSX genome blocks lysis. Table 2 is a summary of the data for various integrants.

Expression of an Heterologous Gene Inserted in the PBSX Genome is Heat Inducible in a Strain Carrying the xhi1479 allele.

FIG. 11 shows that on raising the temperature of the culture to 48° C. at time zero the strain 1A4201::pWD35 which carries the heat inducible PBSX mutation xhi1479 begins to express the HT amylase gene from pWD35, which is integrated in the PBSX genome. In a control strain not carrying the xhi1479 allele HT alpha amylase expression was not expressed at a detectable level. In a second control strain LA2, which carries the HT amylase gene on a plasmid pSA33 (37) where it is expressed under the control of its own promoter, the level of expression of the HT gene is less and is not heat inducible.

This experiment establishes that a promoterless heterologous gene can be integrated in the PBSX genome, and that expression of this gene can be induced by heat in an xhi1479 background.

The DNA sequence of a fragment carrying the xhi1479 allele was determined as described above for the 1.2 kb fragment of PBSX and is shown in FIG. 9.

Cony Number Estimation

The objective of these experiments was to measure the copy number of the DNA sequences integrated in the PBSX genome before and after heat induction of a strain carrying the xhi1479 mutation.

Plasmid pJG14 (Devine et al, J. Bacteriol. 1989., 171, 1166) was used as a $^{32}$p radiolabelled probe. This carries the CAT gene which is also part of all the derivatives of pWD3, and a segment of the chromosomal β-glucanase gene. It can therefore be used to measure the copy number of the pWD35 sequences integrated in the PBSX genome relative to the copy number of chromosomal sequences not linked to PBSX. Chromosomal DNA preparations from 1A4201::pWD35 were made from cells harvested at different times before and after heat induction. Heat induction was carried out under regimes as described above, rapid induction and gradual induction. The DNA was digested with EcoR1 and electrophoresed on a 0.8% agarose gel. Southern blot and hybridisation on Biodyne membranes was performed as advised by the manufacturers. Autoradiography was performed on probed filters. Copy number was estimated by comparing the intensity of the signal produced by DNA within the PBSX region to DNA from another part of the chromosome (β-glucanase). Signal intensity was measured on a DESAGA Chromatogram Densitometer CD50.

FIG. 12a shows the growth curves of 1A4201::pWD35 thermoinduced rapidly or gradually after 2 hours. Item FIG. 12b shows the copy number of the CAT gene relative to the β-glucanase gene in both cultures as a function of time. It can be seen that the copy number of CAT rises after heat induction to peak values of 5–8 per chromosomal copy of β-glucanase. It falls later for unknown reasons.

This experiment establishes that heat induction of the PBSX system causes an increase in the copy number of genes integrated in the PBSX genome.

Transcription of the PBSX Late Operon Requires a Positive Control Factor.

Transcription of the PBSX late operon can be detected only after induction of the prophage. The promoter for this operon has been localised by insertional mutagenesis to lie within a 1.3 kb EcoR1–Sac1 fragment, 38 (Wood et al., in press). The mechanisms whereby transcription from this promoter is controlled were examined.

For the isolation and characterisation of factors involved in transcriptional regulation from this promoter, a genetic background lacking the PBSX prophage was desirable.

Although attempts to cure *B. subtilis* 168 of the PBSX prophage failed, strains which contain large deletions in the PBSX region of the chromosome have been isolated (5). Hybridisation analysis of one of these strains *B. subtilis* RB1081, indicated that the deleted region includes the late operon of the prophage and at least some of the early region, including the previously cloned repressor gene (Wood et al., manuscript submitted). Thus, this strain provides a useful background for the analysis of transcriptional control of the late operon.

Construction of Late Promoter-LacZ Fusion Strains

Bacterial strains and plasmids are listed in table 4.

Transcription from the late promoter was monitored by using a transcriptional fusion to the β-galactosidase structural gene. The PBSX late promoter $P_L$, was removed from pWD38 on a 1.3 kb EcoR1–BamH1 fragment and cloned between EcoR1 and BamH1 sites of DG268, immediately 5' to a promoterless lacZ gene. The resulting plasmid was linearised using XbaI and used to transform *B. subtilis* strains RB1081 and 1A420. Integration of the plasmid into the chromosome by a double recombination event results in disruption of the β-amylase coding sequence by the integrated $P_L$-lacZ fusion (see FIG. 13). This resulted in strains RB1081[$P_L$-lacZ] and 1A420[$P_L$-lacz]. In each case the late promoter-lacZ fusion is integrated at the amylase locus which is quite distinct from the PBSX prophage.

Expression of the Late Operon is Positively Regulated.

β-galactosidase production in each of these strains was examined in the absence and presence of MMC (table 5). In the case of RB1081[$P_L$-lacz], no expression of β-galactosidase was observed. In 1A420[$P_L$-lacz], expression of β-galactosidase was observed only after induction of the resident prophage by addition of MMC to the media. These results confirmed the presence of a promoter on this fragment and furthermore suggested that transcription from the late promoter is not directly controlled by the repressor (as no repressor gene is present in RB1081), but rather is positively controlled by a PBSX encoded factor.

Isolation of a Fragment which Encodes a Positive Control Factor.

In order to isolate the gene encoding this factor, DNA from a plasmid which contains a 15 kb insert spanning the PBSX early region (pHV1435h), was digested with HindIII. Fragments were ligated to the *E.coli—B. subtilis* shuttle vector, pEB112(cut with HindIII), and transformed into *B. subtilis* RB1081[$P_L$-lacZ]. Kanamycin resistant transformants were screened for production of β-galactosidase. Four such transformants were isolated, each of which was noted to grow poorly, and when restreaked on fresh plates, segregated white colonies. Each of the recombinant plasmids contains a 1.5 kb HindIII fragment. One of these plasmids was named pWH15. It is not known whether the observed instability is due to the cloned insert; the vector, pEB112, has previously been reported to be unstable in *B. subtilis*.

This fragment may enclose a novel sigma factor such as is found in the *B. subtilis* lytic phage SP01 (reviewed by Losick and Pero, (53); a factor which is required in addition to the host holoenzyme such as the gene 4 protein of φ29 (54); or an anti-termination factor, analogous to the Q protein of λ (reviewed in Hendrix et al., (21).

Conclusion

A molecular genetic analysis of the PBSX prophage has been carried out by examining the effects of integrating plasmid sequences at different sites within the metA–metC region of the *B. subtilis* 168 chromosome. Insertional mutagenesis has allowed the identification of early and late regions of the prophage. The relative positions of these regions within the cloned region is consistent with proposed genetic map of this region which suggests that mutations within a regulatory region (xin and xhi), are located to the metA proximal side of mutations within genes affecting particle proteins (xhd, xtl, xki) (4, 15, 49).

It is suggested that many of the late phage genes are contained within a large operon of between 18 and 30 kb. in length and transcribed in the direction metA-metC. Such polycistronic operons are characteristic of other phage genomes eg. lambda (21). The coding capacity of this operon may be sufficient to produce all the phage structural and late proteins (29). However the existence of another late operon cannot be excluded as ambiguity surrounds the location of the genes coding for the proteins P35/X35 and P18.

Although the full extent of the PBSX genome has not been determined, it is apparent from insertional mutagenesis that it is at least 20 kb. This is confirmation at the DNA level that the PBSX genome is considerably larger than the 13 kb. fragments of DNA that are packaged within the phage heads (2, 18, 19, 34). The cloning of an origin of replication from the PBSX region of the chromosome has been reported (1).

By integrating the promoterless alpha-amylase gene at the PBSX locus the potential for using PBSX functions as the basis of a thermoinducible expression vehicle has been demonstrated. Plasmid based thermoinducible expression systems have been described for *B. subtilis* which exploit the controlling elements of early region of acteriophage phi105 (10, 38). The system presented here demonstrates that a foreign gene can be integrated on the *B. subtilis* chromosome under the control of an inducible prophage promotor. Furthermore the foreign gene is located within a structure reported to the capable of undergoing stable gene amplification (24). Indeed stable maintenance of both single and amplified copies of the alpha-amylase gene have been observed when integrated at this locus.

It is convenient to obtain heat-inducible expression by integrating the gene within PBSX carrying the xhi1479 allele. Depending on the site of integration the system may be manipulated so that on induction it shows an increase in copy number and/or it does not lyse and/or it shows induced expression of the integrated gene. These integrants are stable at low temperature.

After induction it has been shown that the copy number of the DNA integrated in PBSX increases. The repressor gene (orf1) has beencloned and sequenced. Operator and promotor sequences have been identified. The xhi1479 allele can be used as the basis of a heat inducible expression system to obtain heat inducible expression of heterologous genes transcribed from promoters which are controlled by operators of the type shown in 01,02 and 03.

Restriction Mapping the Sequence Data from the Early Region of PBSX:

FIG. 16 is not drawn to scale. but reading left to right it shows:

(i) A 1.2 kb EcoRl fragment which carries open reading frames. One orfl is the repressor gene. The second of 69 condons reads in the opposite orientation and is called orf13. The sequence between orfl and orfl3 has four related inverted repeats. These overlap four putative promoters for sigma 37 RNA polymerase, two facing into orf1 and two facing into orf13. The inverted repeats thus resemble operators of the type $O_R$ of phage lambda. Orf13 may be another controlling gene.

Additional information that orfl encodes the repressor function on the 1.2 kb EcoRl fragment: a Bcll—Nael fragment of 0.73 kb carries orfl but not orfl3. This fragment encodes repressor activity as judged by its ability to confer temperature-insensitivity on 1A4201.

(ii) A 0.9 kb EcoRl fragment.

(iii) An EcoRl fragment called 316. Inserts at 316 block induction of PBSX.

(iv) A 0.8 kb EcoRl fragment.

(v) An EcoRl—Sacl fragment called 38 which carries the late phage promoter. This has been sequenced and the sequence is shown in FIG. 15. It has three long open reading frames of unknown function.

(vi) A Sacl—EcoRl fragment called 340.

(vii) An EcoRl—EcoRl fragment called 37. This has been sequenced. This fragment is expected to contain one or more late genes.

(viii) A HindIII 1.5 kb fragment which overlaps 316 and 38 and contains the small 0.8 kb EcoRl fragment. The fragment encodes a positive control function which stimulates transcription from the late promoter on fragment 38. The HindIII fragment has been sequenced. One ORF called orf2 encodes a sequence resembling a helix-turn-helix motif and therefore may encode a DNA-binding protein. This ORF is slightly homologous to sigB of B. subtilis. A deletion of Bcll fragment which overlaps the 5' end of orf2 eliminates the positive control activity of the HindIII fragment. These data suggest that orf2 encodes the positive control factor.

A current working model of the system is as follows:

There is a single transcription unit which extends from the 1.2 kb EcoRl fragment at the left into the 1.5 kb HindIII fragment. The first gene in this fragment is orf13.

The gene orf1 (now called xre) encodes the PBSX repressor.

The repressor binds to the operators between orf1 and orf13.

At low repressor concentration the expression of orf13 is repressed by Xre, the repressor encoded by orf1.

At high repressor concentration the expression of orf1 is repressed by Xre.

On induction the repressor concentration is greatly reduced allowing transcription into orf13 and into the positive control factor gene on the 1.5 kb HindIII fragment which is believed to be encoded by orf 2.

The positive control factor causes transcription from the late promoter on fragment 38.

Due to the genetic and morphological similarities between PBSX and the related phibacins PBSW, PBSY and PBSZ, these phibacins would also be expected to be suitable for use as expression systems as dicussed above.

LITERATURE CITED

1. Anderson, L. M., H. E. Ruley, and K. F. Bott. 1982. Isolation of an autonomously replicating DNA fragment from the region of defective bacteriophage PBSX of Bacillus subtilis. J. Bacteriol. 150: 1280–1286.

2. Anderson, L. M., and K. Bott. 1985. DNA packaging by the Bacillus subtilis defective bacteriophage PBSX. J. Virol. 54: 773–780.

3. Birnboim, H. C., and J. Doly. 1979. A rapid alkaline extraction procedure for screening recombinant plasmid DNA. Nuc. Acids Res. 7: 1513–1523.

4. Buxton, R. S. 1976. Prophage mutation causing heat inducibility of defective Bacillus subtilis bacteriophage PBSX. J. Virol. 20: 22–28.

5. Buxton, R. S. 1980. Selection of Bacillus subtilis 168 mutants with deletions of the PBSX prophage. J. Gen. Virol. 46: 427–437.

6. Bradley, D. E. 1967. Ultra structure of bacteriophages and bacteriocins. Bacteriol. Rev. 31: 230–314.

7. Cleveland, D. W., S. G. Fischer, M. W. Kirschner, and U. K. Laemmli. 1976. Peptide mapping by limited proteolysis in sodium dodecyl sulfate and analysis by gel electrophoresis. J. Biol. Chem. 252: 1102–1106.

8. Cohen, S. N., A. C. Y Chang, and L. Hsu. 1972. Non-chromosomal antibiotic resistance in bacteria: genetic transformation of E. coli by R-factor DNA. Proc. Natl. Acad. Sci. U.S.A. 69: 2110–2114.

9. Contente, S., and D. Dubnau. 1979. Characterisation of plasmid transformation in Bacillus subtilis: kinetic properties and the effect of DNA conformation. Mol. Gen. Genet. 167: 251–258.

10. Dhaese, P., C. Hussey, and M. van Montagu. 984. Thermoinducible gene expression in Bacillus subtilis using transcriptional regulatory elements from temperate phage 0105. Gene 32: 181–194.

11. Dodd, I. B., and J. B. Egan. 1987. Systematic method for the detection of potential cro-like DNA-binding regions in proteins. J. Mol. Biol. 194: 557–564.

12. Duncan, C. H., G. A. Wilson, and F. E. Young. 1978. Mechanism of integrating foreign DNA during transformation of Bacillus subtilis. Proc. Natl. Acad. Sci. U.S.A. 75: 3664–3668.

13. Frischauf, A., H. Lehrach, A. Poustka, and N. Murray. 1983. Lambda replacement vectors carrying polylinker sequences. J. Mol.

Biol. 170: 827–842.

14. Garro, A. J., and J. Marmur. 1970. Defective bacteriophages. J. Cell Physiol. 76: 253–264.

15. Garro, A. J., H. Leffert, and J. Marmur. 1970. Genetic mapping of a defective bacteriophage on the chromosome of Bacillus subtilis 168. J. Virol. 6: 340–343.

16. Garro, A. J., P. Hammer, and B. Recht. 1976. Biochemical and genetic Analysis of the defective Bacillus subtilis bacteriophage PBSX. p. 340–349. In D. Schlessinger (ed.), Microbiology-1976. American Society for Microbiology, Washington D.C.

17. Gryczan, T., S. Contente, and D. Dubnau. 1980. Molecular cloning of heterologous chromosomal DNA by recombination between a plasmid vector and a homologous resident plasmid in Bacillus subtilis. Mol. Gen. Genet. 177: 459–467.

18. Haas, M., and H. Yoshikawa. 1969. Defective bacteriophage PBSH in Bacillus subtilis. I. Induction, purification and physical properties of the bacteriophage and its deoxyribonucleic acid. J. Virol. 3: 233–247.

19. Haas, M., and H. Yoshikawa. 1969. Defective bacteriophage PBSH in Bacillus subtilis. II. Intracellular development of the induced prophage. J. Virol. 3: 248–260.

20. Hagar, P. W. and J. C. Rabinowitz. 1985. Translational specificity in Bacillus subtilis. In D. A. Dubnau (ed.) "The molecular biology of the Bacilli" Vol II Academic Press Inc.

21. Hendrix, R. W., J. W. Roberts, F. W. Stahl, and R. A. Weisberg (eds.), 1982. Lambda II. Cold Spring Harbour Laboratories, Cold Spring Harbour, N.Y.

22. Higgins, D. G., and P. M. Sharp. 1988. CLUSTAL: a package for preforming multiple alignments on a microcomputer. Gene 73; 237–244.

23. Huang, W. M., and J. Marmur. 1970. Characterisation of inducible bacteriophages in Bacillus licheniformis. J. Virol. 5: 237–246.

24. Janniere, L., B. Niaudet, E. Piere and S. D. Ehrlich. 1985. Stable gene amplification in the chromosome of Bacilus subtilis. Gene 40: 47–55.

25. Konisky, J. 1978. The Bacteriocins, p71–136. In I. C. Gunsalus and R. Y. Stanier (eds.), The Bacteria, Vol. VI. Academic Press, N.Y. and London.

26. Laemmli, U. K. 1970. Cleavage of structural proteins during assembly of the head protein of bacteriophage T4. Nature (London) 227: 680–685.

27. Lipman and Pearson. 1985. Rapid and sensitive protein similarity searches. Science 227: 1345.

28. Maniatis, T., E. F. Fritsch, and J. Sambrook. 1982. Molecular Cloning: a laboratory manual. Cold Spring Harbor Laboratories, Cold Spring Harbor, N.Y.

29. Mauel C., and D. Karamata. 1984. Characterisation of proteins induced by mitomycin C treatment of *Bacillus subtilis*. J. Virol. 49: 806–812.

30. Moran, C. P., N. Lang, S. F. J. Legrice, G. Lee, M. Stephens, A. L. Sonenshein, J. Pero and R. Losick, 1982. Nucleotide sequences that signal the initiation of transcription and translation in *Bacillus subtilis*. Mol. Gen. Genet. 186:339.

31. Murphy, P., B. C. A. Dowds, D. J. McConnell, and K. M. Devine. 1987. Oxidative stress and growth temperature in *Bacillus subtilis*. J. Bacteriol. 169: 5766–5770.

32. Niaudet, B., A. Goze, and S. D. Ehrlich. 1982. Insertional mutagenesis in *Bacillus subtilis*: mechanism and use in gene cloning. Gene 19: 277–284.

33. Okamoto, K., J. A. Mudd, J. Mangan, W. M. Huang, T. V. Subbaiah, and J. Marmur. 1968. Properties of the defective phage of *Bacillus subtilis*. J. M. Biol. 34: 413–428.

34. Okamoto, K., J. A. Mudd, and J. Marmur. 1968. Conversion of *Bacillus subtilis* DNA to phage DNA following mitomycin C induction. J. M. Biol. 34: 429–437.

35. O'Kane, C., B. A. Cantwell and D. J. McConnell. 1985. Mapping of the gene for endo-beta-1, 3-1, 4-glucanase of *Bacillus subtilis*. FEMS Microbiol. Lett. 29: 135–139.

36. O'Kane, C., M. A. Stephens, and D. J. McConnell. 1986. Integrable alpha-amylase plasmid for generating transcriptional fusions in *Bacillus subtilis*. J. Bacteriol. 168: 973–981.

37. Ortlepp, S. A., J. F. Ollington, and D. J. McConnell. 1983. Molecular cloning in Bacillus subtilis of a *Bacillus licheniformis* gene encoding a thermostable alpha-amylase. Gene 23: 267–276.

38. Osburne, M. S., R. J. Craig and D. M. Rostein. 1985. Thermoinducible control elements from temperate bacteriophage phil05. J. Bacteriol. 163: 1101–1108.

39. Piggot, P. J. and S. Y. Taylor. 1977. New types of mutation affecting formation of alkaline phosphatase by *Bacillus subtilis* in sporulation conditions. J. Gen. Microbiol. 102: 69–80.40.

40. Piggot, P. J., C. A. Curtis, and H. de Lencastre. 1984. Use of integrational plasmids to demonstrate the polycistronic nature of a transcriptional unit (spoIIA) required for sporulation of *Bacillus subtilis*. J. Gen. Microbiol. 130: 2123–2136.

41. Sancar, A., A. M. Hach and W. D. Rupp. 1979. Simple method for identification of plasmid-coded proteins. J. Bacteriol. 137: 692–693.

42. Sanger, F., S. Nicklen and A. R. Coulson. 1977. DNA sequencing with chain-terminating inhibitors. Proc. Natl. Acad. Sci. USA 74:5463–5467.

43. Southern, E. M. 1975. Detection of specific sequences among DNA fragments separated by gel electrophoresis. J. Mol. Biol. 98: 503–517.

44. Steensma, H. Y., L. A. Robertson, and J. D. van Elsas. 1978. The occurrence and taxonomic value of PBSX-like defective phages in the Genus Bacillus. Antonie van Leeuwenhoek 44: 353–366.

45. Seaman, E., E. Tarmy, and J. Marmur. 1964. Inducible bacteriophages of *Bacillus subtilis*. Biochemistry 3: 607–613.

46. Subbaiah, T. V., C. D. Goldthwaite, and J. Marmur. 1966. Nature of bacteriophages induced in *Bacillus subtilis*, p435–446. In V. Bryson and H. J. Vogel (eds.), Evolving Genes and Proteins, Academic Press, N.Y.

47. Tagg, J. R., A. S. Dajani, and L. Wannamaker. 1976. Bacteriocins of Gram positive bacteria. Bacteriol. Rev. 40: 722–756.

48. Thurm, P., and A. J. Garro. 1975. Bacteriophage—specific protein synthesis during induction of the defective *Bacillus subtilis* bacteriophage PBSX. J. Virol. 10: 179–183.

49. Thurm, P., and A. J. Garro. 1975. Isolation and characterisation of prophage mutants of the defective *Bacillus subtilis* bacteriophage PBSX. J. Virol. 16: 184–191.

50. Yanisch-Perron, C., J. Vieira, and J. Messing. 1985. Improved M13 phage cloning vectors and host strains: nucleotide sequences of the M13mp18 and pUC19 vectors. Gene 33: 103–119.

51. Kageyama, M. 1975. Bacteriocins and bacteriophages in *Pseudomonas aeruginosa*. In "Micobial Drug Resistance: S. Mitsuhashi and H. Hashimoto (eds.). Tokyo: Univ. Tokyo pp. 291–305.

52. Leonhardt, H. and Alonso, J. C. 1988. Construction of a shuttle vector for inducible gene expression in *E. coli* and *B. subtilis*. J. Gen. Microbiol. 134: 605–609

53. Losick, R. and Pero, J. 1982. Cascades of sigma factors. Cell. 25: 582–584

54. Mellado, R. P., Barthelemy, I. and Salas, M. 1988. Transcription initiation and termination signals of the *Bacillus subtilis* phage $\phi$29. In 'Genetics and Biotechnology of Bacilli'. Ganesan and Hoch (Eds.). Academic Press Inc., C. A.

TABLE 1

| Plasmid, strain or bacteriophage | Genotype | Source or reference |
|---|---|---|
| Plasmid: | | |
| pBD64 | $Cm^R$ | (16) |
| pUC18 | $Ap^R$ | (44) |
| pSL5 | $Ap^R$, -amy structural gene | (31) |
| pOK411C | $Cm^R$, -amy structural gene | (31) |
| pWD3 | $Cm^R Ap^R$, -amy structural gene | This study. |
| *E. coli:* | | |
| DH5α | $F^- end^{A1} hsd^{R17} (r_K^-, m_K^+)$ $sup^{E44} thi^{-1} lambda^- rec^{A1}$ $gyr^{A96} rel^{A1} o80dlacZ\Delta M15$ | Bethseda Research Laboratories. |
| Nm539 | $sup^F hsd^R$ (P2cox3) | (12), Promega Biotec. |
| CSR603 | $F^- thr^{-1} leu^{B6} pro^{A2} phr^{-1}$ $rec^{A1} arg^{E3} thi^{-1} uvr^{A6}$ $ara^{-14} lac^{Y1} gal^{K2} sup^{E44}$ $mtl^{-1} rps^{L31} tsx^{-33} xyl^5$ lambda$^-$ | R. L. Rodriquez. |
| *B. subtilis* 168: | | |
| SO113 | $trp^{C2} amy^{-3}$ | (32) |
| IA420 | $ilv^{A1} met^{B5} pur^{A16}$ $xhi^{1479} xki^{1479}$ | (4), BGSC. |
| IA4201 | $ilv^{A1} met^{B5} xhi^{1479}$ $xki^{1479} amy^{-3}$ | This study. |
| L8508 | $xhi^{1479} lyt^{-2}$ | D. Karamata. |
| SL345 | $pho^{S5} leu^{A8} rif^{-2}$ spoIIE64 | R. Buxton. |
| IA78 | $met^{C3} pyr^A xtl^{-1}$ | BGSC. |
| IA158 | $met^A$ | BGSC. |
| *B. subtilis* W23: | | |
| SB623 | thr(PBSZ) | BGSC. |
| Bacteriophage: | | |
| Lambda EMBL3 | | (12), Promega Biotec. |
| PBS-1 | | BGSC. |

TABLE 2

| Integrated Plasmid | Killing Activity on B. subtilis W23 | Cell Lysis upon PBSX Induction |
|---|---|---|
| None | + | + |
| 316 | − | − |
| 38 | + | + |
| 37 | − | − |
| 35 | − | − |
| 314 | − | − |
| 313 | − | − |
| 32 | − | − |
| 31 | − | − |
| 311 | − | − |
| 312 | − | − |
| 39 | + | + |

TABLE 3

| PROTEIN (m. wt.) | INTEGRATED PLASMID | | | | | | |
|---|---|---|---|---|---|---|---|
| | 316 | 38 | 37 | 35 | 32 | 312 | 39 |
| X76(Tail) | − | + | − | − | − | − | + |
| P70 | − | + | + | + | + | + | + |
| P36 | − | + | − | + | + | + | + |
| X35 (Head) | − | + | − | + | + | + | + |
| P32 | − | + | − | − | − | − | + |
| P31 | − | + | − | − | − | − | + |
| X19(Tail) | − | + | − | + | + | + | + |
| P18 | − | + | − | + | + | + | + |
| p14 | − | + | + | + | + | + | + |

TABLE 4

| Strains | Description | Reference/Source |
|---|---|---|
| B. subtilis RB1081 | pro(AB) pyrXΔPBSX | Ref 5 |
| B. subtilis 1A420 | ilvA1 metB5 purA16 xhi 1479 xki 1479 | Ref 4 |

TABLE 4-continued

| Strains | Description | Reference/Source |
|---|---|---|
| Plasmids: | | |
| pWD38 | pWD3 with 1.3 kb $Eco^{R1}$-$Sac^1$ fragment containing PBSX late operon promoter ($P_L$) | Inventors Lab. |
| pDG268 | $Cm^R$, integrating vector. Contains promoterless lacZ amy E | Inventors Lab. |
| pEB112 | E. coli-B. subtilis shuttle/expression vector ($Ap^R$, $Kn^R$) | Ref 52. |
| hHV1435h | hHH1435 with 15 kb of PBSX DNA from clone C | Inventors Lab. |

TABLE 5

| | β-galactosidase activity | |
|---|---|---|
| | −MMC | +MMC |
| B. subtilis RB1081[$P_L$-lacZ] ( PBSX) | − | − |
| B. subtilis 1A4201[$P_L$-lacZ] (PBSX) | − | + |
| B. subtilis RB1081[$P_L$-lacZ]/pEB112 | − | n.e. |
| B. subtilis RB1081[$P_L$-lacZ]/pWH15* | + | n.e. |

β-galactosidase production in B. subtilis 168 strains containing transcriptional fusions of the PBSX late promoter ($P_L$), to the β-galactosidase structural gene. (β-galactosidase production was scored by observing blue colouration of colonies when grown on media containing X-gal).
*Plasmid pWH15 contains a 1.5 kb HindIII fragment from the early region of PBSX, cloned into the unique HindIII site of pEB112.
n.e. not examined.

We claim:

1. An expression system for the expression of a gene product of interest comprising a phibacin or a mutant thereof, or at least one induction controlled functional operon or mutant thereof from a phibacin,the mutants having retained the induction controlled operon function, wherein said phibacin is selected from the group consisting of PBSW, PBSX, PBSY and PBSZ of *Bacillus subtlis* and wherein the expression of a DNA sequence coding for said product of interest is under control of said phibacin or functional operon or mutant thereof.

2. The expression system as claimed in claim 1 comprising the phibacin contained in *Bacillus subtilis* deposited with the National Collection of Industrial Bacteria, under accession no. NCIMB 40205 or a mutant of the deposited phibacin which retains the induction controlled operon function.

3. The expression system as claimed in claim 1 comprising said mutant of a phibacin which does not lyse the host cell on induction.

4. The expression system as claimed in claim 1 further comprising DNA sequences which encode a repressor, a promoter, and at least one operator, isolated from a phibacin selected from the group consisting of PBSW, PBSX, PBSY, and PBSZ of *Bacillus subtilis*.

5. A Bacillus host containing an expression system according to claim 1.

6. A method of integrating a DNA sequence of interest into a Bacillus chromosome, in which a segment of DNA from an expression system as claimed in claim 1 is inserted into a plasmid carrying the DNA sequence to be integrated, the plasmid is introduced into a bacterial cell carrying on the chromosome at least a portion of phibacin DNA having the same or substantially the same DNA sequence as that of the phibacin DNA in the plasmid, whereby recombination between the phibacin DNA in the plasmid and in the chromosome is accomplished, thereby integrating the DNA sequence of interest into the chromosome, and integrants are selected.

7. A method of producing a gene product of interest, which comprises culturing a Bacillus host containing DNA encoding the gene product of interest inserted into and under the control of the expression system of claim 1, and inducing the production of the gene product.

8. The expression system as claimed in claim 3 wherein the mutant is produced by insertional mutagenesis.

9. The expression system as claimed in claim 4 wherein the phibacin carries a temperature sensitive repressor allele.

10. The expression system of claim 9 wherein the temperature sensitive allele is the xhi1479 mutation.

11. The expression system as claimed in claim 9 comprising the mutant phibacin contained in *Bacillus subtilis* 1A4201 deposited with the National Collection of Industrial Bacteria, under the accession no NCIMB 40206 or a mutant of the deposited phibacin which retains the induction controlled operon function, and is non-lysogenic on induction.

12. The expression system as claimed in claim 4 wherein the DNA sequence which encodes the repressor is the gene designated orf1 of phibacin PBSX in FIG. 8(SEQ ID NO 1), or mutants thereof having retained the ability to encode protein having repressor function.

13. The expression system as claimed in claim 4 wherein the promoter has the DNA sequence shown in FIG. 15, between the −10 and −35 consensus sequences, or a mutant thereof having retained the ability to act as a promoter.

14. The expression system of claim 4 wherein the operator has the sequence of any one of the operators 01, 02, and 03 shown in FIG. 8(SEQ ID NO. 1) or a mutant thereof having retained the ability to act as an operator.

15. The expression system as claimed in claim 4 comprising a DNA sequence encoding a temperature sensitive repressor so that product expression is heat-inducible.

16. The expression system of claim 4 which also comprises a gene encoding a positive control factor isolated from a phibacin.

17. The expression system as claimed in claim 15 wherein said DNA sequence is the xhi1479 allele of the gene designated orf1of PBSX in FIG. 9(SEQ ID NOS 3 and 5), or mutants thereof having retained the ability to encode a protein having heat-inducible repressor function.

18. The expression system of claim 16 wherein the positive control factor-encoding gene is the gene designated orf2 of phibacin PBSX.

19. A DNA sequence isolated from a phibacin selected from the group consisting of PBSW, PBSX, PBSY and PBSZ of *Bacillus subtilis,* which encodes a repressor, or a mutant thereof having retained the ability to encode a protein having repressor function.

20. The DNA sequence of claim 19 which is isolated from PBSX.

21. The DNA sequence claimed in claim 19 contained in the phibacin in *Bacillus subtilis* SO113 deposited with the National Collection of Industrial Bacteria, under the accession no. NCIMB 40205, or a mutant of the sequence which encodes a protein having a repressor function and/or a mutant of the sequence encoding a positive control factor.

22. The DNA sequence of claim 20 comprising the gene designated orf1 in FIG. 8(SEQ ID NO 1), or mutants thereof having retained the ability to encode a protein having repressor function.

23. The DNA sequence of claim 22 wherein the repressor encoded is temperature sensitive.

24. The DNA Sequence of claim 23 which is the temperature sensitive xhi1479 allele in FIG. 9(SEQ ID NOS 3 and 5) of the gene designated orf1 of PBSX or mutants thereof which encode a protein having repressor function.

25. A DNA sequence isolated from a phibacin selected from the group consisting of PBSW, PBSX, PBSY, and PBSZ of *Bacillus subtilis,* which encodes a positive control factor.

26. The DNA sequence claimed in claim 25 contained in the phibacin in *Bacillus subtilis* 1A4201 deposited with the national Collection of Industrial Bacteria, under the accession no. NCIMB 40206, respectively, or a mutant of the sequence which encodes a protein having a repressor function and/or a mutant of the sequence encoding a positive control factor.

27. A Bacillus host containing a DNA sequence as claimed in claim 1.

28. A plasmid carrying a DNA sequence according to claim 21.

29. A plasmid carrying a DNA sequence according to claim 26.

30. The host of claim 5 which is a *Bacillus subtilis* host.

31. The host of claim 27 which is a *Bacillus subtilis* host.

32. A DNA sequence encoding a phibacin, wherein said phibacin is selected from the group consisting of PBSW, PBSX, PBSY and PBSz of *Bacillus subtilis.*

* * * * *

UNITED STATES PATENT AND TRADEMARK OFFICE

CERTIFICATE OF CORRECTION

PATENT NO. : 5,843,702

DATED : December 1, 1998

INVENTOR(S) : McConnell et al.

It is certified that error appears in the above-identified patent and that said Letters Patent is hereby corrected as shown below:

Col. 4, line 55, delete " ↦ " and insert -- ⟼ --;

Col. 9, line 15, delete "thechloramphenicol" and insert -- the chloramphenicol--;

Col. 14, line 22, delete "Cony" and insert --Copy--;

Col. 15, line 24, delete "$P_L$-lacz" and insert --$P_L$-lacZ--;

Col. 15, line 30, delete "$P_L$-lacz" and insert --$P_L$-lacZ--;

Col. 15, line 31, delete "$P_L$-lacz" and insert --$P_L$-lacZ--;

UNITED STATES PATENT AND TRADEMARK OFFICE
CERTIFICATE OF CORRECTION

PATENT NO. : 5,843,702

DATED : December 1, 1998

INVENTOR(S) : McConnell et al.

It is certified that error appears in the above-identified patent and that said Letters Patent is hereby corrected as shown below:

Col. 125, line 37, Claim 1, delete "*subtlis*" and insert --*subtilis*--;

Col. 126, line 37, Claim 9, delete "claim 4" and insert --claim 8--;

Col. 128, line 15, Claim 27, delete "claim 1" and insert --claim 25--;

Col. 128, line 25, Claim 32, delete "PBSz" and insert --PBSZ--.

Signed and Sealed this

Thirtieth Day of November, 1999

Attest:

*Attesting Officer*

Q. TODD DICKINSON

*Acting Commissioner of Patents and Trademarks*

SEQUENCE LISTING ( 1 ) GENERAL INFORMATION:

( i i i ) NUMBER OF SEQUENCES: 185

( 2 ) INFORMATION FOR SEQ ID NO:1:

( i ) SEQUENCE CHARACTERISTICS:
        ( A ) LENGTH: 983 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 180..518

( x i ) SEQUENCE DESCRIPTION: SEQ ID NO:1:

```
ATGTGATCAC  TCTCCTGATC  TTTTTTGATA  CATTTGTAT   CGGATGTTAC  CAAGTATAAA       60

CGATACATTC  TGTATCATCA  AGTTATTTTT  GATACTTTTT  TTATCATAAC  TTTATTTTGA      120
```

```
TACATTTTGT ATCTATAATC ATAAGTAACG TAGGGAGTTT AAAAAAGAGA GGTCATAGT         179

ATG ATA GGC GGC AGA TTG AAG AGT CTC AGA GGG AAA AGG ACA CAG GAA          227
Met Ile Gly Gly Arg Leu Lys Ser Leu Arg Gly Lys Arg Thr Gln Glu
 1           5                  10                  15

GAA ATC GCA TCA CAC ATC GGT GTG TCA CGG GCA CGA TAT TCC CAC TAT          275
Glu Ile Ala Ser His Ile Gly Val Ser Arg Ala Arg Tyr Ser His Tyr
             20              25                  30

GAA AAC GGG CGA AGC GAA CCC GAT TAC GAC ACA CTC CAA AAG CTG GCT          323
Glu Asn Gly Arg Ser Glu Pro Asp Tyr Asp Thr Leu Gln Lys Leu Ala
         35              40              45

GAT TAC TTT CAA GTA ACG ACT GAT TAC TTA TTA ACG GGG AAA GAC AAA          371
Asp Tyr Phe Gln Val Thr Thr Asp Tyr Leu Leu Thr Gly Lys Asp Lys
     50              55              60

AAA TCC GAT GAC GAT ATG TTC TCA GAT CCG GAC CTG CAG CTT GCA TAC          419
Lys Ser Asp Asp Asp Met Phe Ser Asp Pro Asp Leu Gln Leu Ala Tyr
 65              70              75                      80

CGC GAT ATG CAG GAT TTT TCC CCA GAA AGC AAA CAG CAG GCC ATC GAA          467
Arg Asp Met Gln Asp Phe Ser Pro Glu Ser Lys Gln Gln Ala Ile Glu
                 85              90                  95

TTT ATC AAC TAT TTA AAA GAA AAA GAG AAA AAC CGC AAA CCG AAA AAT          515
Phe Ile Asn Tyr Leu Lys Glu Lys Glu Lys Asn Arg Lys Pro Lys Asn
             100             105                 110

AAA TAAATCGTTC TCTGTTCTCT AAAACATATA AAAGTAGAC CGATATAAAG                568
Lys

AAAAAAGTGT TTATTTTTTA AAGAAAAGGG AAAGATTTCT ACACTACCTT CCAGTCCTAT         628

ACGGGCTTTT CTTTCTCGCT AAAAACAGAA CAAACGTTCG AAAGGGAGTA TTCAATTGGG         688

CGATTACTTA TCACATCTGG AGGAATACGT TAAAAATTTA TACGGCCGGC TGGGCATCAC         748

ATCCCCTCAT CACATTGACA TGCTGAAAAT CGCAAAGGAT CTGGATATTT GGGTGCATTT         808

TGAGGATATG GGGAGCATGA TGGTGAAATA CGACGGCATG TACAGTATCG TATTGAACCA         868

AAAAAAGTCA CGGGAAGAGC AATGGGAGGA TTTTGGCCAT GAGCTGTGCC ACGTGTTAAA         928

GCATGCAGGC AATCATTTTC AGATGAACAA GCTCTTCAGA GAGCTTCAGG AATTC             983
```

( 2 ) INFORMATION FOR SEQ ID NO:2:

( i ) SEQUENCE CHARACTERISTICS:
        ( A ) LENGTH: 113 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ile Gly Gly Arg Leu Lys Ser Leu Arg Gly Lys Arg Thr Gln Glu
 1           5                  10                  15

Glu Ile Ala Ser His Ile Gly Val Ser Arg Ala Arg Tyr Ser His Tyr
             20              25                  30

Glu Asn Gly Arg Ser Glu Pro Asp Tyr Asp Thr Leu Gln Lys Leu Ala
         35              40              45

Asp Tyr Phe Gln Val Thr Thr Asp Tyr Leu Leu Thr Gly Lys Asp Lys
     50              55              60

Lys Ser Asp Asp Asp Met Phe Ser Asp Pro Asp Leu Gln Leu Ala Tyr
 65              70              75                      80

Arg Asp Met Gln Asp Phe Ser Pro Glu Ser Lys Gln Gln Ala Ile Glu
                 85              90                  95

Phe Ile Asn Tyr Leu Lys Glu Lys Glu Lys Asn Arg Lys Pro Lys Asn
             100             105                 110
```

Lys ( 2 ) INFORMATION FOR SEQ ID NO:3:

( i ) SEQUENCE CHARACTERISTICS:
        ( A ) LENGTH: 978 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 182..520

( x i ) SEQUENCE DESCRIPTION: SEQ ID NO:3:

```
ATGTGATATC ACTCTCCTGA TCTGTTTTGA TACTTTTCGT ATCAACTGTT ACCAAGTATA      60

AACGATACAA ACTGTATCAT CAAGTTATTT TTGATACTTT TTTTATCATA ACTTTATTTT     120

GATACAGATT GTATCTATAA TCATTAGTAA CTTAGGGAGT TTAAAAAAGA GAGGTCATAG     180

T ATG ATA GGC AGC AGA TTG AAG AGT CTC AGA GGG AAA AGG ACA CAG GAA    229
  Met Ile Gly Ser Arg Leu Lys Ser Leu Arg Gly Lys Arg Thr Gln Glu
  1               5                   10                  15

GAA ATC GTA TCT CAT ATC GGT GTG TCG CGG GCA CGA TAT TCC CAC TAT      277
Glu Ile Val Ser His Ile Gly Val Ser Arg Ala Arg Tyr Ser His Tyr
            20                  25                  30

GAA AAC GGG CGA AGC GAA CCT GAT TAC GAC ACA CTC CAA AAG CTG GCT      325
Glu Asn Gly Arg Ser Glu Pro Asp Tyr Asp Thr Leu Gln Lys Leu Ala
        35                  40                  45

GAT TAC TTT CAA GTA ACG ACT GAT TAC TTA TTA ACA GGG AAA GAC AAA      373
Asp Tyr Phe Gln Val Thr Thr Asp Tyr Leu Leu Thr Gly Lys Asp Lys
    50                  55                  60

AAA TCC GAT GAC GAT ATG TTC TCA GAT CCC GAC TTG CAG GTA GCA TAC      421
Lys Ser Asp Asp Asp Met Phe Ser Asp Pro Asp Leu Gln Val Ala Tyr
65                  70                  75                  80

CGT GAT ATG CAG GAT TTT TCC CCA GAA AGC AAA CAG CAG GCC ATT GAA      469
Arg Asp Met Gln Asp Phe Ser Pro Glu Ser Lys Gln Gln Ala Ile Glu
                85                  90                  95

TTT ATC AAC TAT TTA AAA GAA AAA GAG AAA AAC CGG AAA CCG AAA AAT      517
Phe Ile Asn Tyr Leu Lys Glu Lys Glu Lys Asn Arg Lys Pro Lys Asn
            100                 105                 110

AAA TAAATATTTC TCTGTTCTCT AAAACATATG AAAAATAGAC CGATATAAAG           570
Lys

AAAAAAGTGT TTATTTTTTT AAGAAAAGGG AAAGATTTCA ACACACTTTC CAGTCCTATT    630

AGGGCTTTTC TTTCTCGCTA AAAACAGAAC ACACGTTCGA AAGGGAGTAT TCAATTGGGC    690

GATTACTTAT CACATCTGGA GGAATACGTA AAAAATTTAT ACAGCCGGCT GGGCATCACC    750

TCCCCCCATC ACATTGACAT GCTGAAAATC GCAAGGATC TGGATATTTG GGTTCATTTT     810

GAGGATATGG GGAGCATGAT GGTTAAATAC GATGGCATGT ACAGTATCGT ATTGAATCAA    870

AGAAAATCAC GAGAAGAGCA ATGGGAGGAT TTTGGCCATG AACTGTGCCA CGTGTTAAAG    930

CACGCAGGCA ATCATTTTCA AATGAACAAG CTCTTCAGGG AACTGCAG                978
```

( 2 ) INFORMATION FOR SEQ ID NO:4:

( i ) SEQUENCE CHARACTERISTICS:
        ( A ) LENGTH: 113 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Ile | Gly | Ser | Arg | Leu | Lys | Ser | Leu | Arg | Gly | Lys | Arg | Thr | Gln | Glu |
|---|---|---|---|---|---|---|---|---|---|---|---|---|---|---|---|
| 1 | | | | 5 | | | | | 10 | | | | | 15 | |

| Glu | Ile | Val | Ser | His | Ile | Gly | Val | Ser | Arg | Ala | Arg | Tyr | Ser | His | Tyr |
|---|---|---|---|---|---|---|---|---|---|---|---|---|---|---|---|
| | | | 20 | | | | | 25 | | | | | 30 | | |

| Glu | Asn | Gly | Arg | Ser | Glu | Pro | Asp | Tyr | Asp | Thr | Leu | Gln | Lys | Leu | Ala |
|---|---|---|---|---|---|---|---|---|---|---|---|---|---|---|---|
| | | 35 | | | | | 40 | | | | | 45 | | | |

| Asp | Tyr | Phe | Gln | Val | Thr | Thr | Asp | Tyr | Leu | Leu | Thr | Gly | Lys | Asp | Lys |
|---|---|---|---|---|---|---|---|---|---|---|---|---|---|---|---|
| | 50 | | | | | 55 | | | | | 60 | | | | |

| Lys | Ser | Asp | Asp | Asp | Met | Phe | Ser | Asp | Pro | Asp | Leu | Gln | Val | Ala | Tyr |
|---|---|---|---|---|---|---|---|---|---|---|---|---|---|---|---|
| 65 | | | | | 70 | | | | | 75 | | | | | 80 |

| Arg | Asp | Met | Gln | Asp | Phe | Ser | Pro | Glu | Ser | Lys | Gln | Gln | Ala | Ile | Glu |
|---|---|---|---|---|---|---|---|---|---|---|---|---|---|---|---|
| | | | | 85 | | | | | 90 | | | | | 95 | |

| Phe | Ile | Asn | Tyr | Leu | Lys | Glu | Lys | Glu | Lys | Asn | Arg | Lys | Pro | Lys | Asn |
|---|---|---|---|---|---|---|---|---|---|---|---|---|---|---|---|
| | | | 100 | | | | | 105 | | | | | 110 | | |

Lys ( 2 ) INFORMATION FOR SEQ ID NO:5:

( i ) SEQUENCE CHARACTERISTICS:
    ( A ) LENGTH: 976 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 180..518

( x i ) SEQUENCE DESCRIPTION: SEQ ID NO:5:

```
ATGTGATCAC  TCTCCTGATC  TTTTTTGATA  CATTTTGTAT  CGGATGTTAC  CAAGTATAAA        60

CGATACATTC  TGTATCATCA  AGTTATTTTT  GATACTTTTT  TTATCATAAC  TTTATTTTGA       120

TACATTTTGT  ATCTATAATC  ATAAGTAACG  TAGGGAGTTT  AAAAAAGAGA  GGTCATAGT        179
```

| ATG | ATA | GGC | GGC | AGA | TTG | AAG | AGT | CTC | AGA | GGG | AAA | AGG | ACA | CAG | GAA | 227 |
|---|---|---|---|---|---|---|---|---|---|---|---|---|---|---|---|---|
| Met | Ile | Gly | Ser | Arg | Leu | Lys | Ser | Leu | Arg | Gly | Lys | Arg | Thr | Gln | Glu | |
| 1 | | | | 5 | | | | | 10 | | | | | 15 | | |

| GAA | ATC | GCA | TCA | CAC | ATC | GGT | GTG | TCA | CGG | GCA | CGA | TAT | TCC | CAC | TAT | 275 |
|---|---|---|---|---|---|---|---|---|---|---|---|---|---|---|---|---|
| Glu | Ile | Ala | Ser | His | Ile | Gly | Val | Ser | Arg | Ala | Arg | Tyr | Ser | His | Tyr | |
| | | | 20 | | | | | 25 | | | | | 30 | | | |

| GAA | AAC | GGG | CGA | AGC | GAA | CCC | GAT | TAC | GAC | ACA | CTC | CAA | AAG | CTG | GCT | 323 |
|---|---|---|---|---|---|---|---|---|---|---|---|---|---|---|---|---|
| Glu | Asn | Gly | Arg | Ser | Glu | Pro | Asp | Tyr | Asp | Thr | Leu | Gln | Lys | Leu | Ala | |
| | | 35 | | | | | 40 | | | | | 45 | | | | |

| GAT | TAC | TTT | CAA | GTA | ACG | ACT | GAT | TAC | TTA | TTA | ACG | GGG | AAA | GAC | AAA | 371 |
|---|---|---|---|---|---|---|---|---|---|---|---|---|---|---|---|---|
| Asp | Tyr | Phe | Gln | Val | Thr | Thr | Asp | Tyr | Leu | Leu | Thr | Gly | Lys | Asp | Lys | |
| | 50 | | | | | 55 | | | | | 60 | | | | | |

| AAA | TCC | GAT | GAC | GAT | ATG | TTC | TCA | GAT | CCG | GAC | CTG | CAG | CTT | GCA | TAC | 419 |
|---|---|---|---|---|---|---|---|---|---|---|---|---|---|---|---|---|
| Lys | Ser | Asp | Asp | Asp | Met | Phe | Ser | Asp | Pro | Asp | Leu | Gln | Leu | Ala | Tyr | |
| 65 | | | | | 70 | | | | | 75 | | | | | 80 | |

| CGC | GAT | ATG | CAG | GAT | TTT | TCC | CCA | GAA | AGC | AAA | CAG | CAG | GCC | ATC | GAA | 467 |
|---|---|---|---|---|---|---|---|---|---|---|---|---|---|---|---|---|
| Arg | Asp | Met | Gln | Asp | Phe | Ser | Pro | Glu | Ser | Lys | Gln | Gln | Ala | Ile | Glu | |
| | | | | 85 | | | | | 90 | | | | | 95 | | |

| TTT | ATC | AAC | TAT | TTA | AAA | GAA | AAA | GAG | AAA | AAC | CGC | AAA | CCG | AAA | AAT | 515 |
|---|---|---|---|---|---|---|---|---|---|---|---|---|---|---|---|---|
| Phe | Ile | Asn | Tyr | Leu | Lys | Glu | Lys | Glu | Lys | Asn | Arg | Lys | Pro | Lys | Asn | |
| | | | 100 | | | | | 105 | | | | | 110 | | | |

| AAA | TAAATCGTTC | TCTGTTCTCT | AAAACATATA | AAAAGTAGAC | CGATATAAAG | 568 |
|---|---|---|---|---|---|---|
| Lys | | | | | | |

-continued

| | | | | | |
|---|---|---|---|---|---|
| AAAAAAGTGT | TTATTTTTTA | AAGAAAAGGG | AAAGATTTCT | ACACACCTTC | CAGTCCTATA | 628
| CGGGCTTTTC | TTTCTCGCTA | AAAACAGAAC | AAACGTTCGA | AAGGGAGTAT | TCAATTGGGC | 688
| GATTACTTAT | CACATCTGGA | GGAATACGTT | AAAAATTTAT | ACGGCCGGCT | GGGCATCACA | 748
| TCCCCTCATC | ACATTGACAT | GCTGAAAATC | GCAAAGGATC | TGGATATTTG | GGTGCATTTT | 808
| GAGGATATGG | GGAGCATGAT | GGTGAAATAC | GACGGCATGT | ACAGTATCGT | ATTGAACCAA | 868
| AAAAAGTCAC | GGGAAGAGCA | ATGGGAGGAT | TTTGGCCATG | AGCTGTGCCA | CGTGTTAAAG | 928
| CATGCAGGCA | ATCATTTTCA | GATGAACAAG | CTCTTCAGAG | AGCTTCAG | | 976

(2) INFORMATION FOR SEQ ID NO:6:

(i) SEQUENCE CHARACTERISTICS:
        (A) LENGTH: 113 amino acids
        (B) TYPE: amino acid
        (D) TOPOLOGY: linear (ii) MOLECULE TYPE: Protein (xi) SEQUENCE DESCRIPTION: SEQ ID NO:6:

Met Ile Gly Ser Arg Leu Lys Ser Leu Arg Gly Lys Arg Thr Gln Glu
 1               5                  10                  15

Glu Ile Ala Gly His Ile Gly Val Ser Arg Ala Arg Tyr Ser His Tyr
             20                  25                  30

Glu Asn Gly Arg Ser Glu Pro Asp Tyr Asp Thr Leu Gln Lys Leu Ala
         35                  40                  45

Asp Tyr Phe Gln Val Thr Thr Asp Tyr Leu Leu Thr Gly Lys Asp Lys
     50                  55                  60

Lys Ser Asp Asp Asp Met Phe Ser Asp Pro Asp Leu Gln Leu Ala Tyr
 65                  70                  75                  80

Arg Asp Met Gln Asp Phe Ser Pro Glu Ser Lys Gln Gln Ala Ile Glu
                 85                  90                  95

Phe Ile Asn Tyr Leu Lys Glu Lys Glu Lys Asn Arg Lys Pro Lys Asn
                100                 105                 110

Lys (2) INFORMATION FOR SEQ ID NO:7:

(i) SEQUENCE CHARACTERISTICS:
        (A) LENGTH: 1200 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 397..735

(xi) SEQUENCE DESCRIPTION: SEQ ID NO:7:

| | | | | | |
|---|---|---|---|---|---|
| GAATTCAACA | ACCCTGAATA | CGTCGGAAAA | GGATAGCTTT | TATCGTTTTT | CATTGTACTC | 60
| CGCTTCTCCT | TTTAACATCA | TGTATGCTTG | AAACTGTTCC | TGCGTTTCAA | AGTGAAACAC | 120
| CGGAAGGCCG | CATGCGGTAA | ACGAAATGGT | GCCGCCGGAT | TGTCCGAGAT | GGCGCTGATC | 180
| TATGGGATTT | TCACTAAAAA | CGATTTGGAT | CGGATACATG | TGATCACTCT | CCTGATCTTT | 240
| TTTGATACAT | TTTGTATCGG | ATGTTACCAA | GTATAAACGA | TACATTCTGT | ATCATCAAGT | 300
| TATTTTTGAT | ACTTTTTTTA | TCATAACTTT | ATTTTGATAC | ATTTTGTATC | TATAATCATA | 360
| AGTAACGTAG | GGAGTTTAAA | AAAGAGAGGT | CATAGT ATG | ATA GGC GGC | AGA TTG | 414
| | | | Met | Ile Gly Gly | Arg Leu | |

```
AAG  AGT  CTC  AGA  GGG  AAA  AGG  ACA  CAG  GAA  GAA  ATC  GCA  TCA  CAC  ATC        462
Lys  Ser  Leu  Arg  Gly  Lys  Arg  Thr  Gln  Glu  Glu  Ile  Ala  Ser  His  Ile
               10                  15                       20

GGT  GTG  TCA  CGG  GCA  CGA  TAT  TCC  CAC  TAT  GAA  AAC  GGG  CGA  AGC  GAA        510
Gly  Val  Ser  Arg  Ala  Arg  Tyr  Ser  His  Tyr  Glu  Asn  Gly  Arg  Ser  Glu
               25                  30                       35

CCC  GAT  TAC  GAC  ACA  CTC  CAA  AAG  CTG  GCT  GAT  TAC  TTT  CAA  GTA  ACG        558
Pro  Asp  Tyr  Asp  Thr  Leu  Gln  Lys  Leu  Ala  Asp  Tyr  Phe  Gln  Val  Thr
               40                  45                       50

ACT  GAT  TAC  TTA  TTA  ACG  GGG  AAA  GAC  AAA  AAA  TCC  GAT  GAC  GAT  ATG        606
Thr  Asp  Tyr  Leu  Leu  Thr  Gly  Lys  Asp  Lys  Lys  Ser  Asp  Asp  Asp  Met
 55                       60                  65                            70

TTC  TCA  GAT  CCG  GAC  CTG  CAG  CTT  GCA  TAC  CGC  GAT  ATG  CAG  GAT  TTT        654
Phe  Ser  Asp  Pro  Asp  Leu  Gln  Leu  Ala  Tyr  Arg  Asp  Met  Gln  Asp  Phe
                    75                  80                       85

TCC  CCA  GAA  AGC  AAA  CAG  CAG  GCC  ATC  GAA  TTT  ATC  AAC  TAT  TTA  AAA        702
Ser  Pro  Glu  Ser  Lys  Gln  Gln  Ala  Ile  Glu  Phe  Ile  Asn  Tyr  Leu  Lys
                    90                  95                       100

GAA  AAA  GAG  AAA  AAC  CGC  AAA  CCG  AAA  AAT  AAA  TAAATCGTTC  TCTGTTCTCT         755
Glu  Lys  Glu  Lys  Asn  Arg  Lys  Pro  Lys  Asn  Lys
               105                      110

AAAACATATA  AAAAGTAGAC  CGATATAAAG  AAAAAAGTGT  TTATTTTTA  AAGAAAAGGG                 815

AAAGATTTCT  ACACTACCTT  CCAGTCCTAT  ACGGGCTTTT  CTTTCTCGCT  AAAAACAGAA                875

CAAACGTTCG  AAAGGGAGTA  TTCAATTGGG  CGATTACTTA  TCACATCTGG  AGGAATACGT                935

TAAAAATTTA  TACGGCCGGC  TGGGCATCAC  ATCCCTCAT   CACATTGACA  TGCTGAAAAT                995

CGCAAAGGAT  CTGGATATTT  GGGTGCATTT  TGAGGATATG  GGGAGCATGA  TGGTGAAATA               1055

CGACGGCATG  TACAGTATCG  TATTGAACCA  AAAAAAGTCA  CGGGAAGAGC  AATGGGAGGA               1115

TTTTGGCCAT  GAGCTGTGCC  ACGTGTTAAA  GCATGCAGGC  AATCATTTTC  AGATGAACAA               1175

GCTCTTCAGA  GAGCTTCAGG  AATTC                                                        1200
```

( 2 ) INFORMATION FOR SEQ ID NO:8:

( i ) SEQUENCE CHARACTERISTICS:
        ( A ) LENGTH: 113 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met  Ile  Gly  Gly  Arg  Leu  Lys  Ser  Leu  Arg  Gly  Lys  Arg  Thr  Gln  Glu
 1                   5                   10                       15

Glu  Ile  Ala  Ser  His  Ile  Gly  Val  Ser  Arg  Ala  Arg  Tyr  Ser  His  Tyr
               20                  25                       30

Glu  Asn  Gly  Arg  Ser  Glu  Pro  Asp  Tyr  Asp  Thr  Leu  Gln  Lys  Leu  Ala
               35                  40                       45

Asp  Tyr  Phe  Gln  Val  Thr  Thr  Asp  Tyr  Leu  Leu  Thr  Gly  Lys  Asp  Lys
          50                  55                       60

Lys  Ser  Asp  Asp  Asp  Met  Phe  Ser  Asp  Pro  Asp  Leu  Gln  Leu  Ala  Tyr
 65                       70                  75                            80

Arg  Asp  Met  Gln  Asp  Phe  Ser  Pro  Glu  Ser  Lys  Gln  Gln  Ala  Ile  Glu
               85                  90                       95

Phe  Ile  Asn  Tyr  Leu  Lys  Glu  Lys  Glu  Lys  Asn  Arg  Lys  Pro  Lys  Asn
               100                      105                      110

Lys
```

(2) INFORMATION FOR SEQ ID NO:9:

(i) SEQUENCE CHARACTERISTICS:
        (A) LENGTH: 1201 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 180..518

(xi) SEQUENCE DESCRIPTION: SEQ ID NO:9:

```
GAATTCAACT ACCCTGAATA CGTCAGAAAA GGATAGCTTT TATCGTGTTT CATTGTACGC      60
CGCTTCTCCT TTTAACATCA TGTATGTTTG AAACTGTTCT TGCGTTTCAA AGTGGAACAC     120
CGGAAGTCCG CATGCCGTAA ACGAAATGGT GCCGCCAGAT TGTCCGAGAT GGCGCTGATC     180
TATGGGATTT TCACTAAAAA CAATTGGAT GGGATACATG TGATATCACT CTCCTGATGT      240
TTTTTGATTC ATCTTGTATC AACTGTTACC AAGTATAAAC GATACAAACT GTATCATCAA     300
GTTATTTTTG ATACTTTTTT TATCATAACT TTATTTTGAT ACAGATTGTA TCTATAATCA     360
TTAGTAACTT AGGGAGTTTA AAAAGAGAG GTCATAGTAT GATAGGCAGC AGATTGAAGA      420
GTCTCAGAGG GAAAAGGACA CAGGAAGAAA TCGTATCTCA TATCGGTGTG TCGCGGGCAC     480
GATATTCCCA CTATGAAAAC GGGCGAAGCG AACCTGATTA CGACACACTC CAAAAGCTGG     540
CTGATTACTT TCAAGTAACG ACTGATTACT TATTAACAGG GAAAGACAAA AAATCCGATG     600
ACGATATGTT CTCAGATCCC GACTTGCAGG TAGCATACCG TGATATGCAG GATTTTTCCC     660
CAGAAAGCAA ACAGCAGGCC ATTGAATTTA TCAACTATTT AAAAGAAAAA GAGAAAAACC     720
GGAAACCGAA AAATAAATAA ATATTTCTCT GTTCTCTAAA ACATATGAAA AATAGACCGA     780
TATAAAGAAA AAAGTGTTTA TTTTTTTAAG AAAAGGGAAA GATTTCAACA CACTTTCCAG     840
TCCTATTAGG GCTTTTCTTT CTCGCTAAAA ACAGAACACA CGTTCGAAAG GGAGTATTCA     900
ATTGGGCGAT TACTTATCAC ATCTGGAGGA ATACGTAAAA AATTTATACA GCCGGCTGGG     960
CATCACCTCC CCCCATCACA TTGACATGCT GAAAATCGCA AAGGATCTGG ATATTTGGGT    1020
TCATTTTGAG GATATGGGGA GCATGATGGT TAAATACGAT GGCATGTACA GTATCGTATT    1080
GAATCAAAGA AAATCACGAG AAGAGCAATG GGAGGATTTT GGCCATGAAC TGTGCCACGT    1140
GTTAAAGCAC GCAGGCAATC ATTTTCAAAT GAACAAGCTC TTCAGGGAAC TGCAGGAATT    1200
C                                                                   1201
```

(2) INFORMATION FOR SEQ ID NO:10:

(i) SEQUENCE CHARACTERISTICS:
        (A) LENGTH: 2559 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..2559

(xi) SEQUENCE DESCRIPTION: SEQ ID NO:10:

```
AAG CTT TGT CAA ACA AAG AAA GTC ATT GTG GAA CAT ACC GGT ATT GGA      48
Lys Leu Cys Gln Thr Lys Lys Val Ile Val Glu His Thr Gly Ile Gly
115                 120                 125
```

```
GTT GTT TTT CAT CCA TGT CCG AAC TGC CGG TCC GCG ACT GAC TTA ACG        96
Val Val Phe His Pro Cys Pro Asn Cys Arg Ser Ala Thr Asp Leu Thr
130             135                 140                 145

CCT GTC ATT CAA AAG CTG GAG CAA ATG CTG ACA GCG GGA AAA GCG AGG       144
Pro Val Ile Gln Lys Leu Glu Gln Met Leu Thr Ala Gly Lys Ala Arg
                150                 155                 160

CTG AAT ATC TAT GAT TAA ACA GCT GAC TGC TCT AAT CGC TTT GCT GTT       192
Leu Asn Ile Tyr Asp  *  Thr Ala Asp Cys Ser Asn Arg Phe Ala Val
                165                 170                 175

TCG GGC AAA GCG AAC AGA AAA AAA CAT TGA ACA ATG TAA GGA CGA           240
Ser Gly Lys Ala Asn Arg Lys Lys His  *  Thr Met Val  *  Gly Arg
            180                 185                 190

CGG GAA GTG AAA GTG TTG GCA AAG ACA AAA CAG GCA GAG AAA AGC CCT       288
Arg Glu Val Lys Val Leu Ala Lys Thr Lys Gln Ala Glu Lys Ser Pro
        195                 200                 205

GCG CCG TGG CGT GCT GTC CCG TGC GGG GAT ACG AAA CCG ATC TAT ATT       336
Ala Pro Trp Arg Ala Val Pro Cys Gly Asp Thr Lys Pro Ile Tyr Ile
210                 215                 220                 225

TAT TCA GCT TAC AGT GAA GAA GAA AAA GAA AGA TTT CCG TAC TCA AAC       384
Tyr Ser Ala Tyr Ser Glu Glu Glu Lys Glu Arg Phe Pro Tyr Ser Asn
                230                 235                 240

GGG CGG CTG ATT GCA GCT GTA TTT GAC CTC AGC TCT TAT TCG CAA AAA       432
Gly Arg Leu Ile Ala Ala Val Phe Asp Leu Ser Ser Tyr Ser Gln Lys
            245                 250                 255

AGC AAT GCC TCT TTG ATG GCC GCT GCG CCT GAA TTG CTG GAA GCG TCT       480
Ser Asn Ala Ser Leu Met Ala Ala Ala Pro Glu Leu Leu Glu Ala Ser
        260                 265                 270

AAA GCA GCA GTT GAT TTT CTG AAA GGG AAT TCT ATT CAT TCA AAG GAG       528
Lys Ala Ala Val Asp Phe Leu Lys Gly Asn Ser Ile His Ser Lys Glu
275                 280                 285

CGT ATC ATT CAG CTA TTA GAA AAA GCT GAA GCA AGC GCT GCA CCG AAA       576
Arg Ile Ile Gln Leu Leu Glu Lys Ala Glu Ala Ser Ala Ala Pro Lys
290                 295                 300                 305

AGG GGA GGA AAT AAA ACA TGA TTC ATC CGA AAA AAC TGC TGC ATA TCG       624
Arg Gly Gly Asn Lys Thr  *  Phe Ile Arg Lys Asn Cys Cys Ile Ser
                310                 315                 320

ATT CCG TCA CGC TTA AGA GCC AGC TGG AGG ACG GGA AAA TCC GTC ATT       672
Ile Pro Ser Arg Leu Arg Ala Ser Trp Arg Thr Gly Lys Ser Val Ile
            325                 330                 335

ATT GTG GAC GGC ATC AAG CAA GAA GCA TGG ATC ACA GAA GCG CCA GAG       720
Ile Val Asp Gly Ile Lys Gln Glu Ala Trp Ile Thr Glu Ala Pro Glu
        340                 345                 350

CAT GGA AAA ACG CTC GTC GAA ACA AGA AAG GGC GAT CTT GCT CGT GTG       768
His Gly Lys Thr Leu Val Glu Thr Arg Lys Gly Asp Leu Ala Arg Val
355                 360                 365

GAA TTT GAA ATC GGC TAC AAA TTA AAT TAA AGC GAA AAC AGA ATA CGT       816
Glu Phe Glu Ile Gly Tyr Lys Leu Asn  *  Ser Glu Asn Arg Ile Arg
370                 375                 380                 385

CCA AGA CGG AAA GCC TGC GGA CAC TGA TCA ACT GCA CAG CAT TTG TGC       864
Pro Arg Arg Lys Ala Cys Gly His  *  Ser Thr Ala Gln His Leu Cys
                390                 395                 400

GTT GAT TGG TGT CCG TTT TTT ATT TGC CAA AAA TGA GGA GGA TCA TAG       912
Val Asp Trp Cys Pro Phe Phe Ile Cys Gln Lys  *  Gly Gly Ser  *
            405                 410                 415

AAT GCA AGA CTT ACT ATT TGA ATA TAA ACG CAC GCT CAA ACA AAC AAG       960
Asn Ala Arg Leu Thr Ile  *  Ile  *  Thr His Ala Gln Thr Asn Lys
        420                 425                 430

AAT ACA ATA TAA ACC GCT CGC TGA GGC AGA TGA ATC CGT GCT CTC AGC      1008
Asn Thr Ile  *  Thr Ala Arg  *  Gly Arg  *  Ile Arg Ala Leu Ser
435                 440                 445
```

| | | | | | | | | | | | | | | | | |
|---|---|---|---|---|---|---|---|---|---|---|---|---|---|---|---|---|
| TGA | AGA | GCT | GAA | GGA | TAA | AAA | AAT | CAT | CAG | AAA | TAT | GAT | TAC | TGA | TCT | 1056 |
| * | Arg | Ala | Glu | Gly | * | Lys | Asn | His | Gln | Lys | Tyr | Asp | Tyr | * | Ser | |
| 450 | | | | | 455 | | | | | 460 | | | | | 465 | |
| TGA | ATA | TGT | AAC | AGA | ATG | GCT | TGA | AAA | AGG | AAG | GCA | GCC | CGG | CAT | CAG | 1104 |
| * | Ile | Cys | Asn | Arg | Met | Ala | * | Lys | Arg | Lys | Ala | Ala | Arg | His | Gln | |
| | | | 470 | | | | | 475 | | | | | 480 | | | |
| ACG | GGC | GAT | TGA | CCG | GCG | TGA | TGT | TTA | CCA | GCG | GCT | GAT | GAT | CAA | GGA | 1152 |
| Thr | Gly | Asp | * | Pro | Ala | * | Cys | Leu | Pro | Ala | Ala | Asp | Asp | Gln | Gly | |
| | | | 485 | | | | | 490 | | | | | 495 | | | |
| CCC | GAG | AAT | CAT | CGA | ATC | ATT | TTC | CAG | CGC | TAT | GAT | GTT | TGA | GCC | GGA | 1200 |
| Pro | Glu | Asn | His | Arg | Ile | Ile | Phe | Gln | Arg | Tyr | Asp | Val | * | Ala | Gly | |
| | | 500 | | | | | 505 | | | | | 510 | | | | |
| CGG | ACA | GGT | ATC | AGA | AGA | AGA | CAG | AGA | TAG | AAT | TCG | AGA | AGC | ATT | AGC | 1248 |
| Arg | Thr | Gly | Ile | Arg | Arg | Arg | Gln | Arg | * | Asn | Ser | Arg | Ser | Ile | Ser | |
| | | | 515 | | | | | 520 | | | | | 525 | | | |
| CCT | GTT | AAC | GGA | CAG | AGA | AAA | GGA | AAT | GTT | TTT | GCT | GCA | TAA | GGT | AGA | 1296 |
| Pro | Val | Asn | Gly | Gln | Arg | Lys | Gly | Asn | Val | Phe | Ala | Ala | * | Gly | Arg | |
| 530 | | | | | 535 | | | | | 540 | | | | | 545 | |
| ATG | TTT | TTC | TTA | TGA | ACG | GAT | CGC | CGA | TCT | TCT | CGG | CGT | AAA | AAA | ATC | 1344 |
| Met | Phe | Phe | Leu | * | Thr | Asp | Arg | Arg | Ser | Ser | Arg | Arg | Lys | Lys | Ile | |
| | | | | 550 | | | | | 555 | | | | | 560 | | |
| GAC | AGT | GCA | AAC | GAC | GAT | TAA | ACG | GGC | GAG | TTT | AAA | GAT | GCA | AAG | ACA | 1392 |
| Asp | Ser | Ala | Asn | Asp | Asp | * | Thr | Gly | Glu | Phe | Lys | Asp | Ala | Lys | Thr | |
| | | | 565 | | | | | 570 | | | | | 575 | | | |
| GCA | GGA | AGA | AAT | GAA | TCG | ATC | ACT | TGC | CTG | AAA | GCT | TGT | CAT | ACG | TTT | 1440 |
| Ala | Gly | Arg | Asn | Glu | Ser | Ile | Thr | Cys | Leu | Lys | Ala | Cys | His | Thr | Phe | |
| | | 580 | | | | | 585 | | | | | 590 | | | | |
| GCC | ACC | TAT | AAG | TGA | ATA | GAG | CAT | GAC | ACT | AAG | CGG | CTG | GCT | GAT | CAG | 1488 |
| Ala | Thr | Tyr | Lys | * | Ile | Glu | His | Asp | Thr | Lys | Arg | Leu | Ala | Asp | Gln | |
| | | 595 | | | | | 600 | | | | | 605 | | | | |
| CCG | CTT | TTA | TGA | ATA | AAC | AAC | CAT | GCT | GGA | GGT | GGC | GGT | GAT | GCA | GTA | 1536 |
| Pro | Leu | Leu | * | Ile | Asn | Asn | His | Ala | Gly | Gly | Gly | Gly | Asp | Ala | Val | |
| 610 | | | | | 615 | | | | | 620 | | | | | 625 | |
| GCA | TGA | AAA | CAC | AAC | AGC | GCG | AAC | AAG | CAT | TAG | CAA | TCT | ATC | AAC | AAC | 1584 |
| Ala | * | Lys | His | Asn | Ser | Ala | Asn | Lys | His | * | Gln | Ser | Ile | Asn | Asn | |
| | | | | 630 | | | | | 635 | | | | | 640 | | |
| ATC | AAG | GAA | AGA | TCA | CAA | ATC | GGG | CGA | TTG | CGG | ACA | CAA | TCG | GTG | TTT | 1632 |
| Ile | Lys | Glu | Arg | Ser | Gln | Ile | Gly | Arg | Leu | Arg | Thr | Gln | Ser | Val | Phe | |
| | | | 645 | | | | | 650 | | | | | 655 | | | |
| CCG | CGA | AAA | CAA | TCG | GCA | TCT | GGA | AAA | AAC | AAG | ACA | AAT | GGA | AAG | AGG | 1680 |
| Pro | Arg | Lys | Gln | Ser | Ala | Ser | Gly | Lys | Asn | Lys | Thr | Asn | Gly | Lys | Arg | |
| | | | 660 | | | | | 665 | | | | | 670 | | | |
| CGC | TGT | TTT | CTG | CGT | CCA | AAA | ACG | AAC | AAA | AAC | AGC | GCC | CTA | TAA | ACA | 1728 |
| Arg | Cys | Phe | Leu | Arg | Pro | Lys | Thr | Asn | Lys | Asn | Ser | Ala | Leu | * | Thr | |
| | | 675 | | | | | 680 | | | | | 685 | | | | |
| ACG | ATG | AAT | TAA | ATG | AAC | GCC | AGC | GGC | TGT | TTT | GCC | TGT | ATT | ACG | TCA | 1776 |
| Thr | Met | Asn | * | Met | Asn | Ala | Ser | Gly | Cys | Phe | Ala | Cys | Ile | Thr | Ser | |
| 690 | | | | | 695 | | | | | 700 | | | | | 705 | |
| AAA | GCT | TCA | ATG | CCA | CAC | AGT | CAG | CAA | TCA | AAG | CGG | GCT | ATT | CTC | CGG | 1824 |
| Lys | Ala | Ser | Met | Pro | His | Ser | Gln | Gln | Ser | Lys | Arg | Ala | Ile | Leu | Arg | |
| | | | | 710 | | | | | 715 | | | | | 720 | | |
| ACA | GCG | CTC | ATG | TGA | CGG | GCA | GCC | GAC | TCT | TAA | AAA | ACG | AAA | AGG | TCG | 1872 |
| Thr | Ala | Leu | Met | * | Arg | Ala | Ala | Asp | Ser | * | Lys | Thr | Lys | Arg | Ser | |
| | | | | 725 | | | | | 730 | | | | | 735 | | |
| CTG | CTG | AAA | TTA | GAC | GCA | TTA | AAA | AAG | AAA | TGG | TCA | ATG | AAA | TGT | TTA | 1920 |
| Leu | Leu | Lys | Leu | Asp | Ala | Leu | Lys | Lys | Lys | Trp | Ser | Met | Lys | Cys | Leu | |
| | | | 740 | | | | | 745 | | | | | 750 | | | |
| TTG | AAG | CGA | TGG | ATG | TGC | TGC | AGG | TTT | ATA | TCA | AGA | TCG | CGT | TTG | CGG | 1968 |
| Leu | Lys | Arg | Trp | Met | Cys | Cys | Arg | Phe | Ile | Ser | Arg | Ser | Arg | Leu | Arg | |
| | | 755 | | | | | 760 | | | | | 765 | | | | |

```
ATA TTA CGG ACT ATG TGA CCT TTG GAA AAA AAG AGG TCC AGG CTG TCG      2016
Ile Leu Arg Thr Met  *  Pro Leu Glu Lys Lys Arg Ser Arg Leu Ser
770             775             780             785

GGA AAT CGG GTC CGC TGT TTG ATG AAG ATG ATA ATC CGA TTA TGA AGG      2064
Gly Asn Arg Val Arg Cys Leu Met Lys Met Ile Ile Arg Leu  *  Arg
            790             795             800

AAA TCA GCT TTG TCG ATG TCA AAG ACT CCG GGC TCG TTG ATG GCA CCA      2112
Lys Ser Ala Leu Ser Met Ser Lys Thr Pro Gly Ser Leu Met Ala Pro
        805             810             815

TTG TAA CGG AAG CAA AGC TTG GGA AAG AGG CAT TGC CAT CAA GCT TGC      2160
Leu  *  Arg Lys Gln Ser Leu Gly Lys Arg His Cys His Gln Ala Cys
            820             825             830

AGA TAA AAT GAA GGC GCT TGA GAA GCT ATC CTT ATA TTT TGA TTT GTT      2208
Arg  *  Asn Glu Gly Ala  *  Glu Ala Ile Leu Ile Phe  *  Phe Val
        835             840             845

TCC AGA TCA ATT TAA ACA AAA AAT TGA AAA TGA GAA ATT GAA GCT TGC      2256
Ser Arg Ser Ile  *  Thr Lys Asn  *  Lys  *  Glu Ile Glu Ala Cys
850             855             860             865

CAA ACA AAA AGC GGA GAA AAC AGA TGA CAG CCA GGA GCC GAT TGA AAT      2304
Gln Thr Lys Ser Gly Glu Asn Arg  *  Gln Pro Gly Ala Asp  *  Asn
            870             875             880

TAT GAT CAA ACG AAA AGA GCG CAA GTC ATG ATT GTA AAA GAA ATC AAC      2352
Tyr Asp Gln Thr Lys Arg Ala Gln Val Met Ile Val Lys Glu Ile Asn
        885             890             895

CCT CAT TTC GAA GAT TAC GTG TTC AAT TGG GAG CAG ACG TAC CAG TTT      2400
Pro His Phe Glu Asp Tyr Val Phe Asn Trp Glu Gln Thr Tyr Gln Phe
        900             905             910

CTT GTC GGC GGC TAC GGC TCA TCC AAA AGC TAT CAT ACC GCA TTG AAA      2448
Leu Val Gly Gly Tyr Gly Ser Ser Lys Ser Tyr His Thr Ala Leu Lys
    915             920             925

ATC GTG CTA AAG CTG CTG AAG GAA AAA CGG ACG GCC CTT GTG ATC CGG      2496
Ile Val Leu Lys Leu Leu Lys Glu Lys Arg Thr Ala Leu Val Ile Arg
930             935             940             945

GAG GTG TTC GAT ACC CAT CGG GAT TCG ACC TTC GCC TTG TTT CAA GAG      2544
Glu Val Phe Asp Thr His Arg Asp Ser Thr Phe Ala Leu Phe Gln Glu
            950             955             960

GTG ATC GAA GAG CTC                                                  2559
Val Ile Glu Glu Leu
            965
```

( 2 ) INFORMATION FOR SEQ ID NO:11:

( i ) SEQUENCE CHARACTERISTICS:
        ( A ) LENGTH: 53 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:11:

```
Lys Leu Cys Gln Thr Lys Lys Val Ile Val Glu His Thr Gly Ile Gly
 1               5                  10                  15

Val Val Phe His Pro Cys Pro Asn Cys Arg Ser Ala Thr Asp Leu Thr
                20                  25                  30

Pro Val Ile Gln Lys Leu Glu Gln Met Leu Thr Ala Gly Lys Ala Arg
            35                  40                  45

Leu Asn Ile Tyr Asp
            50
```

( 2 ) INFORMATION FOR SEQ ID NO:12:

( i ) SEQUENCE CHARACTERISTICS:
(A) LENGTH: 19 amino acids
(B) TYPE: amino acid
(C) STRANDEDNESS: single
(D) TOPOLOGY: linear ( i i ) MOLECULE TYPE: Protein ( x i ) SEQUENCE DESCRIPTION: SEQ ID NO:12:

```
Thr Ala Asp Cys Ser Asn Arg Phe Ala Val Ser Gly Lys Ala Asn Arg
 1               5                  10                  15
Lys Lys His
```

(2) INFORMATION FOR SEQ ID NO:13:

( i ) SEQUENCE CHARACTERISTICS:
(A) LENGTH: 120 amino acids
(B) TYPE: amino acid
(C) STRANDEDNESS: single
(D) TOPOLOGY: linear ( i i ) MOLECULE TYPE: Protein ( x i ) SEQUENCE DESCRIPTION: SEQ ID NO:13:

```
Gly Arg Arg Glu Val Lys Val Leu Ala Lys Thr Lys Gln Ala Glu Lys
 1               5                  10                  15
Ser Pro Ala Pro Trp Arg Ala Val Pro Cys Gly Asp Thr Lys Pro Ile
                20                  25                  30
Tyr Ile Tyr Ser Ala Tyr Ser Glu Glu Lys Glu Arg Phe Pro Tyr
         35                  40                  45
Ser Asn Gly Arg Leu Ile Ala Ala Val Phe Asp Leu Ser Ser Tyr Ser
     50                  55                  60
Gln Lys Ser Asn Ala Ser Leu Met Ala Ala Ala Pro Glu Leu Leu Glu
65                   70                  75                  80
Ala Ser Lys Ala Ala Val Asp Phe Leu Lys Gly Asn Ser Ile His Ser
                 85                  90                  95
Lys Glu Arg Ile Ile Gln Leu Leu Glu Lys Ala Glu Ala Ser Ala Ala
                100                 105                 110
Pro Lys Arg Gly Gly Asn Lys Thr
                115                 120
```

(2) INFORMATION FOR SEQ ID NO:14:

( i ) SEQUENCE CHARACTERISTICS:
(A) LENGTH: 66 amino acids
(B) TYPE: amino acid
(C) STRANDEDNESS: single
(D) TOPOLOGY: linear ( i i ) MOLECULE TYPE: Protein ( x i ) SEQUENCE DESCRIPTION: SEQ ID NO:14:

```
Phe Ile Arg Lys Asn Cys Cys Ile Ser Ile Pro Ser Arg Leu Arg Ala
 1               5                  10                  15
Ser Trp Arg Thr Gly Lys Ser Val Ile Ile Val Asp Gly Ile Lys Gln
                20                  25                  30
Glu Ala Trp Ile Thr Glu Ala Pro Glu His Gly Lys Thr Leu Val Glu
             35                  40                  45
Thr Arg Lys Gly Asp Leu Ala Arg Val Glu Phe Glu Ile Gly Tyr Lys
     50                  55                  60
Leu Asn
65
```

( 2 ) INFORMATION FOR SEQ ID NO:15:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:15:

```
Ser Glu Asn Arg Ile Arg Pro Arg Arg Lys Ala Cys Gly His
 1               5                   10
```

( 2 ) INFORMATION FOR SEQ ID NO:16:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:16:

```
Ser Thr Ala Gln His Leu Cys Val Asp Trp Cys Pro Phe Phe Ile Cys
 1               5                   10                      15
Gln Lys
```

( 2 ) INFORMATION FOR SEQ ID NO:17:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:17:

```
Asn Ala Arg Leu Thr Ile
 1               5
```

( 2 ) INFORMATION FOR SEQ ID NO:18:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:18:

```
Thr His Ala Gln Thr Asn Lys Asn Thr Ile
 1               5                   10
```

( 2 ) INFORMATION FOR SEQ ID NO:19:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:19:

Thr His Ala Gln Thr Asn Lys Asn Thr Ile
1               5                   10

( 2 ) INFORMATION FOR SEQ ID NO:20:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:20:

Ile Arg Ala Leu Ser
1               5

( 2 ) INFORMATION FOR SEQ ID NO:21:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:21:

Arg Ala Glu Gly
1

( 2 ) INFORMATION FOR SEQ ID NO:22:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:22:

Lys Asn His Gln Lys Tyr Asp Tyr
1               5

( 2 ) INFORMATION FOR SEQ ID NO:23:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:23:

Ile Cys Asn Arg Met Ala
1               5

( 2 ) INFORMATION FOR SEQ ID NO:24:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:24:

Lys Arg Lys Ala Ala Arg His Gln Thr Gly Asp
1               5                   10

( 2 ) INFORMATION FOR SEQ ID NO:25:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:25:

Cys Leu Pro Ala Ala Asp Asp Gln Gly Pro Glu Asn His Arg Ile Ile
1               5                   10                  15

Phe Gln Arg Tyr Asp Val
                20

( 2 ) INFORMATION FOR SEQ ID NO:26:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:26:

Ala Gly Arg Thr Gly Ile Arg Arg Arg Gln Arg
1               5                   10

( 2 ) INFORMATION FOR SEQ ID NO:27:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:27:

Asn Ser Arg Ser Ile Ser Pro Val Asn Gly Gln Arg Lys Gly Asn Val
1               5                   10                  15

Phe Ala Ala ( 2 ) INFORMATION FOR SEQ ID NO:28:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:28:

Gly Arg Met Phe Phe Leu
1               5

( 2 ) INFORMATION FOR SEQ ID NO:29:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear (i i) MOLECULE TYPE: None (x i) SEQUENCE DESCRIPTION: SEQ ID NO:29:

Thr Asp Arg Arg Ser Ser Arg Arg Lys Lys Ile Asp Ser Ala Asn Asp
1               5                   10                  15
Asp (2) INFORMATION FOR SEQ ID NO:30:

(i) SEQUENCE CHARACTERISTICS:
  (A) LENGTH: 29 amino acids
  (B) TYPE: amino acid
  (C) STRANDEDNESS: single
  (D) TOPOLOGY: linear (i i) MOLECULE TYPE: Protein (x i) SEQUENCE DESCRIPTION: SEQ ID NO:30:

Thr Gly Glu Phe Lys Asp Ala Lys Thr Ala Gly Arg Asn Glu Ser Ile
1               5                   10                  15
Thr Cys Leu Lys Ala Cys His Thr Phe Ala Thr Tyr Lys
                20                  25

(2) INFORMATION FOR SEQ ID NO:31:

(i) SEQUENCE CHARACTERISTICS:
  (A) LENGTH: 14 amino acids
  (B) TYPE: amino acid
  (C) STRANDEDNESS: single
  (D) TOPOLOGY: linear (i i) MOLECULE TYPE: Protein (x i) SEQUENCE DESCRIPTION: SEQ ID NO:31:

Ile Glu His Asp Thr Lys Arg Leu Ala Asp Gln Pro Leu Leu
1               5                   10

(2) INFORMATION FOR SEQ ID NO:32:

(i) SEQUENCE CHARACTERISTICS:
  (A) LENGTH: 13 amino acids
  (B) TYPE: amino acid
  (C) STRANDEDNESS: single
  (D) TOPOLOGY: linear (i i) MOLECULE TYPE: Protein (x i) SEQUENCE DESCRIPTION: SEQ ID NO:32:

Ile Asn Asn His Ala Gly Gly Gly Gly Asp Ala Val Ala
1               5                   10

(2) INFORMATION FOR SEQ ID NO:33:

(i) SEQUENCE CHARACTERISTICS:
  (A) LENGTH: 8 amino acids
  (B) TYPE: amino acid
  (C) STRANDEDNESS: single
  (D) TOPOLOGY: linear (i i) MOLECULE TYPE: Protein (x i) SEQUENCE DESCRIPTION: SEQ ID NO:33:

Lys His Asn Ser Ala Asn Lys His
1               5

(2) INFORMATION FOR SEQ ID NO:34:

( i ) SEQUENCE CHARACTERISTICS:
    ( A ) LENGTH: 51 amino acids
    ( B ) TYPE: amino acid
    ( C ) STRANDEDNESS: single
    ( D ) TOPOLOGY: linear ( i i ) MOLECULE TYPE: Protein ( x i ) SEQUENCE DESCRIPTION: SEQ ID NO:34:

```
Gln  Ser  Ile  Asn  Asn  Ile  Lys  Glu  Arg  Ser  Gln  Ile  Gly  Arg  Leu  Arg
 1                  5                        10                       15

Thr  Gln  Ser  Val  Phe  Pro  Arg  Lys  Gln  Ser  Ala  Ser  Gly  Lys  Asn  Lys
              20                        25                       30

Thr  Asn  Gly  Lys  Arg  Arg  Cys  Phe  Leu  Arg  Pro  Lys  Thr  Asn  Lys  Asn
         35                       40                  45

Ser  Ala  Leu
     50
```

( 2 ) INFORMATION FOR SEQ ID NO:35:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:35:

```
Thr  Thr  Met  Asn
 1
```

( 2 ) INFORMATION FOR SEQ ID NO:36:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:36:

```
Met  Asn  Ala  Ser  Gly  Cys  Phe  Ala  Cys  Ile  Thr  Ser  Lys  Ala  Ser  Met
 1                  5                        10                       15

Pro  His  Ser  Gln  Gln  Ser  Lys  Arg  Ala  Ile  Leu  Arg  Thr  Ala  Leu  Met
              20                        25                       30
```

( 2 ) INFORMATION FOR SEQ ID NO:37:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:37:

```
Arg  Ala  Ala  Asp  Ser
 1                  5
```

( 2 ) INFORMATION FOR SEQ ID NO:38:

( i ) SEQUENCE CHARACTERISTICS:
        ( A ) LENGTH: 42 amino acids
        ( B ) TYPE: amino acid
        ( C ) STRANDEDNESS: single (D) TOPOLOGY: linear (ii) MOLECULE TYPE: Protein (xi) SEQUENCE DESCRIPTION: SEQ ID NO:38:

| Lys | Thr | Lys | Arg | Ser | Leu | Leu | Lys | Leu | Asp | Ala | Leu | Lys | Lys | Lys | Trp |
|---|---|---|---|---|---|---|---|---|---|---|---|---|---|---|---|
| 1 | | | | 5 | | | | | 10 | | | | | 15 | |

| Ser | Met | Lys | Cys | Leu | Leu | Lys | Arg | Trp | Met | Cys | Cys | Arg | Phe | Ile | Ser |
|---|---|---|---|---|---|---|---|---|---|---|---|---|---|---|---|
| | | | 20 | | | | | 25 | | | | | 30 | | |

| Arg | Ser | Arg | Leu | Arg | Ile | Leu | Arg | Thr | Met |
|---|---|---|---|---|---|---|---|---|---|
| | | 35 | | | | | 40 | | |

(2) INFORMATION FOR SEQ ID NO:39:

(i) SEQUENCE CHARACTERISTICS:
(A) LENGTH: 24 amino acids
(B) TYPE: amino acid
(C) STRANDEDNESS: single
(D) TOPOLOGY: linear (ii) MOLECULE TYPE: Protein (xi) SEQUENCE DESCRIPTION: SEQ ID NO:39:

| Pro | Leu | Glu | Lys | Lys | Arg | Ser | Arg | Leu | Ser | Gly | Asn | Arg | Val | Arg | Cys |
|---|---|---|---|---|---|---|---|---|---|---|---|---|---|---|---|
| 1 | | | | 5 | | | | | 10 | | | | | 15 | |

| Leu | Met | Lys | Met | Ile | Ile | Arg | Leu |
|---|---|---|---|---|---|---|---|
| | | | 20 | | | | |

(2) INFORMATION FOR SEQ ID NO:40:

(i) SEQUENCE CHARACTERISTICS:
(A) LENGTH: 18 amino acids
(B) TYPE: amino acid
(C) STRANDEDNESS: single
(D) TOPOLOGY: linear (ii) MOLECULE TYPE: Protein (xi) SEQUENCE DESCRIPTION: SEQ ID NO:40:

| Arg | Lys | Ser | Ala | Leu | Ser | Met | Ser | Lys | Thr | Pro | Gly | Ser | Leu | Met | Ala |
|---|---|---|---|---|---|---|---|---|---|---|---|---|---|---|---|
| 1 | | | | 5 | | | | | 10 | | | | | 15 | |

| Pro | Leu |
|---|---|
| | |

(2) INFORMATION FOR SEQ ID NO:41:

(i) SEQUENCE CHARACTERISTICS:
(A) LENGTH: 15 amino acids
(B) TYPE: amino acid
(C) STRANDEDNESS: single
(D) TOPOLOGY: linear (ii) MOLECULE TYPE: Protein (xi) SEQUENCE DESCRIPTION: SEQ ID NO:41:

| Arg | Lys | Gln | Ser | Leu | Gly | Lys | Arg | His | Cys | His | Gln | Ala | Cys | Arg |
|---|---|---|---|---|---|---|---|---|---|---|---|---|---|---|
| 1 | | | | 5 | | | | | 10 | | | | | 15 |

(2) INFORMATION FOR SEQ ID NO:42:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: Protein (xi) SEQUENCE DESCRIPTION: SEQ ID NO:42:

Asn Glu Gly Ala
1

( 2 ) INFORMATION FOR SEQ ID NO:43:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:43:

Glu Ala Ile Leu Ile Phe
1              5

( 2 ) INFORMATION FOR SEQ ID NO:44:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:44:

Phe Val Ser Arg Ser Ile
1              5

( 2 ) INFORMATION FOR SEQ ID NO:45:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:45:

Glu Ile Glu Ala Cys Gln Thr Lys Ser Gly Glu Asn Arg
1              5                   10

( 2 ) INFORMATION FOR SEQ ID NO:46:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:46:

Gln Pro Gly Ala Asp
1              5

( 2 ) INFORMATION FOR SEQ ID NO:47:

( i ) SEQUENCE CHARACTERISTICS:
        ( A ) LENGTH: 86 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:47:

```
Asn  Tyr  Asp  Gln  Thr  Lys  Arg  Ala  Gln  Val  Met  Ile  Val  Lys  Glu  Ile
 1              5                        10                       15

Asn  Pro  His  Phe  Glu  Asp  Tyr  Val  Phe  Asn  Trp  Glu  Gln  Thr  Tyr  Gln
              20                        25                       30

Phe  Leu  Val  Gly  Gly  Tyr  Gly  Ser  Ser  Lys  Ser  Tyr  His  Thr  Ala  Leu
              35                        40                       45

Lys  Ile  Val  Leu  Lys  Leu  Leu  Lys  Glu  Lys  Arg  Thr  Ala  Leu  Val  Ile
         50                        55                       60

Arg  Glu  Val  Phe  Asp  Thr  His  Arg  Asp  Ser  Thr  Phe  Ala  Leu  Phe  Gln
 65                       70                        75                       80

Glu  Val  Ile  Glu  Glu  Leu
                    85
```

( 2 ) INFORMATION FOR SEQ ID NO:48:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:48:

```
Ser  Phe  Val  Lys  Gln  Arg  Lys  Ser  Leu  Trp  Asn  Ile  Pro  Val  Leu  Glu
 1              5                        10                       15

Leu  Phe  Phe  Ile  His  Val  Arg  Thr  Ala  Gly  Pro  Arg  Leu  Thr
              20                        25                       30
```

( 2 ) INFORMATION FOR SEQ ID NO:49:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:49:

```
Arg  Leu  Ser  Phe  Lys  Ser  Trp  Ser  Lys  Cys
 1              5                        10
```

( 2 ) INFORMATION FOR SEQ ID NO:50:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:50:

```
Gln  Arg  Glu  Lys  Arg  Gly
 1              5
```

( 2 ) INFORMATION FOR SEQ ID NO:51:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:51:

Ile Ser Met Ile Lys Gln Leu Thr Ala Leu Ile Ala Leu Leu Phe Gly
1               5                   10                  15
Lys ( 2 ) INFORMATION FOR SEQ ID NO:52:

( i ) SEQUENCE CHARACTERISTICS:
        ( A ) LENGTH: 47 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:52:

Lys Cys Trp Gln Arg Gln Asn Arg Gln Arg Lys Ala Leu Arg Arg Gly
1               5                   10                  15

Val Leu Ser Arg Ala Gly Ile Arg Asn Arg Ser Ile Phe Ile Gln Leu
            20                  25                  30

Thr Val Lys Lys Lys Lys Asp Phe Arg Thr Gln Thr Gly Gly
        35                  40                  45

( 2 ) INFORMATION FOR SEQ ID NO:53:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:53:

Leu Gln Leu Tyr Leu Thr Ser Ala Leu Ile Arg Lys Lys Ala Met Pro
1               5                   10                  15
Leu ( 2 ) INFORMATION FOR SEQ ID NO:54:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:54:

Trp Pro Leu Arg Leu Asn Cys Trp Lys Arg Leu Lys Gln Gln Leu Ile
1               5                   10                  15
Phe ( 2 ) INFORMATION FOR SEQ ID NO:55:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:55:

Lys Gly Ile Leu Phe Ile Gln Arg Ser Val Ser Phe Ser Tyr
1               5                   10

(2) INFORMATION FOR SEQ ID NO:56:

(i) SEQUENCE CHARACTERISTICS:
  (A) LENGTH: 30 amino acids
  (B) TYPE: amino acid
  (C) STRANDEDNESS: single
  (D) TOPOLOGY: linear (ii) MOLECULE TYPE: Protein (xi) SEQUENCE DESCRIPTION: SEQ ID NO:56:

Lys Lys Leu Lys Gln Ala Leu His Arg Lys Gly Glu Glu Ile Lys His
1               5                   10                  15

Asp Ser Ser Glu Lys Thr Ala Ala Tyr Arg Phe Arg His Ala
            20                  25                  30

(2) INFORMATION FOR SEQ ID NO:57:

(i) SEQUENCE CHARACTERISTICS:
  (A) LENGTH: 50 amino acids
  (B) TYPE: amino acid
  (C) STRANDEDNESS: single
  (D) TOPOLOGY: linear (ii) MOLECULE TYPE: Protein (xi) SEQUENCE DESCRIPTION: SEQ ID NO:57:

Glu Pro Ala Gly Gly Arg Glu Asn Pro Ser Leu Leu Trp Thr Ala Ser
1               5                   10                  15

Ser Lys Lys His Gly Ser Gln Lys Arg Gln Ser Met Glu Lys Arg Ser
            20                  25                  30

Ser Lys Gln Glu Arg Ala Ile Leu Leu Val Trp Asn Leu Lys Ser Ala
            35                  40                  45

Thr Asn
    50

(2) INFORMATION FOR SEQ ID NO:58:

(i) SEQUENCE CHARACTERISTICS:
  (A) LENGTH: 209 amino acids
  (B) TYPE: amino acid
  (C) STRANDEDNESS: single
  (D) TOPOLOGY: linear (ii) MOLECULE TYPE: Protein (xi) SEQUENCE DESCRIPTION: SEQ ID NO:58:

Ile Lys Ala Lys Thr Glu Tyr Val Gln Asp Gly Lys Pro Ala Asp Thr
1               5                   10                  15

Asp Gln Leu His Ser Ile Cys Ala Leu Ile Gly Val Arg Phe Leu Phe
            20                  25                  30

Ala Lys Asn Glu Glu Asp His Arg Met Gln Asp Leu Leu Phe Glu Tyr
            35                  40                  45

Lys Arg Thr Leu Lys Gln Thr Arg Ile Gln Tyr Lys Pro Leu Ala Glu
        50                  55                  60

Ala Asp Glu Ser Val Leu Ser Ala Glu Glu Leu Lys Asp Lys Lys Ile
65                  70                  75                  80

Ile Arg Asn Met Ile Thr Asp Leu Glu Tyr Val Thr Glu Trp Leu Glu
                85                  90                  95

Lys Gly Arg Gln Pro Gly Ile Arg Arg Ala Ile Asp Arg Arg Asp Val
            100                 105                 110

-continued

```
Tyr  Gln  Arg  Leu  Met  Ile  Lys  Asp  Pro  Arg  Ile  Ile  Glu  Ser  Phe  Ser
          115                 120                     125

Ser  Ala  Met  Met  Phe  Glu  Pro  Asp  Gly  Gln  Val  Ser  Glu  Glu  Asp  Arg
     130                 135                     140

Asp  Arg  Ile  Arg  Glu  Ala  Leu  Ala  Leu  Leu  Thr  Asp  Arg  Glu  Lys  Glu
145                      150                     155                          160

Met  Phe  Leu  Leu  His  Lys  Val  Glu  Cys  Phe  Ser  Tyr  Glu  Arg  Ile  Ala
               165                      170                          175

Asp  Leu  Leu  Gly  Val  Lys  Lys  Ser  Thr  Val  Gln  Thr  Thr  Ile  Lys  Arg
               180                 185                          190

Ala  Ser  Leu  Lys  Met  Gln  Arg  Gln  Gln  Glu  Glu  Met  Asn  Arg  Ser  Leu
          195                 200                     205

Ala
```

(2) INFORMATION FOR SEQ ID NO:59:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:59:

```
Lys  Leu  Val  Ile  Arg  Leu  Pro  Pro  Ile  Ser  Glu
1                   5                        10
```

(2) INFORMATION FOR SEQ ID NO:60:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:60:

```
Ser  Met  Thr  Leu  Ser  Gly  Trp  Leu  Ile  Ser  Arg  Phe  Tyr  Glu
1                   5                        10
```

(2) INFORMATION FOR SEQ ID NO:61:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:61:

```
Thr  Thr  Met  Leu  Glu  Val  Ala  Val  Met  Gln
1                   5                        10
```

(2) INFORMATION FOR SEQ ID NO:62:

(i) SEQUENCE CHARACTERISTICS:
        (A) LENGTH: 65 amino acids
        (B) TYPE: amino acid
        (C) STRANDEDNESS: single
        (D) TOPOLOGY: linear (ii) MOLECULE TYPE: Protein ( x i ) SEQUENCE DESCRIPTION: SEQ ID NO:62:

His Glu Asn Thr Thr Ala Arg Thr Ser Ile Ser Asn Leu Ser Thr Thr
1               5                   10                  15

Ser Arg Lys Asp His Lys Ser Gly Asp Cys Gly His Asn Arg Cys Phe
            20                  25                  30

Arg Glu Asn Asn Arg His Leu Glu Lys Thr Arg Gln Met Glu Arg Gly
            35                  40                  45

Ala Val Phe Cys Val Gln Lys Arg Thr Lys Thr Ala Pro Tyr Lys Gln
            50                  55                  60

Arg
65

( 2 ) INFORMATION FOR SEQ ID NO:63:

( i ) SEQUENCE CHARACTERISTICS:
    ( A ) LENGTH: 44 amino acids
    ( B ) TYPE: amino acid
    ( C ) STRANDEDNESS: single
    ( D ) TOPOLOGY: linear ( i i ) MOLECULE TYPE: None ( x i ) SEQUENCE DESCRIPTION: SEQ ID NO:63:

Thr Pro Ala Ala Val Leu Pro Val Leu Arg Gln Lys Leu Gln Cys His
1               5                   10                  15

Thr Val Ser Asn Gln Ser Gly Leu Phe Ser Gly Gln Arg Ser Cys Asp
            20                  25                  30

Gly Gln Pro Thr Leu Lys Lys Arg Lys Gly Arg Cys
            35                  40

( 2 ) INFORMATION FOR SEQ ID NO:64:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: Protein ( x i ) SEQUENCE DESCRIPTION: SEQ ID NO:64:

Lys Arg Asn Gly Gln
1               5

( 2 ) INFORMATION FOR SEQ ID NO:65:

( i ) SEQUENCE CHARACTERISTICS:
    ( A ) LENGTH: 37 amino acids
    ( B ) TYPE: amino acid
    ( C ) STRANDEDNESS: single
    ( D ) TOPOLOGY: linear ( i i ) MOLECULE TYPE: Protein ( x i ) SEQUENCE DESCRIPTION: SEQ ID NO:65:

Ser Asp Gly Cys Ala Ala Gly Leu Tyr Gln Asp Arg Val Cys Gly Tyr
1               5                   10                  15

Tyr Gly Leu Cys Asp Leu Trp Lys Lys Arg Gly Pro Gly Cys Arg Glu
            20                  25                  30

Ile Gly Ser Ala Val
            35

( 2 ) INFORMATION FOR SEQ ID NO:66:

( i ) SEQUENCE CHARACTERISTICS:
  ( A ) LENGTH: 17 amino acids
  ( B ) TYPE: amino acid
  ( C ) STRANDEDNESS: single
  ( D ) TOPOLOGY: linear ( i i ) MOLECULE TYPE: Protein ( x i ) SEQUENCE DESCRIPTION: SEQ ID NO:66:

Ser Asp Tyr Glu Gly Asn Gln Leu Cys Arg Cys Gln Arg Leu Arg Ala
1               5                   10                  15
Arg ( 2 ) INFORMATION FOR SEQ ID NO:67:

( i ) SEQUENCE CHARACTERISTICS:
    ( A ) LENGTH: 76 amino acids
    ( B ) TYPE: amino acid
    ( C ) STRANDEDNESS: single
    ( D ) TOPOLOGY: linear ( i i ) MOLECULE TYPE: Protein ( x i ) SEQUENCE DESCRIPTION: SEQ ID NO:67:

Trp His His Cys Asn Gly Ser Lys Ala Trp Glu Arg Gly Ile Ala Ile
1               5                   10                  15
Lys Leu Ala Asp Lys Met Lys Ala Leu Glu Lys Leu Ser Leu Tyr Phe
            20                  25                  30
Asp Leu Phe Pro Asp Gln Phe Lys Gln Lys Ile Glu Asn Glu Lys Leu
            35                  40                  45
Lys Leu Ala Lys Gln Lys Ala Glu Lys Thr Asp Asp Ser Gln Glu Pro
            50                  55                  60
Ile Glu Ile Met Ile Lys Arg Lys Glu Arg Lys Ser
65                  70                  75

( 2 ) INFORMATION FOR SEQ ID NO:68:

( i ) SEQUENCE CHARACTERISTICS:
    ( A ) LENGTH: 34 amino acids
    ( B ) TYPE: amino acid
    ( C ) STRANDEDNESS: single
    ( D ) TOPOLOGY: linear ( i i ) MOLECULE TYPE: Protein ( x i ) SEQUENCE DESCRIPTION: SEQ ID NO:68:

Lys Lys Ser Thr Leu Ile Ser Lys Ile Thr Cys Ser Ile Gly Ser Arg
1               5                   10                  15
Arg Thr Ser Phe Leu Ser Ala Ala Thr Ala His Pro Lys Ala Ile Ile
            20                  25                  30
Pro His ( 2 ) INFORMATION FOR SEQ ID NO:69:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: None ( x i ) SEQUENCE DESCRIPTION: SEQ ID NO:69:

Arg Lys Asn Gly Arg Pro Leu
1               5

( 2 ) INFORMATION FOR SEQ ID NO:70:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:70:

```
Ser  Gly  Arg  Cys  Ser  Ile  Pro  Ile  Gly  Ile  Arg  Pro  Ser  Pro  Cys  Phe
 1                   5                        10                       15
Lys  Arg
```

( 2 ) INFORMATION FOR SEQ ID NO:71:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:71:

```
Ala  Leu  Ser  Asn  Lys  Glu  Ser  His  Cys  Gly  Thr  Tyr  Arg  Tyr  Trp  Ser
 1                   5                        10                       15
```

( 2 ) INFORMATION FOR SEQ ID NO:72:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:72:

```
Cys  Phe  Ser  Ser  Met  Ser  Glu  Leu  Pro  Val  Arg  Asp
 1                   5                        10
```

( 2 ) INFORMATION FOR SEQ ID NO:73:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:73:

```
Leu  Asn  Ala  Cys  His  Ser  Lys  Ala  Gly  Ala  Asn  Ala  Asp  Ser  Gly  Lys
 1                   5                        10                       15
Ser  Glu  Ala  Glu  Tyr  Leu
                    20
```

( 2 ) INFORMATION FOR SEQ ID NO:74:

( i ) SEQUENCE CHARACTERISTICS:
        ( A ) LENGTH: 75 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:74:

| | | | | | | | | | | | | | | |
|---|---|---|---|---|---|---|---|---|---|---|---|---|---|---|
| Ser | Leu | Cys | Cys | Phe | Gly | Gln | Ser | Glu | Gln | Lys | Lys | Thr | Leu | Asn | Asn |
| 1 | | | | 5 | | | | | 10 | | | | | 15 |
| Gly | Ile | Arg | Thr | Thr | Gly | Ser | Glu | Ser | Val | Gly | Lys | Asp | Lys | Thr | Gly |
| | | | 20 | | | | | 25 | | | | | 30 | |
| Arg | Glu | Lys | Pro | Cys | Ala | Val | Ala | Cys | Cys | Pro | Val | Arg | Gly | Tyr | Glu |
| | | 35 | | | | 40 | | | | | | 45 | | |
| Thr | Asp | Leu | Tyr | Leu | Phe | Ser | Leu | Gln | Arg | Arg | Lys | Arg | Lys | Ile | Ser |
| | 50 | | | | | 55 | | | | | 60 | | | | |
| Val | Leu | Lys | Arg | Ala | Ala | Asp | Cys | Ser | Cys | Ile | | | | | |
| 65 | | | | | 70 | | | | | 75 | | | | | |

( 2 ) INFORMATION FOR SEQ ID NO:75:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:75:

| | | | | | | | | | | | | | | |
|---|---|---|---|---|---|---|---|---|---|---|---|---|---|---|
| Pro | Gln | Leu | Leu | Phe | Ala | Lys | Lys | Gln | Cys | Leu | Phe | Asp | Gly | Arg | Cys |
| 1 | | | | 5 | | | | | 10 | | | | | 15 | |
| Ala | | | | | | | | | | | | | | | |

( 2 ) INFORMATION FOR SEQ ID NO:76:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:76:

| | | | | |
|---|---|---|---|---|
| Ile | Ala | Gly | Ser | Val |
| 1 | | | | 5 |

( 2 ) INFORMATION FOR SEQ ID NO:77:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:77:

| | | | | | | | | | | | | | | | |
|---|---|---|---|---|---|---|---|---|---|---|---|---|---|---|---|
| Phe | Ser | Glu | Arg | Glu | Phe | Tyr | Ser | Phe | Lys | Gly | Ala | Tyr | His | Ser | Ala |
| 1 | | | | 5 | | | | | 10 | | | | | 15 | |
| Ile | Arg | Lys | Ser | | | | | | | | | | | | |
| | | | 20 | | | | | | | | | | | | |

( 2 ) INFORMATION FOR SEQ ID NO:78:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:78:

Ser Lys Arg Cys Thr Glu Lys Gly Arg Lys
1               5                   10

( 2 ) INFORMATION FOR SEQ ID NO:79:

( i ) SEQUENCE CHARACTERISTICS:
        ( A ) LENGTH: 61 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:79:

Asn Met Ile His Pro Lys Lys Leu Leu His Ile Asp Ser Val Thr Leu
1               5                   10                  15

Lys Ser Gln Leu Glu Asp Gly Lys Ile Arg His Tyr Cys Gly Arg His
                20                  25                  30

Gln Ala Arg Ser Met Asp His Arg Ser Ala Arg Ala Trp Lys Asn Ala
            35                  40                  45

Arg Arg Asn Lys Lys Gly Arg Ser Cys Ser Cys Gly Ile
        50                  55                  60

( 2 ) INFORMATION FOR SEQ ID NO:80:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:80:

Asn Arg Leu Gln Ile Lys Leu Lys Arg Lys Gln Asn Thr Ser Lys Thr
1               5                   10                  15

Glu Ser Leu Arg Thr Leu Ile Asn Cys Thr Ala Phe Val Arg
                20                  25                  30

( 2 ) INFORMATION FOR SEQ ID NO:81:

( i ) SEQUENCE CHARACTERISTICS:
        ( A ) LENGTH: 49 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:81:

Leu Val Ser Val Phe Tyr Leu Pro Lys Met Arg Arg Ile Ile Glu Cys
1               5                   10                  15

Lys Thr Tyr Tyr Leu Asn Ile Asn Ala Arg Ser Asn Lys Gln Glu Tyr
                20                  25                  30

Asn Ile Asn Arg Ser Leu Arg Gln Met Asn Pro Cys Ser Gln Leu Lys
            35                  40                  45

Ser ( 2 ) INFORMATION FOR SEQ ID NO:82:

( i ) SEQUENCE CHARACTERISTICS:
        ( A ) LENGTH: 8 amino acids
        ( B ) TYPE: amino acid ( C ) STRANDEDNESS: single
( D ) TOPOLOGY: linear ( i i ) MOLECULE TYPE: Protein ( x i ) SEQUENCE DESCRIPTION: SEQ ID NO:82:

Arg Ile Lys Lys Ser Ser Glu Ile
1               5

( 2 ) INFORMATION FOR SEQ ID NO:83:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: Protein ( x i ) SEQUENCE DESCRIPTION: SEQ ID NO:83:

Leu Leu Ile Leu Asn Met
1               5

( 2 ) INFORMATION FOR SEQ ID NO:84:

( i ) SEQUENCE CHARACTERISTICS:
( A ) LENGTH: 24 amino acids
( B ) TYPE: amino acid
( C ) STRANDEDNESS: single
( D ) TOPOLOGY: linear ( i i ) MOLECULE TYPE: Protein ( x i ) SEQUENCE DESCRIPTION: SEQ ID NO:84:

Gln Asn Gly Leu Lys Lys Glu Gly Ser Pro Ala Ser Asp Gly Arg Leu
1               5                   10                  15
Thr Gly Val Met Phe Thr Ser Gly
            20

( 2 ) INFORMATION FOR SEQ ID NO:85:

( i ) SEQUENCE CHARACTERISTICS:
( A ) LENGTH: 13 amino acids
( B ) TYPE: amino acid
( C ) STRANDEDNESS: single
( D ) TOPOLOGY: linear ( i i ) MOLECULE TYPE: Protein ( x i ) SEQUENCE DESCRIPTION: SEQ ID NO:85:

Ser Arg Thr Arg Glu Ser Ser Asn His Phe Pro Ala Leu
1               5                   10

( 2 ) INFORMATION FOR SEQ ID NO:86:

( i ) SEQUENCE CHARACTERISTICS:
( A ) LENGTH: 19 amino acids
( B ) TYPE: amino acid
( C ) STRANDEDNESS: single
( D ) TOPOLOGY: linear ( i i ) MOLECULE TYPE: Protein ( x i ) SEQUENCE DESCRIPTION: SEQ ID NO:86:

Cys Leu Ser Arg Thr Asp Arg Tyr Gln Lys Lys Thr Glu Ile Glu Phe
1               5                   10                  15
Glu Lys His

-continued ( 2 ) INFORMATION FOR SEQ ID NO:87:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:87:

Arg Thr Glu Lys Arg Lys Cys Phe Cys Cys Ile Arg
1               5                   10

( 2 ) INFORMATION FOR SEQ ID NO:88:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:88:

Asn Val Phe Leu Met Asn Gly Ser Pro Ile Phe Ser Ala
1               5                   10

( 2 ) INFORMATION FOR SEQ ID NO:89:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:89:

Lys Asn Arg Gln Cys Lys Arg Arg Leu Asn Gly Arg Val
1               5                   10

( 2 ) INFORMATION FOR SEQ ID NO:90:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:90:

Arg Cys Lys Asp Ser Arg Lys Lys
1               5

( 2 ) INFORMATION FOR SEQ ID NO:91:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:91:

Ile Asp His Leu Pro Glu Ser Leu Ser Tyr Val Cys His Leu
1               5                   10

( 2 ) INFORMATION FOR SEQ ID NO:92:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:92:

Val Asn Arg Ala
1

( 2 ) INFORMATION FOR SEQ ID NO:93:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:93:

Ser Ala Ala Phe Met Asn Lys Gln Pro Cys Trp Arg Trp Arg
1               5                   10

( 2 ) INFORMATION FOR SEQ ID NO:94:

( i ) SEQUENCE CHARACTERISTICS:
        ( A ) LENGTH: 213 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:94:

Cys Ser Ser Met Lys Thr Gln Gln Arg Glu Gln Ala Leu Ala Ile Tyr
1               5                   10                  15

Gln Gln His Gln Gly Lys Ile Thr Asn Arg Ala Ile Ala Asp Thr Ile
                20                  25                  30

Gly Val Ser Ala Lys Thr Ile Gly Ile Trp Lys Lys Gln Asp Lys Trp
            35                  40                  45

Lys Glu Ala Leu Phe Ser Ala Ser Lys Asn Glu Gln Lys Gln Arg Pro
    50                  55                  60

Ile Asn Asn Asp Glu Leu Asn Glu Arg Gln Arg Leu Phe Cys Leu Tyr
65                  70                  75                  80

Tyr Val Lys Ser Phe Asn Ala Thr Gln Ser Ala Ile Lys Ala Gly Tyr
                85                  90                  95

Ser Pro Asp Ser Ala His Val Thr Gly Ser Arg Leu Leu Lys Asn Glu
                100                 105                 110

Lys Val Ala Ala Glu Ile Arg Arg Ile Lys Lys Glu Met Val Asn Glu
            115                 120                 125

Met Phe Ile Glu Ala Met Asp Val Leu Gln Val Tyr Ile Lys Ile Ala
    130                 135                 140

Phe Ala Asp Ile Thr Asp Tyr Val Thr Phe Gly Lys Lys Glu Val Gln
145                 150                 155                 160

Ala Val Gly Lys Ser Gly Pro Leu Phe Asp Glu Asp Asn Pro Ile
                165                 170                 175

Met Lys Glu Ile Ser Phe Val Asp Val Lys Asp Ser Gly Leu Val Asp
                180                 185                 190

Gly Thr Ile Val Thr Glu Ala Lys Leu Gly Lys Glu Ala Leu Pro Ser
            195                 200                 205

Ser Leu Gln Ile Lys
    210

( 2 ) INFORMATION FOR SEQ ID NO:95:

( i ) SEQUENCE CHARACTERISTICS:
                ( A ) LENGTH: 25 amino acids
                ( B ) TYPE: amino acid
                ( C ) STRANDEDNESS: single
                ( D ) TOPOLOGY: linear ( i i ) MOLECULE TYPE: None ( x i ) SEQUENCE DESCRIPTION: SEQ ID NO:95:

Arg Arg Leu Arg Ser Tyr Pro Tyr Ile Leu Ile Cys Phe Gln Ile Asn
 1               5                  10                  15

Leu Asn Lys Lys Leu Lys Met Arg Asn
            20                  25

( 2 ) INFORMATION FOR SEQ ID NO:96:

( i ) SEQUENCE CHARACTERISTICS:
                ( A ) LENGTH: 19 amino acids
                ( B ) TYPE: amino acid
                ( C ) STRANDEDNESS: single
                ( D ) TOPOLOGY: linear ( i i ) MOLECULE TYPE: None ( x i ) SEQUENCE DESCRIPTION: SEQ ID NO:96:

Ser Leu Pro Asn Lys Lys Arg Arg Lys Gln Met Thr Ala Arg Ser Arg
 1               5                  10                  15

Leu Lys Leu ( 2 ) INFORMATION FOR SEQ ID NO:97:

( i ) SEQUENCE CHARACTERISTICS:
                ( A ) LENGTH: 83 amino acids
                ( B ) TYPE: amino acid
                ( C ) STRANDEDNESS: single
                ( D ) TOPOLOGY: linear ( i i ) MOLECULE TYPE: Protein ( x i ) SEQUENCE DESCRIPTION: SEQ ID NO:97:

Ser Asn Glu Lys Ser Ala Ser His Asp Cys Lys Arg Asn Gln Pro Ser
 1               5                  10                  15

Phe Arg Arg Leu Arg Val Gln Leu Gly Ala Asp Val Pro Val Ser Cys
            20                  25                  30

Arg Arg Leu Arg Leu Ile Gln Lys Leu Ser Tyr Arg Ile Glu Asn Arg
            35                  40                  45

Ala Lys Ala Ala Glu Gly Lys Thr Asp Gly Pro Cys Asp Pro Gly Gly
        50              55                  60

Val Arg Tyr Pro Ser Gly Phe Asp Leu Arg Leu Val Ser Arg Gly Asp
 65                     70                  75                  80

Arg Arg Ala ( 2 ) INFORMATION FOR SEQ ID NO:98:

( i ) SEQUENCE CHARACTERISTICS:
                ( A ) LENGTH: 34 amino acids
                ( B ) TYPE: amino acid
                ( C ) STRANDEDNESS: single (D) TOPOLOGY: linear (ii) MOLECULE TYPE: Protein (xi) SEQUENCE DESCRIPTION: SEQ ID NO:98:

```
Glu Leu Phe Asp His Leu Leu Lys Gln Gly Glu Gly Arg Ile Pro Met
1               5                   10                  15
Gly Ile Glu His Leu Pro Asp His Lys Gly Arg Pro Phe Phe Leu Gln
                20                  25                  30
Gln Leu
```

(2) INFORMATION FOR SEQ ID NO:99:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:99:

```
His Asp Phe Gln Cys Gly Met Ile Ala Phe Gly
1               5                   10
```

(2) INFORMATION FOR SEQ ID NO:100:

(i) SEQUENCE CHARACTERISTICS:
        (A) LENGTH: 67 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:100:

```
Ala Val Ala Ala Asp Lys Lys Leu Val Arg Leu Leu Pro Ile Glu His
1               5                   10                  15
Val Ile Phe Glu Met Arg Val Asp Phe Phe Tyr Asn His Asp Leu Arg
                20                  25                  30
Ser Phe Arg Leu Ile Ile Ile Ser Ile Gly Ser Trp Leu Ser Ser Val
                35              40                  45
Phe Ser Ala Phe Cys Leu Ala Ser Phe Asn Phe Ser Phe Ser Ile Phe
    50              55                  60
Cys Leu Asn
65
```

(2) INFORMATION FOR SEQ ID NO:101:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:101:

```
Ser Gly Asn Lys Ser Lys Tyr Lys Asp Ser Phe Ser Ser Ala Phe Ile
1               5                   10                  15
Leu Ser Ala Ser Leu Met Ala Met Pro Leu Ser Gln Ala Leu Leu Pro
                20                  25                  30
Leu Gln Trp Cys His Gln Arg Ala Arg Ser Leu
                35                  40
```

( 2 ) INFORMATION FOR SEQ ID NO:102:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:102:

His Arg Gln Ser
1

( 2 ) INFORMATION FOR SEQ ID NO:103:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:103:

Ser Asp Tyr His Leu His Gln Thr Ala Asp Pro Ile Ser Arg Gln Pro
1               5                   10                  15
Gly Pro Leu Phe Phe Gln Arg Ser His Ser Pro
            20                  25

( 2 ) INFORMATION FOR SEQ ID NO:104:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:104:

Tyr Pro Gln Thr Arg Ser
1               5

( 2 ) INFORMATION FOR SEQ ID NO:105:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:105:

Tyr Lys Pro Ala Ala His Pro Ser Leu Gln
1               5                   10

( 2 ) INFORMATION FOR SEQ ID NO:106:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:106:

Pro Phe Leu Phe
1

( 2 ) INFORMATION FOR SEQ ID NO:107:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:107:

Phe Gln Gln Arg Pro Phe Arg Phe Leu Arg Val Gly Cys Pro Ser His
1             5                   10                  15

Glu Arg Cys Pro Glu Asn Ser Pro Leu
            20                  25

( 2 ) INFORMATION FOR SEQ ID NO:108:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:108:

Leu Leu Thr Val Trp His
1             5

( 2 ) INFORMATION FOR SEQ ID NO:109:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:109:

Arg Asn Thr Gly Lys Thr Ala Ala Gly Val His Leu Ile His Arg Cys
1             5                   10                  15

Leu ( 2 ) INFORMATION FOR SEQ ID NO:110:

( i ) SEQUENCE CHARACTERISTICS:
        ( A ) LENGTH: 40 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:110:

Gly Ala Val Phe Val Arg Phe Trp Thr Gln Lys Thr Ala Pro Leu Ser
1             5                   10                  15

Ile Cys Leu Val Phe Ser Arg Cys Arg Leu Phe Ser Arg Lys His Arg
            20                  25                  30

Leu Cys Pro Gln Ser Pro Asp Leu
            35                  40

( 2 ) INFORMATION FOR SEQ ID NO:111:

( i ) SEQUENCE CHARACTERISTICS:
  ( A ) LENGTH: 33 amino acids
  ( B ) TYPE: amino acid
  ( C ) STRANDEDNESS: single
  ( D ) TOPOLOGY: linear ( i i ) MOLECULE TYPE: Protein ( x i ) SEQUENCE DESCRIPTION: SEQ ID NO:111:

| Ser | Phe | Leu | Asp | Val | Val | Asp | Arg | Leu | Leu | Met | Leu | Val | Arg | Ala | Val |
|---|---|---|---|---|---|---|---|---|---|---|---|---|---|---|---|
| 1 |  |  |  | 5 |  |  |  |  | 10 |  |  |  |  | 15 |  |
| Val | Phe | Ser | Cys | Tyr | Cys | Ile | Thr | Ala | Thr | Ser | Ser | Met | Val | Val | Tyr |
|  |  |  | 20 |  |  |  |  | 25 |  |  |  |  | 30 |  |  |
| Ser |

( 2 ) INFORMATION FOR SEQ ID NO:112:

( i ) SEQUENCE CHARACTERISTICS:
  ( A ) LENGTH: 62 amino acids
  ( B ) TYPE: amino acid
  ( C ) STRANDEDNESS: single
  ( D ) TOPOLOGY: linear ( i i ) MOLECULE TYPE: Protein ( x i ) SEQUENCE DESCRIPTION: SEQ ID NO:112:

| Lys | Arg | Leu | Ile | Ser | Gln | Pro | Leu | Ser | Val | Met | Leu | Tyr | Ser | Leu | Ile |
|---|---|---|---|---|---|---|---|---|---|---|---|---|---|---|---|
| 1 |  |  |  | 5 |  |  |  |  | 10 |  |  |  |  | 15 |  |
| Gly | Gly | Lys | Arg | Met | Thr | Ser | Phe | Gln | Ala | Ser | Asp | Arg | Phe | Ile | Ser |
|  |  |  | 20 |  |  |  |  | 25 |  |  |  |  | 30 |  |  |
| Ser | Cys | Cys | Leu | Cys | Ile | Phe | Lys | Leu | Ala | Arg | Leu | Ile | Val | Val | Cys |
|  |  |  | 35 |  |  |  |  | 40 |  |  |  |  | 45 |  |  |
| Thr | Val | Asp | Phe | Phe | Thr | Pro | Arg | Arg | Ser | Ala | Ile | Arg | Ser |
|  |  | 50 |  |  |  |  | 55 |  |  |  |  | 60 |  |

( 2 ) INFORMATION FOR SEQ ID NO:113:

( i ) SEQUENCE CHARACTERISTICS:
  ( A ) LENGTH: 58 amino acids
  ( B ) TYPE: amino acid
  ( C ) STRANDEDNESS: single
  ( D ) TOPOLOGY: linear ( i i ) MOLECULE TYPE: Protein ( x i ) SEQUENCE DESCRIPTION: SEQ ID NO:113:

| Glu | Lys | His | Ser | Thr | Leu | Cys | Ser | Lys | Asn | Ile | Ser | Phe | Ser | Leu | Ser |
|---|---|---|---|---|---|---|---|---|---|---|---|---|---|---|---|
| 1 |  |  |  | 5 |  |  |  |  | 10 |  |  |  |  | 15 |  |
| Val | Asn | Arg | Ala | Asn | Ala | Ser | Arg | Ile | Leu | Ser | Leu | Ser | Ser | Ser | Asp |
|  |  |  | 20 |  |  |  |  | 25 |  |  |  |  | 30 |  |  |
| Thr | Cys | Pro | Ser | Gly | Ser | Asn | Ile | Ile | Ala | Leu | Glu | Asn | Asp | Ser | Met |
|  |  |  | 35 |  |  |  |  | 40 |  |  |  |  | 45 |  |  |
| Ile | Leu | Gly | Ser | Leu | Ile | Ile | Ser | Arg | Trp |
|  |  |  | 50 |  |  |  |  | 55 |  |  |

( 2 ) INFORMATION FOR SEQ ID NO:114:

( i ) SEQUENCE CHARACTERISTICS:
  ( A ) LENGTH: 73 amino acids
  ( B ) TYPE: amino acid
  ( C ) STRANDEDNESS: single
  ( D ) TOPOLOGY: linear ( i i ) MOLECULE TYPE: Protein ( x i ) SEQUENCE DESCRIPTION: SEQ ID NO:114:

| Thr | Ser | Arg | Arg | Ser | Ile | Ala | Arg | Leu | Met | Pro | Gly | Cys | Leu | Pro | Phe |
|---|---|---|---|---|---|---|---|---|---|---|---|---|---|---|---|
| 1 | | | | 5 | | | | | 10 | | | | | 15 | |

| Ser | Ser | His | Ser | Val | Thr | Tyr | Ser | Arg | Ser | Val | Ile | Ile | Phe | Leu | Met |
|---|---|---|---|---|---|---|---|---|---|---|---|---|---|---|---|
| | | | 20 | | | | | 25 | | | | | 30 | | |

| Ile | Phe | Leu | Ser | Phe | Ser | Ser | Ser | Ala | Glu | Ser | Thr | Asp | Ser | Ser | Ala |
|---|---|---|---|---|---|---|---|---|---|---|---|---|---|---|---|
| | | 35 | | | | | 40 | | | | | 45 | | | |

| Ser | Ala | Ser | Gly | Leu | Tyr | Cys | Ile | Leu | Val | Cys | Leu | Ser | Val | Arg | Leu |
|---|---|---|---|---|---|---|---|---|---|---|---|---|---|---|---|
| | 50 | | | | | 55 | | | | | 60 | | | | |

| Tyr | Ser | Asn | Ser | Lys | Ser | Cys | Ile | Leu |
|---|---|---|---|---|---|---|---|---|
| 65 | | | | | 70 | | | |

( 2 ) INFORMATION FOR SEQ ID NO:115:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i i ) MOLECULE TYPE: Protein ( x i ) SEQUENCE DESCRIPTION: SEQ ID NO:115:

| Ser | Ser | Ser | Phe | Leu | Ala | Asn | Lys | Lys | Arg | Thr | Pro | Ile | Asn | Ala | Gln |
|---|---|---|---|---|---|---|---|---|---|---|---|---|---|---|---|
| 1 | | | | 5 | | | | | 10 | | | | | 15 | |

| Met | Leu | Cys | Ser |
|---|---|---|---|
| | | | 20 |

( 2 ) INFORMATION FOR SEQ ID NO:116:

( i ) SEQUENCE CHARACTERISTICS:
    ( A ) LENGTH: 17 amino acids
    ( B ) TYPE: amino acid
    ( C ) STRANDEDNESS: single
    ( D ) TOPOLOGY: linear ( i i ) MOLECULE TYPE: Protein ( x i ) SEQUENCE DESCRIPTION: SEQ ID NO:116:

| Ser | Val | Ser | Ala | Gly | Phe | Pro | Ser | Trp | Thr | Tyr | Ser | Val | Phe | Ala | Leu |
|---|---|---|---|---|---|---|---|---|---|---|---|---|---|---|---|
| 1 | | | | 5 | | | | | 10 | | | | | 15 | |

| Ile |
|---|
| |

( 2 ) INFORMATION FOR SEQ ID NO:117:

( i ) SEQUENCE CHARACTERISTICS:
    ( A ) LENGTH: 50 amino acids
    ( B ) TYPE: amino acid
    ( C ) STRANDEDNESS: single
    ( D ) TOPOLOGY: linear ( i i ) MOLECULE TYPE: Protein ( x i ) SEQUENCE DESCRIPTION: SEQ ID NO:117:

| Phe | Val | Ala | Asp | Phe | Lys | Phe | His | Thr | Ser | Lys | Ile | Ala | Leu | Ser | Cys |
|---|---|---|---|---|---|---|---|---|---|---|---|---|---|---|---|
| 1 | | | | 5 | | | | | 10 | | | | | 15 | |

| Phe | Asp | Glu | Arg | Phe | Ser | Met | Leu | Trp | Arg | Phe | Cys | Asp | Pro | Cys | Phe |
|---|---|---|---|---|---|---|---|---|---|---|---|---|---|---|---|
| | | | 20 | | | | | 25 | | | | | 30 | | |

| Leu | Leu | Asp | Ala | Val | His | Asn | Asn | Asp | Gly | Phe | Ser | Arg | Pro | Pro | Ala |
|---|---|---|---|---|---|---|---|---|---|---|---|---|---|---|---|
| | | | 35 | | | | | 40 | | | | | 45 | | |

| Gly | Ser |
|---|---|
| | 50 |

( 2 ) INFORMATION FOR SEQ ID NO:118:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:118:

```
Arg  Asn  Arg  Tyr  Ala  Ala  Val  Phe  Ser  Asp  Glu  Ser  Cys  Phe  Ile  Ser
 1                  5                        10                       15
Ser  Pro  Phe  Arg  Cys  Ser  Ala  Cys  Phe  Ser  Phe  Phe
                20                       25
```

( 2 ) INFORMATION FOR SEQ ID NO:119:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:119:

```
Leu  Asn  Asp  Thr  Leu  Leu
 1                  5
```

( 2 ) INFORMATION FOR SEQ ID NO:120:

( i ) SEQUENCE CHARACTERISTICS:
        ( A ) LENGTH: 46 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:120:

```
Met  Asn  Arg  Ile  Pro  Phe  Gln  Lys  Ile  Asn  Cys  Cys  Phe  Arg  Arg  Phe
 1                  5                        10                       15
Gln  Gln  Phe  Arg  Arg  Ser  Gly  His  Gln  Arg  Gly  Ile  Ala  Phe  Leu  Arg
                20                       25                       30
Ile  Arg  Ala  Glu  Val  Lys  Tyr  Ser  Cys  Asn  Gln  Pro  Pro  Val
                35                       40                       45
```

( 2 ) INFORMATION FOR SEQ ID NO:121:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:121:

```
Val  Arg  Lys  Ser  Phe  Phe  Phe  Phe  Phe  Thr  Val  Ser
 1                  5                        10
```

( 2 ) INFORMATION FOR SEQ ID NO:122:

( i ) SEQUENCE CHARACTERISTICS:
        ( A ) LENGTH: 82 amino acids
        ( B ) TYPE: amino acid
        ( C ) STRANDEDNESS: single
        ( D ) TOPOLOGY: linear (i i) MOLECULE TYPE: Protein (x i) SEQUENCE DESCRIPTION: SEQ ID NO:122:

| Ile | Asn | Ile | Asp | Arg | Phe | Arg | Ile | Pro | Ala | Arg | Asp | Ser | Thr | Gln | Arg |
|---|---|---|---|---|---|---|---|---|---|---|---|---|---|---|---|
| 1 | | | | 5 | | | | | 10 | | | | | 15 | |
| Arg | Arg | Ala | Phe | Leu | Cys | Leu | Phe | Cys | Leu | Cys | Gln | His | Phe | His | Phe |
| | | | 20 | | | | 25 | | | | | 30 | | | |
| Pro | Ser | Ser | Leu | Tyr | His | Cys | Ser | Met | Phe | Phe | Ser | Val | Arg | Phe | Ala |
| | | 35 | | | | 40 | | | | | 45 | | | | |
| Arg | Asn | Ser | Lys | Ala | Ile | Arg | Ala | Val | Ser | Cys | Leu | Ile | Ile | Asp | Ile |
| | 50 | | | | | 55 | | | | | 60 | | | | |
| Gln | Pro | Arg | Phe | Ser | Arg | Cys | Gln | His | Leu | Leu | Gln | Leu | Leu | Asn | Asp |
| 65 | | | | | 70 | | | | 75 | | | | | | 80 |
| Arg | Arg | | | | | | | | | | | | | | |

(2) INFORMATION FOR SEQ ID NO:123:

(i) SEQUENCE CHARACTERISTICS:
        (A) LENGTH: 30 amino acids
        (B) TYPE: amino acid
        (C) STRANDEDNESS: single
        (D) TOPOLOGY: linear (i i) MOLECULE TYPE: Protein (x i) SEQUENCE DESCRIPTION: SEQ ID NO:123:

| Val | Ser | Arg | Gly | Pro | Ala | Val | Arg | Thr | Trp | Met | Lys | Asn | Asn | Ser | Asn |
|---|---|---|---|---|---|---|---|---|---|---|---|---|---|---|---|
| 1 | | | | 5 | | | | | 10 | | | | | 15 | |
| Thr | Gly | Met | Phe | His | Asn | Asp | Phe | Leu | Cys | Leu | Thr | Lys | Leu | | |
| | | | 20 | | | | | 25 | | | | | 30 | | |

(2) INFORMATION FOR SEQ ID NO:124:

(i) SEQUENCE CHARACTERISTICS:
        (A) LENGTH: 6 amino acids
        (B) TYPE: amino acid
        (C) STRANDEDNESS: single
        (D) TOPOLOGY: linear (i i) MOLECULE TYPE: Protein (x i) SEQUENCE DESCRIPTION: SEQ ID NO:124:

| Ser | Ser | Ser | Ile | Thr | Ser |
|---|---|---|---|---|---|
| 1 | | | | 5 | |

(2) INFORMATION FOR SEQ ID NO:125:

(i) SEQUENCE CHARACTERISTICS:
        (A) LENGTH: 34 amino acids
        (B) TYPE: amino acid
        (C) STRANDEDNESS: single
        (D) TOPOLOGY: linear (i i) MOLECULE TYPE: Protein (x i) SEQUENCE DESCRIPTION: SEQ ID NO:125:

| Asn | Lys | Ala | Lys | Val | Glu | Ser | Arg | Trp | Val | Ser | Asn | Thr | Ser | Arg | Ile |
|---|---|---|---|---|---|---|---|---|---|---|---|---|---|---|---|
| 1 | | | | 5 | | | | | 10 | | | | | 15 | |
| Thr | Arg | Ala | Val | Arg | Phe | Ser | Phe | Ser | Ser | Phe | Ser | Thr | Ile | Phe | Asn |
| | | | 20 | | | | | 25 | | | | | 30 | | |
| Ala | Val | | | | | | | | | | | | | | |

(2) INFORMATION FOR SEQ ID NO:126:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: Protein ( x i ) SEQUENCE DESCRIPTION: SEQ ID NO:126:

Leu Leu Asp Glu Pro
1               5

( 2 ) INFORMATION FOR SEQ ID NO:127:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( i i ) MOLECULE TYPE: Protein ( x i ) SEQUENCE DESCRIPTION: SEQ ID NO:127:

Pro Pro Thr Arg Asn Trp Tyr Val Cys Ser Gln Leu Asn Thr
1               5                   10

( 2 ) INFORMATION FOR SEQ ID NO:128:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( i i ) MOLECULE TYPE: Protein ( x i ) SEQUENCE DESCRIPTION: SEQ ID NO:128:

Gly Leu Ile Ser Phe Thr Ile Met Thr Cys Ala Leu Phe Val
1               5                   10

( 2 ) INFORMATION FOR SEQ ID NO:129:

( i ) SEQUENCE CHARACTERISTICS:
    ( A ) LENGTH: 27 amino acids
    ( B ) TYPE: amino acid
    ( C ) STRANDEDNESS: single
    ( D ) TOPOLOGY: linear ( i i ) MOLECULE TYPE: Protein ( x i ) SEQUENCE DESCRIPTION: SEQ ID NO:129:

Phe Gln Ser Ala Pro Gly Cys His Leu Phe Ser Pro Leu Phe Val Trp
1               5                   10                  15
Gln Ala Ser Ile Ser His Phe Gln Phe Phe Val
            20              25

( 2 ) INFORMATION FOR SEQ ID NO:130:

( i ) SEQUENCE CHARACTERISTICS:
    ( A ) LENGTH: 22 amino acids
    ( B ) TYPE: amino acid
    ( C ) STRANDEDNESS: single
    ( D ) TOPOLOGY: linear ( i i ) MOLECULE TYPE: Protein ( x i ) SEQUENCE DESCRIPTION: SEQ ID NO:130:

Ile Asp Leu Glu Thr Asn Gln Asn Ile Arg Ile Ala Ser Gln Ala Pro
1               5                   10                  15

Ser Phe Tyr Leu Gln Ala
                20

(2) INFORMATION FOR SEQ ID NO:131:

(i) SEQUENCE CHARACTERISTICS:
        (A) LENGTH: 98 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:131:

Trp Gln Cys Leu Phe Pro Lys Leu Cys Phe Arg Tyr Asn Gly Ala Ile
 1               5                  10                 15

Asn Glu Pro Gly Val Phe Asp Ile Asp Lys Ala Asp Phe Leu His Asn
               20                  25                 30

Arg Ile Ile Ile Phe Ile Lys Gln Arg Thr Arg Phe Pro Asp Ser Leu
           35                  40                 45

Asp Leu Phe Phe Ser Lys Gly His Ile Val Arg Asn Ile Arg Lys Arg
       50                  55                 60

Asp Leu Asp Ile Asn Leu Gln His Ile His Arg Phe Asn Lys His Phe
65                  70                  75                 80

Ile Asp His Phe Phe Phe Asn Ala Ser Asn Phe Ser Ser Asp Leu Phe
               85                  90                 95

Val Phe (2) INFORMATION FOR SEQ ID NO:132:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:132:

Glu Ser Ala Ala Arg His Met Ser Ala Val Arg Arg Ile Ala Arg Phe
 1               5                  10                 15

Asp Cys (2) INFORMATION FOR SEQ ID NO:133:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:133:

Leu Cys Gly Ile Glu Ala Phe Asp Val Ile Gln Ala Lys Gln Pro Leu
 1               5                  10                 15

Ala Phe Ile (2) INFORMATION FOR SEQ ID NO:134:

(i) SEQUENCE CHARACTERISTICS:
        (A) LENGTH: 46 amino acids
        (B) TYPE: amino acid
        (C) STRANDEDNESS: single (D) TOPOLOGY: linear (i i) MOLECULE TYPE: Protein (x i) SEQUENCE DESCRIPTION: SEQ ID NO:134:

```
Phe Ile Val Val Tyr Arg Ala Leu Phe Leu Phe Val Phe Gly Arg Arg
1               5                   10                  15

Lys Gln Arg Leu Phe Pro Phe Val Leu Phe Phe Pro Asp Ala Asp Cys
                20                  25                  30

Phe Arg Gly Asn Thr Asp Cys Val Arg Asn Arg Pro Ile Cys
                35                  40                  45
```

(2) INFORMATION FOR SEQ ID NO:135:

(i) SEQUENCE CHARACTERISTICS:
        (A) LENGTH: 10 amino acids
        (B) TYPE: amino acid
        (C) STRANDEDNESS: single
        (D) TOPOLOGY: linear (i i) MOLECULE TYPE: Protein (x i) SEQUENCE DESCRIPTION: SEQ ID NO:135:

```
Asp Leu Ser Leu Met Leu Leu Ile Asp Cys
1               5                   10
```

(2) INFORMATION FOR SEQ ID NO:136:

(i) SEQUENCE CHARACTERISTICS:
        (A) LENGTH: 26 amino acids
        (B) TYPE: amino acid
        (C) STRANDEDNESS: single
        (D) TOPOLOGY: linear (i i) MOLECULE TYPE: Protein (x i) SEQUENCE DESCRIPTION: SEQ ID NO:136:

```
Cys Leu Phe Ala Leu Leu Cys Phe His Ala Thr Ala Ser Pro Pro Pro
1               5                   10                  15

Pro Ala Trp Leu Phe Ile His Lys Ser Gly
                20                  25
```

(2) INFORMATION FOR SEQ ID NO:137:

(i) SEQUENCE CHARACTERISTICS:
        (A) LENGTH: 12 amino acids
        (B) TYPE: amino acid
        (C) STRANDEDNESS: single
        (D) TOPOLOGY: linear (i i) MOLECULE TYPE: Protein (x i) SEQUENCE DESCRIPTION: SEQ ID NO:137:

```
Ser Ala Ser Arg Leu Val Ser Cys Ser Ile His Leu
1               5                   10
```

(2) INFORMATION FOR SEQ ID NO:138:

(i) SEQUENCE CHARACTERISTICS:
        (A) LENGTH: 4 amino acids
        (B) TYPE: amino acid
        (C) STRANDEDNESS: single
        (D) TOPOLOGY: linear (i i) MOLECULE TYPE: Protein (x i) SEQUENCE DESCRIPTION: SEQ ID NO:138:

Val Ala Asn Val
1

(2) INFORMATION FOR SEQ ID NO:139:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:139:

Gln Ala Phe Arg Gln Val Ile Asp Ser Phe Leu Pro Ala Val Phe Ala
1               5                   10                  15

Ser Leu Asn Ser Pro Val
            20

(2) INFORMATION FOR SEQ ID NO:140:

(i) SEQUENCE CHARACTERISTICS:
        (A) LENGTH: 59 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:140:

Ser Ser Phe Ala Leu Ser Ile Phe Leu Arg Arg Glu Asp Arg Arg Ser
1               5                   10                  15

Val His Lys Lys Asn Ile Leu Pro Tyr Ala Ala Lys Thr Phe Pro Phe
            20                  25                  30

Leu Cys Pro Leu Thr Gly Leu Met Leu Leu Glu Phe Tyr Leu Cys Leu
            35              40                  45

Leu Leu Ile Pro Val Arg Pro Ala Gln Thr Ser
            50              55

(2) INFORMATION FOR SEQ ID NO:141:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:141:

Arg Trp Lys Met Ile Arg
1               5

(2) INFORMATION FOR SEQ ID NO:142:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:142:

Phe Ser Gly Pro
1

( 2 ) INFORMATION FOR SEQ ID NO:143:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( i i ) MOLECULE TYPE: None ( x i ) SEQUENCE DESCRIPTION: SEQ ID NO:143:

```
Ser  Ser  Ala  Ala  Gly  Lys  His  His  Ala  Gly  Gln  Ser  Pro  Val
1                   5                        10
```

( 2 ) INFORMATION FOR SEQ ID NO:144:

( i ) SEQUENCE CHARACTERISTICS:
    ( A ) LENGTH: 17 amino acids
    ( B ) TYPE: amino acid
    ( C ) STRANDEDNESS: single
    ( D ) TOPOLOGY: linear ( i i ) MOLECULE TYPE: Protein ( x i ) SEQUENCE DESCRIPTION: SEQ ID NO:144:

```
Cys  Arg  Ala  Ala  Phe  Leu  Phe  Gln  Ala  Ile  Leu  Leu  His  Ile  Gln  Asp
1                   5                        10                       15
Gln
```

( 2 ) INFORMATION FOR SEQ ID NO:145:

( i ) SEQUENCE CHARACTERISTICS:
    ( A ) LENGTH: 77 amino acids
    ( B ) TYPE: amino acid
    ( C ) STRANDEDNESS: single
    ( D ) TOPOLOGY: linear ( i i ) MOLECULE TYPE: Protein ( x i ) SEQUENCE DESCRIPTION: SEQ ID NO:145:

```
Phe  Phe  Tyr  Pro  Ser  Ala  Leu  Gln  Leu  Arg  Ala  Arg  Ile  His  Leu  Pro
1                   5                        10                       15

Gln  Arg  Ala  Val  Tyr  Ile  Val  Phe  Leu  Phe  Val  Ala  Cys  Val  Tyr  Ile
               20                       25                       30

Gln  Ile  Val  Ser  Leu  Ala  Phe  Tyr  Asp  Pro  Pro  His  Phe  Trp  Gln  Ile
               35                       40                       45

Lys  Asn  Gly  His  Gln  Ser  Thr  His  Lys  Cys  Cys  Ala  Val  Asp  Gln  Cys
          50                       55                       60

Pro  Gln  Ala  Phe  Arg  Leu  Gly  Arg  Ile  Leu  Phe  Ser  Leu
65                       70                       75
```

( 2 ) INFORMATION FOR SEQ ID NO:146:

( i ) SEQUENCE CHARACTERISTICS:
    ( A ) LENGTH: 81 amino acids
    ( B ) TYPE: amino acid
    ( C ) STRANDEDNESS: single
    ( D ) TOPOLOGY: linear ( i i ) MOLECULE TYPE: Protein ( x i ) SEQUENCE DESCRIPTION: SEQ ID NO:146:

```
Pro  Ile  Ser  Asn  Ser  Thr  Arg  Ala  Arg  Ser  Pro  Phe  Leu  Val  Ser  Thr
1                   5                        10                       15

Ser  Val  Phe  Pro  Cys  Ser  Gly  Ala  Ser  Val  Ile  His  Ala  Ser  Cys  Leu
               20                       25                       30
```

```
Met  Pro  Ser  Thr  Ile  Met  Thr  Asp  Phe  Pro  Val  Leu  Gln  Leu  Ala  Leu
          35                       40                      45

Lys  Arg  Asp  Gly  Ile  Asp  Met  Gln  Gln  Phe  Phe  Arg  Met  Asn  His  Val
     50                       55                      60

Leu  Phe  Pro  Pro  Leu  Phe  Gly  Ala  Ala  Leu  Ala  Ser  Ala  Phe  Ser  Asn
65                       70                      75                       80

Ser
```

( 2 ) INFORMATION FOR SEQ ID NO:147:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:147:

```
Met  Ile  Arg  Ser  Phe  Glu
1                   5
```

( 2 ) INFORMATION FOR SEQ ID NO:148:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:148:

```
Ile  Glu  Phe  Pro  Phe  Arg  Lys  Ser  Thr  Ala  Ala  Leu  Asp  Ala  Ser  Ser
1                   5                       10                      15

Asn  Ser  Gly  Ala  Ala  Ala  Ile
               20
```

( 2 ) INFORMATION FOR SEQ ID NO:149:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:149:

```
Lys  Glu  Ala  Leu  Leu  Phe  Cys  Glu
1                   5
```

( 2 ) INFORMATION FOR SEQ ID NO:150:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:150:

```
Glu  Leu  Arg  Ser  Asn  Thr  Ala  Ala  Ile  Ser  Arg  Pro  Phe  Glu  Tyr  Gly
1                   5                       10                      15

Asn  Leu  Ser  Phe  Ser  Ser  Ser  Leu
               20
```

( 2 ) INFORMATION FOR SEQ ID NO:151:

( i ) SEQUENCE CHARACTERISTICS:
        ( A ) LENGTH: 56 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:151:

```
Ile Gly Phe Val Ser Pro His Gly Thr Ala Arg Asn Gly Ala Gly Leu
 1               5                  10                  15
Phe Ser Ala Cys Phe Val Phe Ala Asn Thr Phe Thr Ser Arg Arg Pro
            20                  25                  30
Tyr Thr Ile Val Gln Cys Phe Phe Leu Phe Ala Leu Pro Glu Thr Ala
        35                  40                  45
Lys Arg Leu Glu Gln Ser Ala Val
50                  55
```

( 2 ) INFORMATION FOR SEQ ID NO:152:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:152:

```
Ile Phe Ser Leu Ala Phe Pro Ala Val Ser Ile Cys Ser Ser Phe
 1               5                  10                  15
```

( 2 ) INFORMATION FOR SEQ ID NO:153:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:153:

```
Met Thr Gly Val Lys Ser Val Ala Asp Arg Gln Phe Gly His Gly
 1               5                  10                  15
```

( 2 ) INFORMATION FOR SEQ ID NO:154:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:154:

```
Lys Thr Thr Pro Ile Pro Val Cys Ser Thr Met Thr Phe Phe Val
 1               5                  10                  15
```

( 2 ) INFORMATION FOR SEQ ID NO:155:

( i ) SEQUENCE CHARACTERISTICS:
        ( A ) LENGTH: 60 amino acids
        ( B ) TYPE: amino acid (C) STRANDEDNESS: single
(D) TOPOLOGY: linear (i i) MOLECULE TYPE: Protein (x i) SEQUENCE DESCRIPTION: SEQ ID NO:155:

```
Ala Leu Arg Ser Pro Leu Glu Thr Arg Arg Ser Asn Pro Asp Gly
 1               5                  10                  15
Tyr Arg Thr Pro Pro Gly Ser Gln Gly Pro Ser Val Phe Pro Ser Ala
                20                  25                  30
Ala Leu Ala Arg Phe Ser Met Arg Tyr Asp Ser Phe Trp Met Ser Arg
            35                  40                  45
Ser Arg Arg Gln Glu Thr Gly Thr Ser Ala Pro Asn
        50                  55                  60
```

(2) INFORMATION FOR SEQ ID NO:156:

(i) SEQUENCE CHARACTERISTICS:
(A) LENGTH: 8 amino acids
(B) TYPE: amino acid
(C) STRANDEDNESS: single
(D) TOPOLOGY: linear (i i) MOLECULE TYPE: Protein (x i) SEQUENCE DESCRIPTION: SEQ ID NO:156:

```
Thr Arg Asn Leu Arg Asn Glu Gly
 1               5
```

(2) INFORMATION FOR SEQ ID NO:157:

(i) SEQUENCE CHARACTERISTICS:
(A) LENGTH: 5 amino acids
(B) TYPE: amino acid
(C) STRANDEDNESS: single
(D) TOPOLOGY: linear (i i) MOLECULE TYPE: Protein (x i) SEQUENCE DESCRIPTION: SEQ ID NO:157:

```
Phe Leu Leu Gln Ser
 1               5
```

(2) INFORMATION FOR SEQ ID NO:158:

(i) SEQUENCE CHARACTERISTICS:
(A) LENGTH: 45 amino acids
(B) TYPE: amino acid
(C) STRANDEDNESS: single
(D) TOPOLOGY: linear (i i) MOLECULE TYPE: Protein (x i) SEQUENCE DESCRIPTION: SEQ ID NO:158:

```
Leu Ala Leu Phe Ser Phe Asp His Asn Phe Asn Arg Leu Leu Ala Val
 1               5                  10                  15
Ile Cys Phe Leu Arg Phe Leu Phe Gly Lys Leu Gln Phe Leu Ile Phe
                20                  25                  30
Asn Phe Leu Phe Lys Leu Ile Trp Lys Gln Ile Lys Ile
            35                  40                  45
```

(2) INFORMATION FOR SEQ ID NO:159:

(i) SEQUENCE CHARACTERISTICS:
(A) LENGTH: 68 amino acids
(B) TYPE: amino acid
(C) STRANDEDNESS: single (D) TOPOLOGY: linear (ii) MOLECULE TYPE: Protein (xi) SEQUENCE DESCRIPTION: SEQ ID NO:159:

```
Leu Leu Lys Arg Leu His Phe Ile Cys Lys Leu Asp Gly Asn Ala Ser
  1               5                  10                  15
Phe Pro Ser Phe Ala Ser Val Thr Met Val Pro Ser Thr Ser Pro Glu
                20                  25                  30
Ser Leu Thr Ser Thr Lys Leu Ile Ser Phe Ile Ile Gly Leu Ser Ser
             35                  40                  45
Ser Ser Asn Ser Gly Pro Asp Phe Pro Thr Ala Trp Thr Ser Phe Phe
         50                  55                  60
Pro Lys Val Thr
 65
```

(2) INFORMATION FOR SEQ ID NO:160:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:160:

```
Ser Val Ile Ser Ala Asn Ala Ile Leu Ile
 1               5                  10
```

(2) INFORMATION FOR SEQ ID NO:161:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:161:

```
Thr Cys Ser Thr Ser Ile Ala Ser Ile Asn Ile Ser Leu Thr Ile Ser
  1               5                  10                  15
Phe Leu Met Arg Ile Ser Ala Ala Thr Phe Ser Phe Phe Lys Ser Arg
                20                  25                  30
Leu Pro Val Thr
             35
```

(2) INFORMATION FOR SEQ ID NO:162:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:162:

```
Ala Leu Ser Gly Glu
 1               5
```

(2) INFORMATION FOR SEQ ID NO:163:

(i) SEQUENCE CHARACTERISTICS:
        (A) LENGTH: 14 amino acids ( B ) TYPE: amino acid
( C ) STRANDEDNESS: single
( D ) TOPOLOGY: linear ( i i ) MOLECULE TYPE: Protein ( x i ) SEQUENCE DESCRIPTION: SEQ ID NO:163:

Pro Ala Leu Ile Ala Asp Cys Val Ala Leu Lys Leu Leu Thr
1               5                   10

( 2 ) INFORMATION FOR SEQ ID NO:164:

( i ) SEQUENCE CHARACTERISTICS:
( A ) LENGTH: 60 amino acids
( B ) TYPE: amino acid
( C ) STRANDEDNESS: single
( D ) TOPOLOGY: linear ( i i ) MOLECULE TYPE: Protein ( x i ) SEQUENCE DESCRIPTION: SEQ ID NO:164:

Tyr Arg Gln Asn Ser Arg Trp Arg Ser Phe Asn Ser Ser Leu Phe Ile
1               5                   10                  15

Gly Arg Cys Phe Cys Ser Phe Leu Asp Ala Glu Asn Ser Ala Ser Phe
                20                  25                  30

His Leu Ser Cys Phe Phe Gln Met Pro Ile Val Phe Ala Glu Thr Pro
            35                  40                  45

Ile Val Ser Ala Ile Ala Arg Phe Val Ile Phe Pro
        50                  55                  60

( 2 ) INFORMATION FOR SEQ ID NO:165:

( i ) SEQUENCE CHARACTERISTICS:
( A ) LENGTH: 34 amino acids
( B ) TYPE: amino acid
( C ) STRANDEDNESS: single
( D ) TOPOLOGY: linear ( i i ) MOLECULE TYPE: Protein ( x i ) SEQUENCE DESCRIPTION: SEQ ID NO:165:

Ile Ala Asn Ala Cys Ser Arg Cys Cys Val Phe Met Leu Leu His His
1               5                   10                  15

Arg His Leu Gln His Gly Cys Leu Phe Ile Lys Ala Ala Asp Gln Pro
                20                  25                  30

Ala Ala ( 2 ) INFORMATION FOR SEQ ID NO:166:

( i ) SEQUENCE CHARACTERISTICS:
( A ) LENGTH: 18 amino acids
( B ) TYPE: amino acid
( C ) STRANDEDNESS: single
( D ) TOPOLOGY: linear ( i i ) MOLECULE TYPE: Protein ( x i ) SEQUENCE DESCRIPTION: SEQ ID NO:166:

Cys His Ala Leu Phe Thr Tyr Arg Trp Gln Thr Tyr Asp Lys Leu Ser
1               5                   10                  15

Gly Lys ( 2 ) INFORMATION FOR SEQ ID NO:167:

( i ) SEQUENCE CHARACTERISTICS:
( A ) LENGTH: 11 amino acids ( B ) TYPE: amino acid
( C ) STRANDEDNESS: single
( D ) TOPOLOGY: linear ( i i ) MOLECULE TYPE: Protein ( x i ) SEQUENCE DESCRIPTION: SEQ ID NO:167:

Ser Ile His Phe Phe Leu Leu Ser Leu His Leu
1               5                   1 0

( 2 ) INFORMATION FOR SEQ ID NO:168:

( i ) SEQUENCE CHARACTERISTICS:
( A ) LENGTH: 40 amino acids
( B ) TYPE: amino acid
( C ) STRANDEDNESS: single
( D ) TOPOLOGY: linear ( i i ) MOLECULE TYPE: Protein ( x i ) SEQUENCE DESCRIPTION: SEQ ID NO:168:

Thr Arg Pro Phe Asn Arg Arg Leu His Cys Arg Phe Phe Tyr Ala Glu
1               5                   1 0                  1 5

Lys Ile Gly Asp Pro Phe Ile Arg Lys Thr Phe Tyr Leu Met Gln Gln
                2 0                  2 5                  3 0

Lys His Phe Leu Phe Ser Val Arg
            3 5              4 0

( 2 ) INFORMATION FOR SEQ ID NO:169:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: Protein ( x i ) SEQUENCE DESCRIPTION: SEQ ID NO:169:

Cys Phe Ser Asn Ser Ile Ser Val Phe Phe
1               5                   1 0

( 2 ) INFORMATION FOR SEQ ID NO:170:

( i ) SEQUENCE CHARACTERISTICS:
( A ) LENGTH: 13 amino acids
( B ) TYPE: amino acid
( C ) STRANDEDNESS: single
( D ) TOPOLOGY: linear ( i i ) MOLECULE TYPE: Protein ( x i ) SEQUENCE DESCRIPTION: SEQ ID NO:170:

Tyr Leu Ser Val Arg Leu Lys His His Ser Ala Gly Lys
1               5                   1 0

( 2 ) INFORMATION FOR SEQ ID NO:171:

( i ) SEQUENCE CHARACTERISTICS:
( A ) LENGTH: 54 amino acids
( B ) TYPE: amino acid
( C ) STRANDEDNESS: single
( D ) TOPOLOGY: linear ( i i ) MOLECULE TYPE: Protein ( x i ) SEQUENCE DESCRIPTION: SEQ ID NO:171:

Phe Asp Asp Ser Arg Val Leu Asp His Gln Pro Leu Val Asn Ile Thr
1               5                   1 0                  1 5

Pro Val Asn Arg Pro Ser Asp Ala Gly Leu Pro Ser Phe Phe Lys Pro
            20                  25                  30

Phe Cys Tyr Ile Phe Lys Ile Ser Asn His Ile Ser Asp Asp Phe Phe
        35                  40                  45

Ile Leu Gln Leu Phe Ser
        50

( 2 ) INFORMATION FOR SEQ ID NO:172:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:172:

Glu His Gly Phe Ile Cys Leu Ser Glu Arg Phe Ile Leu Tyr Ser Cys
1               5                   10                  15

Leu Phe Glu Arg Ala Phe Ile Phe Lys
            20                  25

( 2 ) INFORMATION FOR SEQ ID NO:173:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:173:

Val Leu His Ser Met Ile Leu Leu Ile Phe Gly Lys
1               5                   10

( 2 ) INFORMATION FOR SEQ ID NO:174:

( i ) SEQUENCE CHARACTERISTICS:
        ( A ) LENGTH: 59 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:174:

Lys Thr Asp Thr Asn Gln Arg Thr Asn Ala Val Gln Leu Ile Ser Val
1               5                   10                  15

Arg Arg Leu Ser Val Leu Asp Val Phe Cys Phe Arg Phe Asn Leu Ile
            20                  25                  30

Cys Ser Arg Phe Gln Ile Pro His Glu Gln Asp Arg Pro Phe Leu Phe
        35                  40                  45

Arg Arg Ala Phe Phe His Ala Leu Ala Leu Leu
        50                  55

( 2 ) INFORMATION FOR SEQ ID NO:175:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: Protein ( x i ) SEQUENCE DESCRIPTION: SEQ ID NO:175:

Ser Met Leu Leu Ala
1               5

( 2 ) INFORMATION FOR SEQ ID NO:176:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: Protein ( x i ) SEQUENCE DESCRIPTION: SEQ ID NO:176:

Cys Arg Pro Gln
1

( 2 ) INFORMATION FOR SEQ ID NO:177:

( i ) SEQUENCE CHARACTERISTICS:
( A ) LENGTH: 22 amino acids
( B ) TYPE: amino acid
( C ) STRANDEDNESS: single
( D ) TOPOLOGY: linear ( i i ) MOLECULE TYPE: Protein ( x i ) SEQUENCE DESCRIPTION: SEQ ID NO:177:

Arg Ile Phe Pro Ser Ser Ser Trp Leu Leu Ser Val Thr Glu Ser Ile
1               5                   10                  15
Cys Ser Ser Phe Phe Gly
            20

( 2 ) INFORMATION FOR SEQ ID NO:178:

( i ) SEQUENCE CHARACTERISTICS:
( A ) LENGTH: 21 amino acids
( B ) TYPE: amino acid
( C ) STRANDEDNESS: single
( D ) TOPOLOGY: linear ( i i ) MOLECULE TYPE: Protein ( x i ) SEQUENCE DESCRIPTION: SEQ ID NO:178:

Ile Met Phe Tyr Phe Leu Pro Phe Ser Val Gln Arg Leu Leu Gln Leu
1               5                   10                  15
Phe Leu Ile Ala Glu
            20

( 2 ) INFORMATION FOR SEQ ID NO:179:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: Protein ( x i ) SEQUENCE DESCRIPTION: SEQ ID NO:179:

Tyr Ala Pro Leu Asn Glu
1               5

( 2 ) INFORMATION FOR SEQ ID NO:180:

( i ) SEQUENCE CHARACTERISTICS:

(A) LENGTH: 10 amino acids
(B) TYPE: amino acid
(C) STRANDEDNESS: single
(D) TOPOLOGY: linear (ii) MOLECULE TYPE: Protein (xi) SEQUENCE DESCRIPTION: SEQ ID NO:180:

Asn Ser Leu Ser Glu Asn Gln Leu Leu Leu
1               5                   10

(2) INFORMATION FOR SEQ ID NO:181:

(i) SEQUENCE CHARACTERISTICS:
(A) LENGTH: 21 amino acids
(B) TYPE: amino acid
(C) STRANDEDNESS: single
(D) TOPOLOGY: linear (ii) MOLECULE TYPE: Protein (xi) SEQUENCE DESCRIPTION: SEQ ID NO:181:

Thr Leu Pro Ala Ile Gln Ala Gln Arg Pro Ser Lys Arg His Cys Phe
1               5                   10                  15
Phe Ala Asn Lys Ser
            20

(2) INFORMATION FOR SEQ ID NO:182:

(i) SEQUENCE CHARACTERISTICS:
(A) LENGTH: 76 amino acids
(B) TYPE: amino acid
(C) STRANDEDNESS: single
(D) TOPOLOGY: linear (ii) MOLECULE TYPE: Protein (xi) SEQUENCE DESCRIPTION: SEQ ID NO:182:

Gly Gln Ile Gln Leu Gln Ser Ala Ala Arg Leu Ser Thr Glu Ile Phe
1               5                   10                  15
Leu Phe Leu Leu His Leu Asn Lys Tyr Arg Ser Val Ser Tyr Pro Arg
                20                  25                  30
Thr Gly Gln His Ala Thr Ala Gln Gly Phe Ser Leu Pro Val Leu Ser
            35                  40                  45
Leu Pro Thr Leu Ser Leu Pro Val Val Leu Ile Pro Leu Phe Asn Val
        50                  55                  60
Phe Phe Cys Ser Leu Cys Pro Lys Gln Gln Ser Asp
65                  70                  75

(2) INFORMATION FOR SEQ ID NO:183:

(i) SEQUENCE CHARACTERISTICS:
(A) LENGTH: 24 amino acids
(B) TYPE: amino acid
(C) STRANDEDNESS: single
(D) TOPOLOGY: linear (ii) MOLECULE TYPE: Protein (xi) SEQUENCE DESCRIPTION: SEQ ID NO:183:

Ser Ser Gln Leu Phe Asn His Arg Tyr Ser Ala Ser Leu Phe Pro Leu
1               5                   10                  15
Ser Ala Phe Ala Pro Ala Phe Glu
            20

(2) INFORMATION FOR SEQ ID NO:184:

(i) SEQUENCE CHARACTERISTICS:
    (A) LENGTH: 25 amino acids
    (B) TYPE: amino acid
    (C) STRANDEDNESS: single
    (D) TOPOLOGY: linear (ii) MOLECULE TYPE: Protein (xi) SEQUENCE DESCRIPTION: SEQ ID NO:184:

Gln Ala Leu Ser Gln Ser Arg Thr Gly Ser Ser Asp Met Asp Glu Lys
 1               5                   1 0                     1 5

Gln Leu Gln Tyr Arg Tyr Val Pro Gln
               2 0                2 5

(2) INFORMATION FOR SEQ ID NO:185:

(i) SEQUENCE CHARACTERISTICS:
    (A) LENGTH: 7 amino acids
    (B) TYPE: amino acid
    (C) STRANDEDNESS: single
    (D) TOPOLOGY: linear (ii) MOLECULE TYPE: Protein (xi) SEQUENCE DESCRIPTION: SEQ ID NO:185:

Leu Ser Leu Phe Asp Lys Ala
 1               5